US011660356B2

(12) United States Patent
Lahoutte et al.

(10) Patent No.: US 11,660,356 B2
(45) Date of Patent: May 30, 2023

(54) RADIO-LABELLED ANTIBODY FRAGMENTS FOR USE IN THE PROGNOSIS, DIAGNOSIS OF CANCER AS WELL AS FOR THE PREDICTION OF CANCER THERAPY RESPONSE

(71) Applicant: Vrije Universiteit Brussel, Brussels (BE)

(72) Inventors: Tony Lahoutte, Ganshoren (BE); Nick Devoogdt, Eppegem-Zemst (BE); Marleen Keyaerts, Tervuren (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 415 days.

(21) Appl. No.: 16/827,032

(22) Filed: Mar. 23, 2020

(65) Prior Publication Data

US 2020/0276340 A1  Sep. 3, 2020

Related U.S. Application Data

(63) Continuation of application No. 15/329,860, filed as application No. PCT/EP2015/067424 on Jul. 29, 2015, now abandoned.

(30) Foreign Application Priority Data

Jul. 29, 2014 (EP) .................................. 14178946

(51) Int. Cl.
| | | |
|---|---|---|
| *G01N 33/574* | (2006.01) | |
| *A61K 51/10* | (2006.01) | |
| *C07K 16/30* | (2006.01) | |
| *C07K 16/32* | (2006.01) | |

(52) U.S. Cl.
CPC ...... *A61K 51/1051* (2013.01); *A61K 51/1045* (2013.01); *A61K 51/1069* (2013.01); *A61K 51/1072* (2013.01); *A61K 51/1078* (2013.01); *C07K 16/30* (2013.01); *C07K 16/3015* (2013.01); *C07K 16/32* (2013.01); *G01N 33/5748* (2013.01); *G01N 33/57415* (2013.01); *C07K 2317/35* (2013.01); *C07K 2317/565* (2013.01); *C07K 2317/569* (2013.01); *C07K 2317/92* (2013.01); *G01N 2333/82* (2013.01)

(58) Field of Classification Search
None
See application file for complete search history.

(56) References Cited

U.S. PATENT DOCUMENTS

| 9,855,348 B2 | 1/2018 | Devoogdt et al. |
|---|---|---|
| 2005/0037421 A1 | 2/2005 | Honda et al. |
| 2009/0304590 A1 | 12/2009 | Gill |
| 2010/0209343 A1 | 8/2010 | Bander |
| 2016/0030606 A1 | 2/2016 | Devoogdt et al. |
| 2018/0036442 A1 | 2/2018 | Lahoutte |
| 2020/0276340 A1 | 9/2020 | Lahoutte et al. |

FOREIGN PATENT DOCUMENTS

| EP | 1134231 A1 | 9/2001 |
|---|---|---|
| EP | 1433793 A1 | 6/2004 |
| WO | WO 1994/004678 A1 | 3/1994 |
| WO | WO 1994/025591 A1 | 11/1994 |
| WO | WO 1995/004079 A1 | 2/1995 |
| WO | WO 1996/008565 A2 | 3/1996 |
| WO | WO 1996/034103 A1 | 10/1996 |
| WO | WO 1997/049805 A2 | 12/1997 |
| WO | WO 1999/037681 A2 | 7/1999 |
| WO | WO 2000/040968 A1 | 7/2000 |
| WO | WO 2000/043507 A1 | 7/2000 |
| WO | WO 2000/065057 A2 | 11/2000 |
| WO | WO 2001/021817 A1 | 3/2001 |
| WO | WO 2001/040310 A1 | 6/2001 |
| WO | WO 2001/044301 A1 | 6/2001 |
| WO | WO 2001/090190 A2 | 11/2001 |
| WO | WO 2002/048193 A2 | 6/2002 |
| WO | WO 2003/035694 A2 | 5/2003 |
| WO | WO 2003/050531 A2 | 6/2003 |
| WO | WO 2003/054016 A2 | 7/2003 |
| WO | WO 2003/055527 A2 | 7/2003 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A2 | 7/2004 |
| WO | WO 2009/068625 A2 | 6/2009 |
| WO | WO 2010/004432 A1 | 1/2010 |
| WO | WO 2010/042815 A2 | 4/2010 |
| WO | WO 2011/051327 A1 | 5/2011 |
| WO | WO 2013/110531 A2 | 8/2013 |
| WO | WO 2014/140376 A1 | 9/2014 |
| WO | WO 2015/073746 A2 | 5/2015 |

OTHER PUBLICATIONS

Atarhouch et al. (1997) "cDNA sequence coding for the constant region of the dromedary g3 heavy-chain antibody," Journal of Camel Practice and Research. 4:177-182.

(Continued)

*Primary Examiner* — Mark Halvorson
(74) *Attorney, Agent, or Firm* — Lathrop GPM LLP; James H. Velema; Judith L. Stone-Hulslander

(57) ABSTRACT

The application provides polypeptides comprising or essentially consisting of at least one heavy chain variable domain of a heavy chain antibody ($V_{HH}$) or a functional fragment thereof, wherein said $V_{HH}$ or a functional fragment thereof specifically binds to a target protein that is present on and/or specific for a solid tumor, e.g. HER2. The application further provides nucleic acids encoding such polypeptides; methods for preparing such polypeptides; host cells expressing or capable of expressing such polypeptides; compositions, and in particular to pharmaceutical compositions, that comprise such polypeptides, nucleic acids and/or host cells. The application further provides such polypeptides, nucleic acids, host cells and/or compositions, for use in methods for detection, imaging, prognosis and diagnosis of cancer as well as for predicting patient response(s) to therapeutics.

30 Claims, 8 Drawing Sheets

Specification includes a Sequence Listing.

(56) References Cited

OTHER PUBLICATIONS

Bond et al. (2003) "Contributions of CDR3 to V H H domain stability and the design of monobody scaffolds for naive antibody libraries," J. Mol. Biol. 332(3):643-55.

Bond et al. (2005) "A structure-based database of antibody variable domain diversity," J. Mol. Biol. 348(3):699-709.

Byers, "What Can Randomized Controlled Trials Tell Us About Nutrition and Cancer Prevention?", CA Cancer Journ, Nov./Dec. 1999, vol. 49, No. 6, pp. 353-361.

Choi et al. (Aug. 1, 2014) "N-Succinimidyl guanidinomethyl iodobenzoate protein radiohalogenation agents: Influence of isomeric substitution on radiolabeling and target cell residualization," Nucl. Med. Biol. 41(10):802-812.

Chothia et al. (1989) "Conformations of immunoglobulin hypervariable regions," Nature. 342:877-883.

Colman, "Effects of amino acid sequence changes on antibody-antigen interactions", Research In Immunology, 1994, vol. 145, pp. 33-36.

Conrath et al. (2001) "Beta-lactamase inhibitors derived from single-domain antibody fragments elicited in the camelidae," Antimicrob. Agents Chemother. 45(10):2807-12.

Conrath et al. (2001) "Camel single-domain antibodies as modular building units in bispecific and bivalent antibody constructs," J. Biol. Chem. 276(10):7346-50.

Conrath et al. (2003) "Emergence and evolution of functional heavy-chain antibodies in Camelidae," Dev. Comp. Immunol. 27(2):87-103.

Cortf7-Retamozo et al., "99mTc-Labeled nanobodies: a new type of targeted probes for imaging antigen expression," Current Radiopharmaceuticals, 2008, 1(1):37-41.

Cortf7-Retamozo et al. (2002) "Efficient tumor targeting by single-domain antibody fragments of camels," Int. J. Cancer. 98(3):456-462.

Cortf7-Retamozo et al. (2004) "Efficient cancer therapy with a nanobody-based conjugate," Cancer Res. 64(8):2853-7.

Davies et al. (1994) "'Camelising' human antibody fragments: NMR studies on VH domains," FEBS Lett. 339(3):285-90.

Davies et al. (1995) "Antibody VH domains as small recognition units," Biotechnology (NY). 13(5):475-9.

Davies et al. (1996) "Single antibody domains as small recognition units: design and in vitro antigen selection of camelized, human VH domains with improved protein stability," Protein Eng. 9(6):531-7.

Decanniere et al. (1999) "A single-domain antibody fragment in complex with RNase A: non-canonical loop structures and nanomolar affinity using two CDR loops," Structure Fold. Des. 7(4):361-70.

Decanniere et al. (2000) "Canonical antigen-binding loop structures in immunoglobulins: more structures, more canonical classes?" J. Mol. Biol. 300(1):83-91.

Decanniere et al. (2001) "Degenerate interfaces in antigen-antibody complexes," J. Mol. Biol. 313(3):473-8.

De Genst et al. (2002) "Kinetic and affinity predictions of a protein-protein interaction using multivariate experimental design," J. Biol. Chem. 277(33):29897-907.

De Genst et al. (2004) "Chemical basis for the affinity maturation of a camel single domain antibody," J. Biol. Chem. 279(51):53593-601.

De Genst et al. (2005) "Strong in vivo maturation compensates for structurally restricted H3 loops in antibody repertoires," J. Biol. Chem. 280(14):14114-21.

Dekker et al. (2003) "Intracellularly expressed single-domain antibody against p15 matrix protein prevents the production of porcine retroviruses," J. Virol. 77(22):12132-9.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody", Journal of Immunology, 2002, vol. 169, pp. 3076-3084.

Desmyter et al. (1996) "Crystal structure of a camel single-domain VH antibody fragment in complex with lysozyme," Nat. Struct. Biol. 3(9):803-11.

Desmyter et al. (2001) "Antigen specificity and high affinity binding provided by one single loop of a camel single-domain antibody," J. Biol. Chem. 276(28):26285-90.

Desmyter et al. (2002) "Three camelid VHH domains in complex with porcine pancreatic alpha-amylase. Inhibition and versatility of binding topology," J. Biol. Chem. 277(26):23645-50.

D'Huyvetter et al., "Targeted Radionuclide Therapy with A 177Lu-labeled Anti-HER2 Nanobody," Theranostics, 2004, 4(7):708-720.

D'Huyvetter et al., "Development of 177Lu-nanobodies for radioimmunotherapy of HER2-positive breast cancer: evaluation of different bifunctional chelators," Contrast Media and Molecular Imaging, 2012, 7:254-264.

D'Huyvetter et al., "Nanobody-based Targeted Radiotherapy for Cancer Treatment," In; The European Cooperation in the field of Science and Technology Meeting 2013: Theragnostics Imaging and Therapy: An Action to Develop Novel Nanosized Systems for Imaging-Guided Drug Delivery. Action TD1004, Sep. 1-3, 2013, Athens, Greece—Meeting abstract only.

D'Huyvetter, "Evaluation of bivalent antiHER2 Nanobody constructs for improved cellular retention and in vivo tumor targeting," Abstract for Poster Presentation No. P529 Presented In; The World Molecular Imaging Congress, 2012, Dublin, Ireland. 2 pgs.

D'Huyvetter, "Evaluation of bivalent antiHER2 Nanobody constructs for improved cellular retention and in vivo tumor targeting," Poster for Poster Presentation No. P529 Presented In; The World Molecular Imaging Congress, 2012, Dublin, Ireland. 1 pg.

D'Huyvetter, et al., Expert Opinion on Drug Delivery, 2014, vol. 11, No. 12, pp. 1939-1954.

Dolk et al. (2005) "Induced refolding of a temperature denatured llama heavy-chain antibody fragment by its antigen," Proteins. 59(3):555-64.

Dolk et al. (2005) "Isolation of llama antibody fragments for prevention of dandruff by phage display in shampoo," Appl. Environ. Microbiol. 71(1):442-50.

Dumoulin et al. (2002) "Single-domain antibody fragments with high conformational stability," Protein Sci. 11(3):500-15.

Dumoulin et al. (2003) "A camelid antibody fragment inhibits the formation of amyloid fibrils by human lysozyme," Nature. 424(6950):783-8.

Dumoulin et al. (2005) "Reduced global cooperativity is a common feature underlying the amyloidogenicity of pathogenic lysozyme mutations," J. Mol. Biol. 346(3):773-88.

Ewert et al. (2002) "Biophysical properties of camelid V(HH) domains compared to those of human V(H)3 domains," Biochemistry. 41(11):3628-36.

Eyer et al., "Single-domain antibody fragments derived from heavy-chain antibodies: a review," Veterinarni Medicina, Sep. 2012, 57:439-513.

Ferrat et al. (2002) "A peptide mimic of an antigenic loop of alpha-human chorionic gonadotropin hormone: solution structure and interaction with a llama V(HH) domain," Biochem. J. 366(Pt 2):415-22.

Frenken et al. (1998) "Recent advances in the large-scale production of antibody fragments using lower eukaryotic microorganisms," Res. Immunol. 149(6):589-99.

Frenken et al. (2000) "Isolation of antigen specific llama VHH antibody fragments and their high level secretion by *Saccharomyces cerevisiae*," J. Biotechnol. 78(1):11-21.

Gainkam et al., "Comparison of the biodistribution and tumor targeting of two 99mTc-labeled anti-EGFR nanobodies in mice, using pinhole SPECT/micro-CT," J. Nucl. Med., 2008, 49(5):788-795.

Gainkam et al., "Correlation Between Epidermal Growth Factor Receptor-Specific Nanobody Uptake and Tumor Burden: A Tool for Noninvasive Monitoring of Tumor Response to Therapy," Mol. Imaging Biol., 2010 13(5):940-948.

Ghahroudi et al. (1997) "Selection and identification of single domain antibody fragments from camel heavy-chain antibodies," FEBS Lett. 414(3):521-6.

(56) References Cited

OTHER PUBLICATIONS

Gharoudi et al. (1995) "Identification of soluble, stable camel VH antibody fragments expressed in *E. coli*, with specificity and neutralizing activity for tetanus toxoid," Mededelingen Faculteit Landbouwkundige en Toegepaste Biologische Wetenschappen Universiteit Gent. 60(4A-B):2097-2100.

Gibbs, "Nanobodies", Scientific American, 2005, vol. 293, No. 2, pp. 67-71.

Granziero et al., "Adoptive immunotherapy prevents prostate cancer in a transgenic animal model", European Journal of Immunology, 1999, vol. 29, pp. 1127-1138.

Hamers-Casterman et al. (1993) "Naturally occurring antibodies devoid of light chains," Nature. 363(6428):446-8.

Harmsen et al. (2000) "Llama heavy-chain V regions consist of at least four distinct subfamilies revealing novel sequence features," Mol. Immunol. 37(10):579-90.

Harmsen et al. (2002) "Stimulation of chymosin secretion by simultaneous expression with chymosin-binding llama single-domain antibody fragments in yeast," Appl. Microbiol. Biotechnol. 60(4):449-54.

HOOGENBOOM (2005) "Selecting and screening recombinant antibody libraries," Nature Biotechnology. 23(9):1105-1116.

Huang et al. (2005) "Protein studies in dysferlinopathy patients using llama-derived antibody fragments selected by phage display," Eur. J. Hum. Genet. 13(6):721-30.

Huang et al., "SPECT imaging with 99mTc-labeled EGFR-specific nanobody for in vivo monitoring of EGFR expression," Molecular Imaging and Biology, 2008, 10(3):167-175.

International Preliminary Report on Patentability corresponding to International Patent Application No. PCT/EP2015/066430, completed Jun. 22, 2016.

International Search Report with Written Opinion corresponding to International Patent Application No. PCT/EP2015/066430, dated Nov. 10, 2015.

International Search Report with Written Opinion corresponding to International Patent Application No. PCT/EP2015/067424, dated Nov. 11, 2015.

International Preliminary Report on Patentability corresponding to International Patent Application No. PCT/EP2016/066934, dated Jan. 23, 2018.

International Search Report with Written Opinion corresponding to International Patent Application No. PCT/EP2016/066934, dated Oct. 27, 2016.

Jobling et al. (2003) "Immunomodulation of enzyme function in plants by single-domain antibody fragments," Nat. Biotechnol. 21(1):77-80.

Joosten et al. (2003) "The production of antibody fragments and antibody fusion proteins by yeasts and filamentous fungi," Microb. Cell Fact. 2(1):1. pp. 1-15.

Joosten et al. (2005) "Expression and production of llama variable heavy-chain antibody fragments (V(HH)s) by Aspergillus awamori," Appl. Microbiol. Biotechnol. 66(4):384-92.

Keyaerts et al., "Phase I Study of 68Ga-HER2-Nanobody for PET/CT Assessment of HER2 Expression in Breast Carcinoma", The Journal of Nuclear Medicine, vol. 57, No. 1, Jan. 2016, pp. 27-33.

Kijankka et al., "Rapid optical imaging of human breast tumour xenografts using anti-HER2 VHHs site-directly conjugated to IRDye 800CW for image-guided surgery", European Journal of Molecular Imaging, 2013, vol. 40, pp. 1718-1729.

Lah et al. (2003) "Recognition of the intrinsically flexible addiction antidote MazE by a dromedary single domain antibody fragment. Structure, thermodynamics of binding, stability, and influence on interactions with DNA," J. Biol. Chem. 278(16):14101-11.

Lauwereys et al. (1998) "Potent enzyme inhibitors derived from dromedary heavy-chain antibodies," EMBO J. 17(13):3512-20.

Ledeboer et al. (2002) "Preventing phage lysis of Lactococcus lactis in cheese production using a neutralizing heavy-chain antibody fragment from llama," J. Dairy Sci. 85(6):1376-82.

Li et al. (2003) "A soft docking algorithm for predicting the structure of antibody-antigen complexes," Proteins. 52(1):47-50.

Loris et al. (2003) "Crystal structure of the intrinsically flexible addiction antidote MazE," Biol. Chem. 278(30):28252-7.

Maccallum et al., "Antibody-antigen Interactions: Contact Analysis and Binding Site Topography", Journal of Molecular Biology, 1996, vol. 262, pp. 732-745.

Massa, "Site-specific coupling of Nanobodies® directed against the membrane protein HER2 for non-invasive, multi-modal imaging in pre-clinical cancer models," Master's Thesis for the fulfillment of the degree of Master of Bioscience Engineering: Cell and Gene Biotechnology—Medical Biotechnology. Vrije Universiteit Brussel. Brussels, Belgium, 2011, with English machine translation.

Meddeb-Mouelhi et al. (2003) "Immunized camel sera and derived immunoglobulin subclasses neutralizing Androctonus australis hector scorpion toxins," Toxicon. 42(7):785-91.

Muruganandam et al. (2002) "Selection of phage-displayed llama single-domain antibodies that transmigrate across human blood-brain barrier endothelium," FASEB J. 16(2):240-2.

Muyldermans (2001) "Single domain camel antibodies: current status," Reviews in Molecular Biotechnology. 74(4):277-302.

Muyldermans et al. (1994) "Sequence and structure of VH domain from naturally occurring camel heavy chain immunoglobulins lacking light chains," Protein Eng. 7(9):1129-3.

Muyldermans et al. (1999) "Unique single-domain antigen binding fragments derived from naturally occurring camel heavy-chain antibodies," J. Mol. Recognit. 12(2):131-40.

Muyldermans et al. (2001) "Recognition of antigens by single-domain antibody fragments: the superfluous luxury of paired domains," Trends Biochem Sci. 26(4):230-5.

Nguyen et al. (1998) "The specific variable domain of camel heavy-chain antibodies is encoded in the germline," J. Mol. Biol. 275(3):413-8.

Nguyen et al. (1999) "Loss of splice consensus signal is responsible for the removal of the entire C(H)1 domain of the functional camel IGG2A heavy-chain antibodies," Mol. Immunol. 36(8):515-24.

Nguyen et al. (2000) "Camel heavy-chain antibodies: diverse germline V(H)H and specific mechanisms enlarge the antigen-binding repertoire," EMBO J. 19(5):921-30.

Nguyen et al. (2001) "Functional heavy-chain antibodies in Camelidae," Adv. Immunol. 79:261-96.

Nguyen et al. (2002) "Heavy-chain antibodies in Camelidae; a case of evolutionary innovation," Immunogenetics. 54(1):39-47.

Nguyen et al. (2003) "Heavy-chain only antibodies derived from dromedary are secreted and displayed by mouse B cells," Immunology. 109(1):93-101.

Nicaise et al. (2004) "Affinity transfer by CDR grafting on a nonimmunoglobulin scaffold," Protein Sci. 13(7):1882-91.

Oliveira et al., "Targeting Tumors with Nanobodies for Cancer Imaging and Therapy," J. Controlled Release, 2013, 172(3):607-617.

Omidfar et al. (2004) "Production and characterization of a new antibody specific for the mutant EGF receptor, EGFRvIII, in Camelus bactrianus," Tumour Biol. 25(4):179-87.

Omidfar et al. (2004) "Production of a novel camel single-domain antibody specific for the type III mutant EGFR," Tumour Biol. 25(5-6):296-305.

Perez et al. (2001) "Thermal unfolding of a llama antibody fragment: a two-state reversible process," Biochemistry. 40(1):74-83.

Pleschberger et al. (2003) "Generation of a functional monomolecular protein lattice consisting of an s-layer fusion protein comprising the variable domain of a camel heavy chain antibody," Bioconjug. Chem. 14(2):440-8.

Pleschberger et al. (2004) "An S-layer heavy chain camel antibody fusion protein for generation of a nanopatterned sensing layer to detect the prostate-specific antigen by surface plasmon resonance technology," Bioconjug. Chem. 15(3):664-71.

Pruszynski et al., "Improved Tumor Targeting of Anti-HER2 Nanobody Through N-Succinimidyl 4-Guanidinomethyl-3-Iodobenzoate Radiolabeling," The Journal of Nuclear Medicine, 2014, 55(4):650-656.

(56) References Cited

OTHER PUBLICATIONS

Pruszynski et al., "Targeting breast carcinoma with radioiodinated anti-HER2 Nanobody", Nuclear Medicine and Biology, 2013, vol. 40, pp. 52-59.
Renisio et al. (2002) "Solution structure and backbone dynamics of an antigen-free heavy chain variable domain (VHH) from Llama," Proteins. 47(4):546-55.
Riechmann aet al. (1999) "Single domain antibodies: comparison of camel VH and camelised human VH domains," J. Immunol. Methods. 231(1-2):25-38.
Rudikoff et al., "Single amino acid substitution altering antigen-binding specificity", Proc. Natl. Acad. Sci. USA, Mar. 1982, vol. 79, No. 6, pp. 1979-1983.
Saerens et al. (2004) "Single domain antibodies derived from dromedary lymph node and peripheral blood lymphocytes sensing conformational variants of prostate-specific antigen," J. Biol. Chem. 279(50):51965-72.
Schoonooghe et al., "Novel applications of nanobodies for in vivo bio-imaging of inflamed tissues in inflammatory diseases and cancer," Immunobiology, 2012, 217(12):1266-1272.
Search Report with Search Opinion corresponding to European Patent Application No. 14178943.8, dated Apr. 28, 2015.
Sheriff et al. (1996) "Redefining the minimal antigen-binding fragment," Nat. Struct. Biol. 3(9):733-6.
Siontorou, "Nanobodies as novel agents for disease diagnosis and therapy," International Journal of Nanomedicine, Nov. 2013, 8:4215-4227.
Spinelli et al. (1996) "The crystal structure of a llama heavy chain variable domain," Nat. Struct. Biol. 3(9):752-7.
Spinelli et al. (2000) "Camelid heavy-chain variable domains provide efficient combining sites to haptens," Biochemistry. 39(6):1217-22.
Spinelli et al. (2001) "Lateral recognition of a dye hapten by a llama VHH domain," J. Mol. Biol. 311(1):123-9.
Spinelli et al. (2004) "Domain swapping of a llama VHH domain builds a crystal-wide beta-sheet structure," FEBS Lett. 564(1-2):35-40.
Stabin et al., "OLINDA/EXM: the second-generation personal computer software for internal dose assessment in nuclear medicine," J. Nucl. Med., 2005, 46:1023-1027.
Stijlemans et al. (2004) "Efficient targeting of conserved cryptic epitopes of infectious agents by single domain antibodies. African trypanosomes as paradigm," J Biol. Chem. 279(2):1256-61.
Su et al. (2002) "Adaptive evolution of variable region genes encoding an unusual type of immunoglobulin in camelids," Mol. Biol. Evol. 19(3):205-15.
Szpakowska, "Selection of HER2-Specific Internalising Nanobodies," Master's Thesis for the partial fulfillment of the degree of Master of Biomolecular Sciences, 2010, Vrije Universiteit Brussel. Brussels, Belgium.
Szynol et al. (2004) "Bactericidal effects of a fusion protein of llama heavy-chain antibodies coupled to glucose oxidase on oral bacteria," Antimicrob. Agents Chemother. 48(9):3390-5.
Thomassen et al. (2002) "Large-scale production of VHH antibody fragments by *Saccharomyces cerevisiae*," Enzyme Microb. Technol. 30:273-8.
Tijink et al., "Improved tumor targeting of anti-epidermal growth factor receptor Nanobodies through albumin binding: taking advantage of modular Nanobody technology," Molecular Cancer Therapeutics, 2008, 7(8):2288-2297.
Transue et al. (1998) "Camel single-domain antibody inhibits enzyme by mimicking carbohydrate substrate," Proteins. 32(4):515-22.
Vaidyanathan et al., "Improved xenograft targeting of tumor-specific anti-epidermal growth factor receptor variant III antibody labeled using N-succinimidyl 4-guanidinomethyl-3-iodobenzoate", Nuclear Medicine and Biology, 2002, vol. 29, pp. 1-11.
Van Der Linden et al. (1999) "Comparison of physical chemical properties of llama VHH antibody fragments and mouse monoclonal antibodies," Biochim. Biophys. Acta. 1431(1):37-46.

Van Der Linden et al. (2000) "Improved production and function of llama heavy chain antibody fragments by molecular evolution," J. Biotechnol. 80(3):261-70.
Van Der Linden et al. (2000) "Induction of immune responses and molecular cloning of the heavy chain antibody repertoire of Lama glama," J. Immunol. Methods. 240(1-2):185-95.
Van Der Vaart (2002) "Expression of VHH antibody fragments in *Saccharomyces cerevisiae*," Methods Mol. Biol. 178:359-66.
Vaneycken et al., "Preclinical screening of anti-HER2 nanobodies for molecular imaging of breast cancer", The FASEB Journal—Research Communication, Jul. 2011, vol. 25, pp. 2433-2446.
Van Gassen, "Characterization of anti-HER2 Nanobodies for non-invasive imaging of HER2 Positive Tumors," Master's Thesis for the fulfillment of the degree of Master of Biology: Genetics, Cellular and Developmental Biology. Vrije Universiteit Brussel. Brussels, Belgium, 2009, with English machine translation.
Van Koningsbruggen et al. (2003) "Llama-derived phage display antibodies in the dissection of the human disease oculopharyngeal muscular dystrophy," J. Immunol. Methods. 279(1-2):149-61.
Verheesen et al. (2003) "Beneficial properties of single-domain antibody fragments for application in immunoaffinity purification and immuno-perfusion chromatography," Biochim. Biophys. Acta. 1624(1-3):21-8.
Vosjan et al., "Facile labelling of an anti-epidermal growth factor receptor Nanobody with 68Ga via a novel bifunctional desferal chelate for immuno-PET," Eur. J. Nucl. Med. Mol. Imaging, 2011, 38(4):753-763.
Vosjan et al., "Nanobodies Targeting the Hepatocyte Growth Factor: Potential New Drugs for Molecular Cancer Therapy," Molecular Cancer Therapeutics, 2012, 11(4):1017-1025.
Vranken et al. (2002) "Solution structure of a llama single-domain antibody with hydrophobic residues typical of the VH/VL interface," Biochemistry. 41(27):8570-9.
Vu et al. (1997) "Comparison of llama VH sequences from conventional and heavy chain antibodies," Mol. Immunol. 34(16-17):1121-31.
Woolven et al. (1999) "The structure of the llama heavy chain constant genes reveals a mechanism for heavy-chain antibody formation," Immunogenetics. 50(1-2):98-101.
Xavier et al., "Synthesis, Preclinical Validation, Dosimetry, and Toxicity of 68Ga-NOTA-Anti-HER2 Nanobodies for iPET Imaging of HER2 Receptor Expression in Cancer," J. Nucl. Med., 2013, 54(5):776-784.
Xavier et al., "Anti-HER2 Nanobodies: Novel Theranostic Tools," In; The Abstracts of 7th World Molecular Imaging Congress Scientific Session 08: SS 46, Seoul, South Korea, Mol Imaging Biol, 2015, vol. 17, Suppl. 1, S1-S1352.
Yau et al. (2003) "Selection of hapten-specific single-domain antibodies from a nonimmunized llama ribosome display library," J. Immunol. Methods. 281(1-2):161-75.
Yau et al. (2005) "Affinity maturation of a V(H)H by mutational hotspot randomization," J. Immunol. Methods. 297(1-2):213-24.
Zarebski et al. (2005) "Llama single domain antibodies as a tool for molecular mimicry," J. Mol. Biol. 349(4):814-24.
Zhang et al. (2004) "Pentamerization of single-domain antibodies from phage libraries: a novel strategy for the rapid generation of high-avidity antibody reagents," J. Mol. Biol. 335(1):49-56.
U.S. Appl. No. 14/802,077, filed Jul. 17, 2015 2016/0030606, Feb. 4, 2016 U.S. Pat. No. 9,855,348, Jan. 2, 2018, Nick Devoogdt.
U.S. Appl. No. 15/742,161 2018/0200393, filed Jan. 5, 2018 Jul. 19, 2018, Tony Lahoutte.
U.S. Appl. No. 15/329,860 2018/0036442, filed Nov. 1, 2017 Feb. 8, 2018, Tony Lahoutte.
Chakravarty et al., "Nanobody: The "Magic Bullet" for Molecular Imaging?", Theranostics, 2014, 4(4): 386-398.
Debie et al., "Effect of Dye and Conjugation Chemistry on the Biodistribution Profile of Near-Infrared-Labeled Nanobodies as Tracers for Image-Guided Surgery", Mol Pharm., Apr. 3, 2017,14(4): 1145-1153.
Debie et al., "The Design and Preclinical Evaluation of a Single-Label Bimodal Nanobody Tracer for Image-Guided Surgery", Biomolecules, Feb. 26, 2021, 11(3):360.

(56) References Cited

OTHER PUBLICATIONS

Dekempeneer et al., "Labeling of Anti-HER2 Nanobodies with Astatine-211: Optimization and the Effect of Different Coupling Reagents on Their in Vivo Behavior", Mol Pharm., Aug. 5, 2019, 16(8): 3524-3533.

Dekempeneer et al., "Therapeutic Efficacy of (213) Bi-labeled sdAbs in a Preclinical Model of Ovarian Cancer", Mol Pharm., Sept. 8, 2020, 17(9): 3553-3566.

Devoogdt et al., "Molecular Imaging Using Nanobodies: A Case Study", Methods in Molecular Biology, 2012, vol. 911.

D'Huyvetter et al., "Radiolabeled nanobodies as theranostic tools in targeted radionuclide therapy of cancer", Expert Opin Drug Deliv., Dec. 2014, 11(12): 1939-1954.

D'Huyvetter et al., "$^{131}$I-labeled Anti-HER2 Camelid sdAb as a Theranostic Tool in Cancer Treatment", Clin Cancer Res., Nov. 1, 2017, 23(21): 6616-6628.

Goldstein et al., "Developments in single photon emission computed tomography and PET-based HER2 molecular imaging for breast cancer", Expert Rev Anticancer Then, Mar. 2013, 13(3): 359-373.

International Preliminary Report on Patentability corresponding to International Patent Application No. PCT/EP2015/067424, dated Jan. 31, 2017.

Massa et al., "Site-Specific Labeling of Cysteine-Tagged Camelid Single-Domain Antibody-Fragments for Use in Molecular Imaging", Bioconjg Chem., May 21, 2014, 25(5): 979-988.

Meng et al., "Molecular Imaging Probes for Diagnosis and Therapy Evaluation of Breast Cancer", Int'l Journal of Biomedical Imaging, 2013, Article ID 230487, pp. 1-14.

Muyldermans et al., "Identification of Camel-Derived Antibodies for Screening Breast Cancer Patients", 2012, pp. 29-31.

Patris et al., "Nanoimmunoassay onto a screen printed electrode for HER2 breast cancer biomarker determination", Talenta, Dec. 2014, 130: 164-170.

Pruszynski et al., (2018) "Evaluation of an Anti-HER2 Nanobody Labeled with $^{225}$Ac for Targeted α-Particle Therapy of Cancer", Mol Pharm., Apr. 2, 2018, 15(4): 1457-1466.

Puttemans et al., "Preclinical Targeted α- and β-Radionuclide Therapy in HER2-Positive Brain Metastasis Using Camelid Single-Domain Antibodies", Cancers (Basel), Apr. 21, 2020, 12(4): 1017.

Rahmim et al., "PET versus SPECT: strengths, limitations and challenges", Nuclear Medicine Communications, 2008, 29: 193-207.

Vaneycken et al., "Immuno-imaging using nanobodies", Curr Opin in Bio., 2011, 22(6): 877-881.

Vaneycken et al., "Synthesis and first in vivo evaluation of 18F-anti-HER2-Nanobodies: a new probe for PET imaging of HER2 expression in breast cancer", Journal of Nuclear Medicine, Apr. 2011, 52(4): 664.

Wang et al., "Antibody-Based Imaging of HER-2: Moving into the Clinic", Current Molecular Medicine, Dec. 2013, 13(10): 1523-1537.

Xavier et al., "F-nanobody for PET imaging of HER2 overexpressing tumors", Nuclear Medicine and Biology, 2016, 43: 247-252.

Zhou et al., "Fluorine-18 Labeling of the HER2-Targeting Single-Domain Antibody 2Rs15d Using a Residualizing Label and Preclinical Evaluation", Mol Imaging Biol., Dec. 2017, 19(6): 867-877.

Zhou et al., "An Efficient Method for Labeling Single Domain Antibody Fragments with (18)F Using Tetrazine- Trans-Cyclooctene Ligation and a Renal Brush Border Enzyme-Cleavable Linker", Bioconjug Chem., Dec. 19, 2018, 29(12): 4090-4103.

Zhou et al., "Fluorine-18 labeling of an anti-HER2 VHH using a residualizing prosthetic group via a strain-promoted click reaction: Chemistry and preliminary evaluation", Bioorg Med Chem., May 1, 2018, 26(8): 1939-1949.

Zhou et al., "Labeling Single Domain Antibody Fragments with Fluorine-18 Using 2,3,5,6-Tetrafluorophenyl 6-[$^{18}$F]Fluoronicotinate Resulting in High Tumor-to-Kidney Ratios", Mol Pharm, Jan. 7, 2019, 16(1): 214-226.

Fig. 1A
Fig. 1B
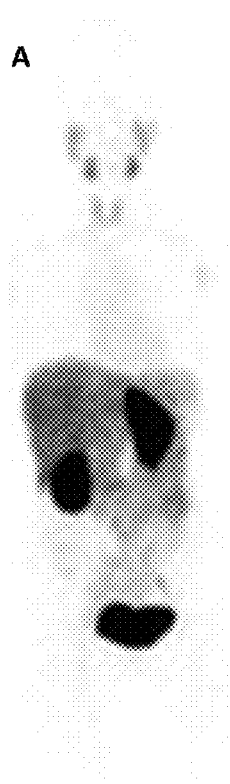
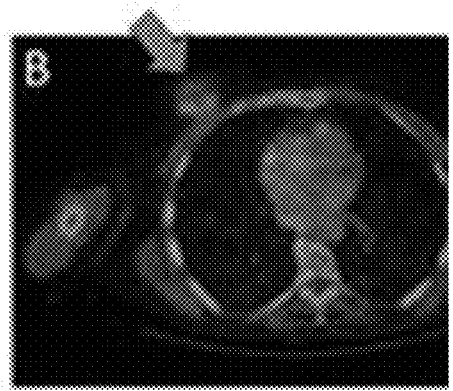
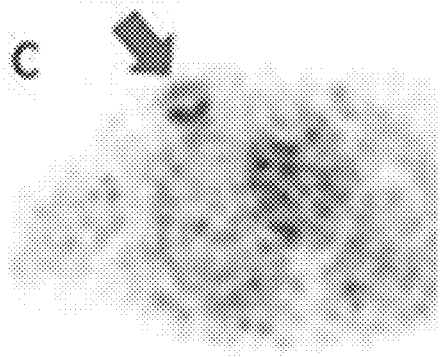
Fig. 1C 10 min    60 min    90 min Fig. 6A
Fig. 6B
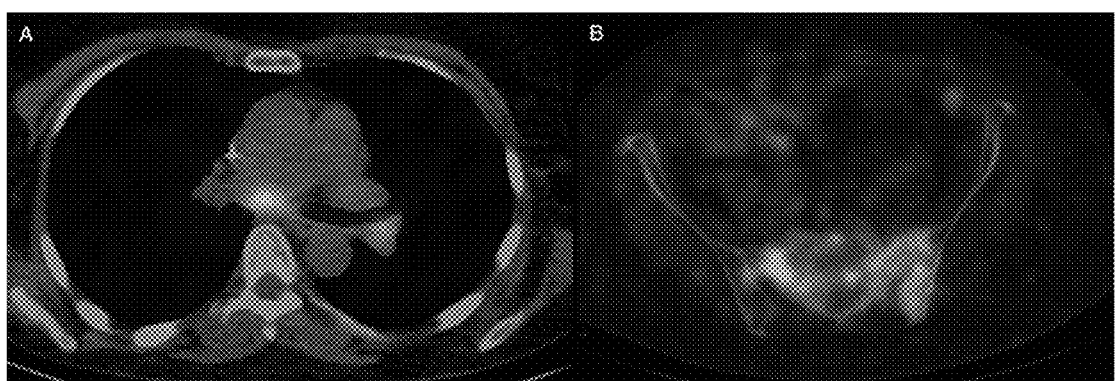
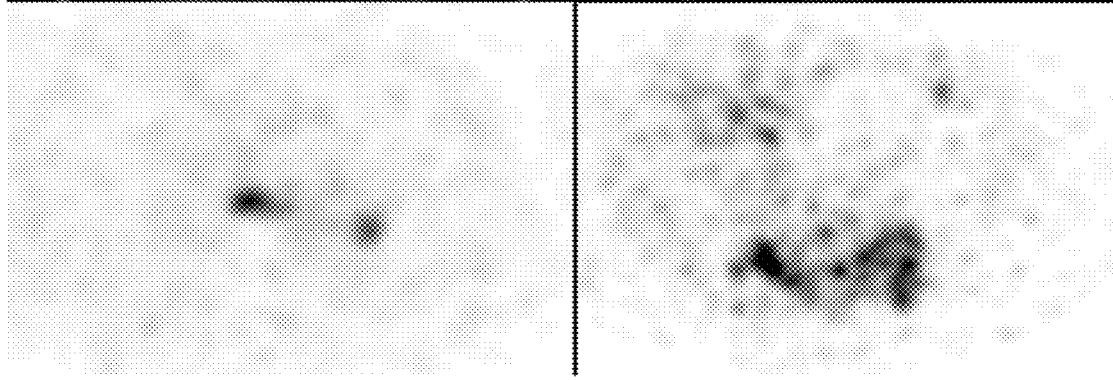

Fig. 7A
Fig. 7B
Fig. 7C
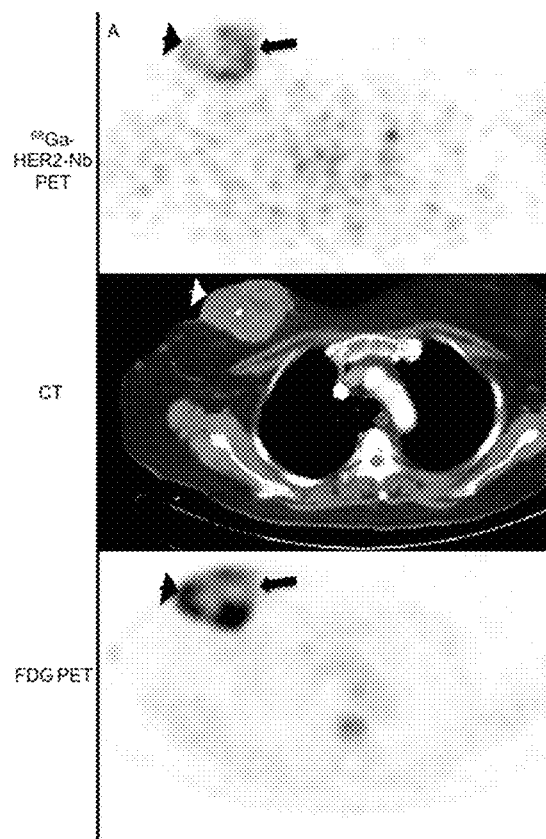
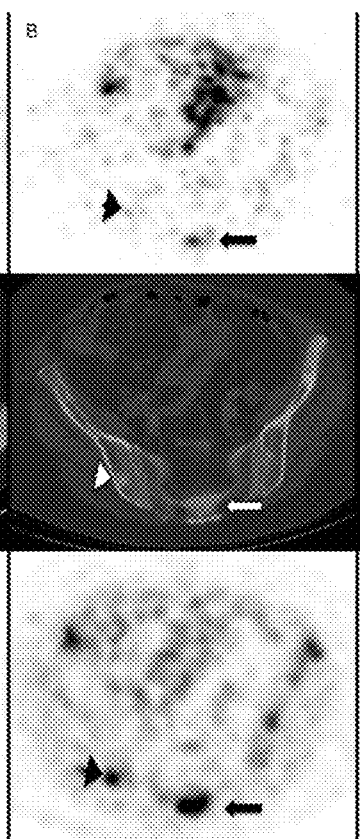
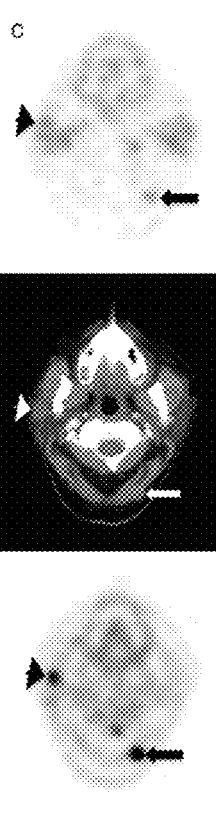

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: CDR1 sequence of VHH 2Rs15d

<400> SEQUENCE: 1

Gly Tyr Ile Phe Asn Ser Cys Gly
1               5

<210> SEQ ID NO 2
<211> LENGTH: 7
<212> TYPE: PRT
<213> ORGANISM: Artificial Sequence
<220> FEATURE:
<223> OTHER INFORMATION: CDR2 sequence of VHH 2Rs15d

<400> SEQUENCE: 2

Ile Ser Gly Asp Gly Asp Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CDR3 sequence of VHH 2Rs15d

<400> SEQUENCE: 3

Ala Val Cys Tyr Asn Leu Glu Thr Tyr
1               5
```

```
<210> SEQ ID NO 4
<211> LENGTH: 115
<212> TYPE: PRT
<213> ORGANISM: Artificial Sequence
<220> FEATURE:
<223> OTHER INFORMATION: VHH sequence

<400> SEQUENCE: 4

Gln Val Gln Leu Gln Glu Ser Gly Gly Gly Ser Val Gln Ala Gly Gly
1               5                   10                  15

Ser Leu Lys Leu Thr Cys Ala Ala Ser Gly Tyr Ile Phe Asn Ser Cys
            20                  25                  30

Gly Met Gly Trp Tyr Arg Gln Ser Pro Gly Arg Glu Arg Glu Leu Val
        35                  40                  45

Ser Arg Ile Ser Gly Asp Gly Asp Thr Trp His Lys Glu Ser Val Lys
    50                  55                  60

Gly Arg Phe Thr Ile Ser Gln Asp Asn Val Lys Lys Thr Leu Tyr Leu
65                  70                  75                  80

Gln Met Asn Ser Leu Lys Pro Glu Asp Thr Ala Val Tyr Phe Cys Ala
                85                  90                  95

Val Cys Tyr Asn Leu Glu Thr Tyr Trp Gly Gln Gly Thr Gln Val Thr
            100                 105                 110

Val Ser Ser
        115
```

RADIO-LABELLED ANTIBODY FRAGMENTS FOR USE IN THE PROGNOSIS, DIAGNOSIS OF CANCER AS WELL AS FOR THE PREDICTION OF CANCER THERAPY RESPONSE

RELATED APPLICATIONS

This application is a continuation of U.S. patent application Ser. No. 15/329,860, filed Nov. 1, 2017, which is a 35 U.S.C. § 371 filing of International Patent Application No. PCT/EP2015/067424, filed Jul. 29, 2015, which claims priority to European Patent Application No. 14178946.1, filed Jul. 29, 2014, each of which is incorporated herein by reference in its entirety.

FIELD OF THE INVENTION

The present invention relates to the field of radio-labelled antibody fragments and uses thereof for imaging, detection, diagnostic and/or prognostic purposes as well as for predicting patient response(s) to therapeutics. In particular, the present invention relates to radiolabelled antibody fragments for use in the prognosis and diagnosis of cancer as well as for the prediction of patient response(s) to cancer therapy.

BACKGROUND

Diagnosis of cancer at an early stage in cancer development is an important factor in improving the successful treatment of the cancer and in improving survival rates.

Because of the biological heterogeneity and the wide spectrum of responsiveness to different treatments of certain types of cancer, such as for instance breast cancer, cancer remains a complex disease of difficult clinical management.

Advances in the understanding of the molecular mechanisms leading to cancer have enabled the identification of surrogate markers. For instance, several circulating tumour markers have been investigated for clinical utility in breast cancer: Human Epidermal growth factor Receptor 2 (HER2), carcinoembryonic antigen (CEA); tissue polypeptide antigen (TPA), which is a soluble marker of keratin 18; gross cystic disease protein (GCDP); prostate specific antigen (PSA); and the products of the MUC-I gene. However, sensitivity levels for these markers have been found to be relatively low in early stage disease. Accordingly, the presently available tumour markers proposed for the early detection and diagnosis of cancer are few in number and many suffer from disadvantages such as low and heterogenous expression levels making early detection difficult and unreliable.

To date, the definitive diagnosis of most cancers is based on evaluation of tissue samples using the light microscope-optionally followed by immunohistochemistry of a tumor biopsy, which is both invasive and time-consuming.

While in situ hybridization assays offer an alternative for immunohistochemistry for the subtyping of certain cancers, these assays typically produce a substantial number of false negative results.

Accordingly, tools and methods allowing a more efficient and highly sensitive diagnosis of cancer and the correct determination of cancer subtypes, sometimes associated with important predictive information for therapy response, are of extreme importance for the early diagnosis of cancer and their optimal treatment so as to increase the chances of permanent recovery from this disease.

SUMMARY OF THE INVENTION

The present inventors have identified novel and improved antibody fragments which specifically bind to a target protein that is present on and/or specific for a solid tumor for use in the diagnosis and/or prognosis of cancer as well as the prediction of patient response to therapy.

In particular, through the radiolabelling of a specific type of antibody fragments, i.e. the heavy chain variable domains derived from heavy chain antibodies (hereinafter referred to as $V_{HH}$'S), which specifically interact with solid tumors, the present inventors have developed an improved and effective strategy for the early stage diagnosis of cancer, that is characterized by high tumor uptake values, low healthy tissue uptake values, and fast clearance from the blood.

The radiolabelled solid tumor binding antibody fragments or a functional fragment thereof as disclosed herein thus show several advantages over the traditional (immunoglobulin and non-immunoglobulin) tumor binding agents known in the art, including a higher potency and faster blood clearance of unbound probes, leading to (1) lower dosage forms and lower toxicity; and (2) the possibility to obtain sufficient contrast images at short time-points post injection. Also, because of their small size, the antibody fragments as disclosed herein have the ability to better penetrate into physiological compartments, tissues and organs, such as metastatic brain lesions, which are less accessible to other, larger polypeptides and proteins.

The present invention provides such radio-labelled antibody fragments, as well as polypeptides that comprise or essentially consist of one or more such radio-labelled antibody fragments and to uses of such radio-labelled antibody fragments or polypeptides for the accurate diagnosis of cancer.

In one aspect, the present invention provides radiolabelled heavy chain variable domains derived from heavy chain antibodies ($V_{HH}$'S) or functional fragments thereof, which specifically bind to a target protein that is present on and/or specific for a solid tumor (as defined herein) for use in a method for the diagnosis and/or prognosis of cancer in a subject, wherein said $V_{HH}$ or a functional fragment thereof has a calculated mean effective dose of between 0.002 and 0.1 mSv/MBq in said subject.

In certain embodiments, the present invention provides radiolabelled $V_{HH}$'s or functional fragments thereof for use in a method for the diagnosis and/or prognosis of cancer in a human subject, wherein said $V_{HH}$ or a functional fragment thereof has a calculated mean effective dose of between 0.002 and 0.1 mSv/MBq in said human subject.

In further particular embodiments, the present invention provides radiolabelled $V_{HH}$'s or functional fragments thereof for use in a method for the diagnosis and/or prognosis of cancer in a subject, wherein said $V_{HH}$ or a functional fragment thereof specifically binds to HER2.

In further particular embodiments, the present invention provides radiolabelled $V_{HH}$'s or functional fragments thereof for use in a method for the diagnosis and/or prognosis of cancer, which $V_{HH}$'s specifically bind to HER2 for use in a method for the diagnosis and/or prognosis of cancer in a subject, wherein said $V_{HH}$'s or functional fragments thereof do not compete with the monoclonal antibody Herceptin® (Trastuzumab) for binding to HER2, as determined using a suitable competition assay.

In still further particular embodiments, the present invention provides radiolabelled $V_{HH}$'s or functional fragments thereof for use in a method for the diagnosis and/or prognosis of cancer, which $V_{HH}$'s or functional fragments thereof specifically bind to said target protein that is present on and/or specific for a solid tumor with an affinity of less than 5 nM, such as between 1 and 5 nM, preferably between 2 and 3 nM.

In yet other particular embodiments, the present invention provides radiolabelled $V_{HH}$'s or functional fragments thereof for use in a method for the diagnosis and/or prognosis of cancer, which $V_{HH}$'s or functional fragments thereof are labelled with a radio-isotope chosen from the group consisting of 68Ga, 123I, 124I, 125I, 131I, 18F, 111In, 99mTc, 64Cu, 86Y, 76Br, 89Zr, 177Lu, 133Xe, 90Y, 201Tl, 82Rb, 209At, 210At, 211At, 209At, 210At and 211At, such as preferably but not limited to $V_{HH}$'s that are labelled with 68Ga.

In specific embodiments, the amino acid sequence of the radio-labelled $V_{HH}$'s as disclosed herein, which specifically interact with solid tumors, comprises the CDR combination: a CDR1 region having SEQ ID NO: 1, a CDR2 region having SEQ ID NO: 2, and a CDR3 region having SEQ ID NO: 3 or functional fragments thereof.

In further specific embodiments, the amino acid sequence of the radio-labelled $V_{HH}$'s as disclosed herein, which specifically interact with a solid tumor antigen, has at least 80% amino acid identity with the amino acid sequence of SEQ ID NO: 4, or functional fragments thereof.

In yet further specific embodiments, the amino acid sequence of the radio-labelled $V_{HH}$'s as disclosed herein, which specifically interact with a tumor-specific antigen, is identical with the amino acid sequence of SEQ ID NO: 4, or functional fragments thereof.

In certain embodiments, the present invention provides a radiolabelled $V_{HH}$ or functional fragments thereof as disclosed herein for use in the diagnosis and/or prognosis of cancer, wherein said cancer is breast cancer.

In certain other embodiments, diagnosis and/or prognosis of cancer is achieved by administering the radiolabelled $V_{HH}$'s or functional fragments thereof as disclosed herein to a subject in need thereof intravenously or intraperitoneally.

In further specific embodiments, the amino acid sequence of the radio-labelled $V_{HH}$'s or functional fragments thereof as disclosed herein, which specifically interact with a solid tumor antigen are present in a monovalent format. In particular, the present inventors have found that when the radio-labelled $V_{HH}$'s or functional fragments as disclosed herein are produced in a monovalent format, their in vivo half-life is shorter and their clearance from the blood is more rapid compared to the same radio-labelled $V_{HH}$'s or functional fragments in the context of a bi- or multivalent construct. Accordingly, in certain specific embodiments, the radio-labelled $V_{HH}$'s or functional fragments thereof as disclosed herein are produced or present in a monovalent format so as to limit as much as possible any potential side effects and/or radiation toxicity effects.

In a further aspect, the present invention provides polypeptides comprising at least one radiolabelled $V_{HH}$ or functional fragment thereof, which $V_{HH}$ or a functional fragment thereof specifically binds to a target protein present on and/or specific for a solid tumor, for use in a method for the diagnosis and/or prognosis of cancer in a subject, such as a human subject, wherein said $V_{HH}$ has a calculated mean effective dose of between 0.002 and 0.1 mSv/MBq in said subject.

In yet a further aspect, the present invention provides compositions comprising at least one radiolabelled $V_{HH}$ or a functional fragment thereof, which $V_{HH}$ or a functional fragment thereof specifically binds to a target protein present on and/or specific for a solid tumor, for use in a method for the diagnosis and/or prognosis of cancer in a subject, such as a human subject, wherein said $V_{HH}$ has a calculated mean effective dose of between 0.002 and 0.1 mSv/MBq in said subject.

In another aspect, the present invention provides radiolabelled heavy chain variable domains derived from heavy chain antibodies ($V_{HH}$'S) or functional fragments thereof, which specifically bind to HER2, for use in a method for the diagnosis of HER-2 positive cancer lesions in human subjects initially diagnosed to be HER-2 negative in a standard assay for identifying HER-2 positive cancer lesions.

In particular embodiments, these radiolabelled $V_{HH}$'s or functional fragments thereof, which specifically bind to HER2 for use in a method for the diagnosis of HER-2 positive cancer lesions in human subjects initially diagnosed to be HER-2 negative, do not compete with the monoclonal antibody Herceptin® (Trastuzumab) for binding to HER2, as determined using a suitable competition assay.

In further particular embodiments, these radiolabelled $V_{HH}$'s or functional fragments thereof specifically bind to HER2 for use in a method for the diagnosis of HER-2 positive metastatic cancer lesions in human subjects initially diagnosed to be HER-2 negative.

In yet further particular embodiments, the radiolabelled $V_{HH}$'s or functional fragments thereof specifically binding to HER2 for use in a method for the diagnosis of HER-2 positive metastatic cancer lesions in human subjects have a calculated mean effective dose of between 0.002 and 0.1 mSv/MBq in said human subject.

In still further particular embodiments, the present invention provides radiolabelled $V_{HH}$'s or functional fragments thereof for use in a method for the diagnosis of HER-2 positive metastatic cancer lesions in human subjects, wherein said $V_{HH}$'s or functional fragments thereof specifically binds to HER2 with an affinity of less than 5 nM, such as between 1 and 5 nM, preferably between 2 and 3 nM.

In certain particular embodiments, the present invention provides radiolabelled $V_{HH}$'s or functional fragments thereof for use in a method for the diagnosis of HER-2 positive metastatic cancer lesions in human subjects, wherein said $V_{HH}$ or a functional fragment thereof is labelled with a radio-isotope chosen from the group consisting of 68Ga, 123I, 124I, 125I, 131I, 18F, 111In, 99mTc, 64Cu, 86Y, 76Br, 89Zr, 177Lu, 133Xe, 90Y, 201Tl, 82Rb, 209At, 210At, 211At, 209At, 210At and 211At, preferably but not limited to 68Ga.

In particular embodiments, the amino acid sequence of the radiolabelled $V_{HH}$'s specifically binding to HER2 for use in a method for the diagnosis of HER-2 positive metastatic cancer lesions in human subjects, comprises the combination of:

a CDR1 region having SEQ ID NO: 1, a CDR2 region having SEQ ID NO: 2, and a CDR3 region having SEQ ID NO: 3, or functional fragments thereof.

In further particular embodiments, the radiolabelled $V_{HH}$'s specifically binding to HER2 for use in a method for the diagnosis of HER-2 positive metastatic cancer lesions in human subjects, have at least 80% amino acid identity with the amino acid sequence of SEQ ID NO: 4 and/or have an amino acid sequence with SEQ ID NO: 4, or functional fragments thereof.

In certain embodiments, the present invention provides a radiolabelled $V_{HH}$ or functional fragments thereof as disclosed herein for use in a method for the diagnosis of HER-2 positive metastatic cancer lesions in human subjects, wherein said cancer is breast cancer.

In certain other embodiments, diagnosis and/or prognosis of cancer is achieved by administering the radiolabelled $V_{HH}$'s or functional fragments thereof as disclosed herein to human subjects intravenously or intraperitoneally.

In further specific embodiments, the radio-labelled $V_{HH}$'s or functional fragments thereof as disclosed herein, for use in a method for the diagnosis of HER-2 positive metastatic cancer lesions in human subjects, are present in a monovalent format.

In a further aspect, the present invention provides polypeptides comprising at least one $V_{HH}$ or a functional fragment thereof, which specifically binds to HER2, for use in a method for the diagnosis of HER-2 positive cancer lesions in human subjects initially diagnosed to be HER-2 negative in a standard assay for identifying HER-2 positive cancer lesions.

In yet a further aspect, the present invention provides compositions comprising at least one $V_{HH}$ or a functional fragment thereof, which specifically binds to HER2, for use in a method for the diagnosis of HER-2 positive cancer lesions in human subjects initially diagnosed to be HER-2 negative in a standard assay for identifying HER-2 positive cancer lesions.

DETAILED DESCRIPTION OF THE INVENTION

Definitions

General Definitions

The present invention will be described with respect to particular embodiments but the invention is not limited thereto but only by the claims. Any reference signs in the claims shall not be construed as limiting the scope. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

As used herein, the singular forms 'a', 'an', and 'the' include both singular and plural referents unless the context clearly dictates otherwise.

The terms 'comprising', 'comprises' and 'comprised of' as used herein are synonymous with 'including', 'includes' or 'containing', 'contains', and are inclusive or open-ended and do not exclude additional, non-recited members, elements or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

As used herein, amino acid residues will be indicated either by their full name or according to the standard three-letter or one-letter amino acid code.

As used herein, the terms 'polypeptide', 'protein', 'peptide', and 'amino acid sequence' are used interchangeably, and refer to a polymeric form of amino acids of any length, which can include coded and non-coded amino acids, chemically or biochemically modified or derivatized amino acids, and polypeptides having modified peptide backbones.

As used herein, the terms 'nucleic acid molecule', 'polynucleotide', 'polynucleic acid', 'nucleic acid' are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term 'homology' denotes at least secondary structural similarity between two macromolecules, particularly between two polypeptides or polynucleotides, from same or different taxons, wherein said similarity is due to shared ancestry. Hence, the term 'homologues' denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two amino acid sequences, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Amino acid sequences and nucleic acid sequences are said to be 'exactly the same' if they have 100% sequence identity over their entire length.

The term 'affinity', as used herein, refers to the degree to which a polypeptide, in particular an immunoglobulin, such as an antibody, or an immunoglobulin fragment, such as a $V_{HH}$, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M, such as lower than $10^{-9}$ M.

The terms 'specifically bind' and 'specific binding', as used herein, generally refers to the ability of a polypeptide, in particular an immunoglobulin, such as an antibody, or an immunoglobulin fragment, such as a $V_{HH}$, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

Accordingly, an amino acid sequence, in particular an antibody fragment, such as a $V_{HH}$, as disclosed herein is said to 'specifically bind to' a particular target when that amino acid sequence has affinity for, specificity for and/or is specifically directed against that target (or for at least one part or fragment thereof).

An amino acid sequence, in particular an antibody fragment, such as a $V_{HH}$, as disclosed herein is said to be 'specific for a first target antigen of interest as opposed to a second target antigen of interest' when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be 'specific for' a first target antigen of interest as opposed to a second target antigen of interest, it may specifically bind to (as defined herein) the first target antigen of interest, but not to the second target antigen of interest.

The 'specificity' of an amino acid sequence, in particular an antibody fragment, such as a $V_{HH}$, or a functional fragment thereof as disclosed herein can be determined based on affinity and/or avidity. The 'affinity' of an amino acid sequence as disclosed herein is represented by the equilibrium constant for the dissociation of the amino acid sequence as disclosed herein and the target protein of interest to which it binds. The lower the KD value, the stronger the binding strength between the amino acid sequence as disclosed herein and the target protein of interest to which it binds. Alternatively, the affinity can also be expressed in terms of the affinity constant (KA), which corresponds to 1/KD. The binding affinity of an amino acid sequence as disclosed herein can be determined in a manner known to the skilled person, depending on the specific target protein of interest. The 'avidity' of an amino acid sequence as disclosed herein is the measure of the strength of binding between the amino acid sequence as disclosed herein and the pertinent target protein of interest. Avidity is related to both the affinity between a binding site on the target protein of interest and a binding site on the amino acid sequence as disclosed herein and the number of pertinent binding sites present on the amino acid sequence as disclosed herein. Typically, the amino acid sequences as disclosed herein will bind to a target protein of interest with a dissociation constant (KD) of less than about 1 micromolar (1 µM), and preferably less than about 1 nanomolar (1 nM) [i.e., with an association constant (KA) of about 1,000,000 per molar ($10^6$ $M^{-1}$, 1E6/M) or more and preferably about 1,000,000,000 per molar ($10^9$ $M^{-1}$, 1E9/M) or more]. A KD value greater than about 1 millimolar is generally considered to indicate non-binding or non-specific binding. It is generally known in the art that the KD can also be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or $M^{-1}$ s$^{-1}$). In particular, an amino acid sequence as disclosed herein will bind to the target protein of interest with a kOff ranging between 0.1 and 0.0001 s$^{-1}$ and/or a kOn ranging between 1,000 and 1,000,000 $M^{-1}$ s$^{-1}$. Binding affinities, kOff and kOn rates may be determined by means of methods known to the person skilled in the art, for example ELISA methods, isothermal titration calorimetry, surface plasmon resonance, fluorescence-activated cell sorting analysis, and the more.

An amino acid sequence, in particular an antibody fragment, such as a $V_{HH}$ or a functional fragment thereof, as disclosed herein is considered to be '(in) essentially isolated (form)' as used herein, when it has been extracted or purified from the host cell and/or medium in which it is produced.

In respect of the amino acid sequences, in particular an antibody fragments, such as a $V_{HH}$'s or a functional fragment thereof, as disclosed herein, the terms 'binding region', 'binding site' or 'interaction site' present on the amino acid sequences as disclosed herein shall herein have the meaning of a particular site, part, domain or stretch of amino acid residues present on the amino acid sequence as disclosed herein that is responsible for binding to a target molecule. Such binding region essentially consists of specific amino acid residues from the amino acid sequence as disclosed herein which are in contact with the target molecule.

The terms 'competing (with)', 'cross-blocking', 'cross-binding' and 'cross-inhibiting' as used interchangeably herein, generally refer to an amino acid sequence, in particular an antibody fragment, such as a $V_{HH}$ or a functional fragment thereof, as disclosed herein that can interfere with the binding of other amino acid sequence as disclosed herein to a target protein of interest, as measured using a suitable in vitro, cellular or in vivo assay. Thus, more particularly, 'competing (with)', 'cross-blocking', 'cross-binding' and 'cross-inhibiting' using amino acid sequence as disclosed herein may mean interfering with or competing with the binding of another amino acid sequence as disclosed herein with a target protein of interest, thereby reducing that binding by at least 10% but preferably at least 20%, for example by at least 50%, at least 60%, at least 70%, at least 80%, at least 90%, at least 95% or more, as measured using a suitable in vitro, cellular or in vivo assay, compared to the binding of that other amino acid sequence as disclosed herein with the target protein of interest but without using the 'cross-blocking' amino acid sequence as disclosed herein.

An amino acid sequence, in particular an antibody fragment, such as a $V_{HH}$ or a functional fragment thereof, as disclosed herein is said to show 'cross-reactivity' for two different target proteins of interest if it is specific for (as defined herein) both of these different target proteins of interest.

In cases where all of the two or more binding sites of amino acid sequence, in particular an antibody fragment, such as a $V_{HH}$ or a functional fragment thereof, as disclosed herein are directed against or specifically bind to the same site, determinant, part, domain or stretch of amino acid residues of the target of interest, the amino acid sequence as disclosed herein is said to be 'bivalent' (in the case of two binding sites on the amino acid sequence) or multivalent (in the case of more than two binding sites on the amino acid sequence), such as for example trivalent.

The term 'bi-specific' when referring to an amino acid sequence, in particular an antibody fragment, such as a $V_{HH}$, as disclosed herein implies that either a) two or more of the binding sites of an amino acid sequence as disclosed herein are directed against or specifically bind to the same target of interest but not to the same (i.e. to a different) site, determinant, part, domain or stretch of amino acid residues of that target, the amino acid sequence as disclosed herein is said to be 'bi-specific' (in the case of two binding sites on the amino acid sequence) or multispecific (in the case of more than two binding sites on the amino acid sequence) or b) two or more binding sites of an amino acid sequence as disclosed herein are directed against or specifically bind to different target molecules of interest. The term 'multispecific' is used in the case that more than two binding sites are present on the amino acid sequence as disclosed herein.

Accordingly, a 'bispecific' amino acid sequence or antibody fragment, such as a 'bispecific' $V_{HH}$ or a 'multispecific' amino acid sequence or antibody fragment, such as a 'multispecific' $V_{HH}$ as used herein, shall have the meaning of an amino acid sequence, in particular an antibody fragment, such as a $V_{HH}$, as disclosed herein comprising respectively two or at least two binding sites, wherein these two or more binding sites have a different binding specificity. Thus, an amino acid sequence, in particular an antibody fragment, such as a $V_{HH}$, as disclosed herein is considered 'bispecific' or 'multispecific' if respectively two or more than two different binding regions exist in the same, monomeric, amino acid sequence.

The 'half-life' of an amino acid sequence, in particular an antibody fragment, such as a $V_H$ or a functional fragment thereof $_H$, as disclosed herein can generally be defined as the time that is needed for the in vivo serum concentration of the amino acid sequence as disclosed herein to be reduced by 50%. The in vivo half-life of an amino acid sequence as disclosed herein can be determined in any manner known to the person skilled in the art, such as by pharmacokinetic analysis. As will be clear to the skilled person, the half-life can be expressed using parameters such as the t½-alpha, t½-beta and the area under the curve (AUC). An increased half-life in vivo is generally characterized by an increase in one or more and preferably in all three of the parameters t½-alpha, t½-beta and the area under the curve (AUC).

As used herein, the terms 'inhibiting', 'reducing' and/or 'preventing' may refer to (the use of) an amino acid sequence, in particular an antibody fragment, such as a $V_H$ H or a functional fragment thereof, as disclosed herein that specifically binds to a target antigen of interest and inhibits, reduces and/or prevents the interaction between that target antigen of interest, and its natural binding partner. The terms 'inhibiting', 'reducing' and/or 'preventing' may also refer to (the use of) an amino acid sequence, in particular an antibody fragment, such as a $V_{HH}$, as disclosed herein that specifically binds to a target antigen of interest and inhibits, reduces and/or prevents a biological activity of that target antigen of interest, as measured using a suitable in vitro, cellular or in vivo assay. Accordingly, 'inhibiting', 'reducing' and/or 'preventing' may also refer to (the use of) an amino acid sequence as disclosed herein that specifically binds to a target antigen of interest and inhibits, reduces and/or prevents one or more biological or physiological mechanisms, effects, responses, functions pathways or activities in which the target antigen of interest is involved. Such an action of the amino acid sequence as disclosed herein as an antagonist may be determined in any suitable manner and/or using any suitable (in vitro and usually cellular or in vivo) assay known in the art, depending on the target antigen of interest.

Thus, more particularly, 'inhibiting', 'reducing' and/or 'preventing' using amino acid sequence, in particular an antibody fragment, such as a $V_{HH}$ or a functional fragment thereof, as disclosed herein may mean either inhibiting, reducing and/or preventing the interaction between a target antigen of interest and its natural binding partner, or, inhibiting, reducing and/or preventing the activity of a target antigen of interest, or, inhibiting, reducing and/or preventing one or more biological or physiological mechanisms, effects, responses, functions pathways or activities in which the target antigen of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target antigen of interest in the same assay under the same conditions but without using the amino acid sequence as disclosed herein. In addition, 'inhibiting', 'reducing' and/or 'preventing' may also mean inducing a decrease in affinity, avidity, specificity and/or selectivity of a target antigen of interest for one or more of its natural binding partners and/or inducing a decrease in the sensitivity of the target antigen of interest for one or more conditions in the medium or surroundings in which the target antigen of interest is present (such as pH, ion strength, the presence of co-factors, etc.), compared to the same conditions but without the presence of the amino acid sequence as disclosed herein. In the context of the present invention, 'inhibiting', 'reducing' and/or 'preventing' may also involve allosteric inhibition, reduction and/or prevention of the activity of a target antigen of interest.

As used herein, the terms 'enhancing', 'increasing' and/or 'activating' may refer to (the use of) an amino acid sequence, in particular an antibody fragment, such as a $V_{HH}$, as disclosed herein that specifically binds to a target protein of interest and enhances, increases and/or activates the interaction between that target protein of interest, and its natural binding partner. The terms 'enhancing', 'increasing' and/or 'activating' may also refer to (the use of) an amino acid sequence, in particular an antibody fragment, such as a $V_{HH}$ or a functional fragment thereof, as disclosed herein that specifically binds to a target protein of interest and enhances, increases and/or activates a biological activity of that target protein of interest, as measured using a suitable in vitro, cellular or in vivo assay. Accordingly, 'enhancing', 'increasing' and/or 'activating' may also refer to (the use of) an amino acid sequence as disclosed herein that specifically binds to a target protein of interest and enhances, increases and/or activates one or more biological or physiological mechanisms, effects, responses, functions pathways or activities in which the target protein of interest is involved. Such an action of the amino acid sequence as disclosed herein as an agonist may be determined in any suitable manner and/or using any suitable (in vitro and usually cellular or in vivo) assay known in the art, depending on the target protein of interest.

The inhibiting or antagonizing activity or the enhancing or agonizing activity of an amino acid sequence, in particular an antibody fragment, such as a $V_{HH}$ or a functional fragment thereof, as disclosed herein may be reversible or irreversible, but for pharmaceutical and pharmacological applications will typically occur reversibly.

An amino acid sequence, in particular an antibody fragment, such as a $V_{HH}$ or a functional fragment thereof, as disclosed herein is considered to be '(in) essentially isolated (form)' as used herein, when it has been extracted or purified from the host cell and/or medium in which it is produced.

In respect of the amino acid sequences, in particular an antibody fragment, such as a $V_{HH}$ or a functional fragment thereof, as disclosed herein, the terms 'binding region', 'binding site' or 'interaction site' present on the amino acid sequences as disclosed herein shall herein have the meaning of a particular site, region, locus, part, or domain present on the target molecule, which particular site, region, locus, part, or domain is responsible for binding to that target molecule. Such binding region thus essentially consists of that particular site, region, locus, part, or domain of the target molecule, which is in contact with the amino acid sequence when bound to that target molecule.

As used herein, the term 'antibody' refers to polyclonal antibodies, monoclonal antibodies, humanized antibodies, single-chain antibodies, and fragments thereof such as Fab, F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term 'monoclonal antibody' refers to an antibody composition having a homogeneous antibody population. The term is not limited regarding the species or source of the antibody, nor is it intended to be limited by the manner in which it is made. The term encompasses whole immunoglobulins as well as fragments and others that retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term 'polyclonal antibody' refers to an antibody composition having a heterogeneous antibody population. Polyclonal antibodies are often derived from the pooled serum from immunized animals or from selected humans.

'Heavy chain variable domain of an antibody or a functional fragment thereof', as used herein, means (i) the variable domain of the heavy chain of a heavy chain antibody, which is naturally devoid of light chains (also indicated hereafter as $V_{HH}$), including but not limited to the variable domain of the heavy chain of heavy chain antibodies of camelids or sharks or (ii) the variable domain of the heavy chain of a conventional four-chain antibody (also indicated hereafter as $V_H$), including but not limited to a camelized (as further defined herein) variable domain of the heavy chain of a conventional four-chain antibody (also indicated hereafter as camelized $V_H$).

As further described hereinbelow, the amino acid sequence and structure of a heavy chain variable domain of an antibody can be considered, without however being limited thereto, to be comprised of four framework regions or 'FR's', which are referred to in the art and hereinbelow as 'framework region 1' or 'FR1'; as 'framework region 2' or 'FR2'; as 'framework region 3' or 'FR3'; and as 'framework region 4' or 'FR4', respectively, which framework regions are interrupted by three complementary determining regions or 'CDR's', which are referred to in the art as 'complementarity determining region 1' or 'CDR1'; as 'complementarity determining region 2' or 'CDR2'; and as 'complementarity determining region 3' or 'CDR3', respectively.

As used herein, the terms 'complementarity determining region' or 'CDR' within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains.

As also further described hereinbelow, the total number of amino acid residues in a heavy chain variable domain of an antibody (including a $V_{HH}$ or a $V_H$) can be in the region of 110-130, is preferably 112-115, and is most preferably 113. It should however be noted that parts, fragments or analogs of a heavy chain variable domain of an antibody are not particularly limited as to their length and/or size, as long as such parts, fragments or analogs retain (at least part of) the functional activity and/or retain (at least part of) the binding specificity of the original a heavy chain variable domain of an antibody from which these parts, fragments or analogs are derived from. Parts, fragments or analogs retaining (at least part of) the functional activity and/or retaining (at least part of) the binding specificity of the original heavy chain variable domain of an antibody from which these parts, fragments or analogs are derived from are also further referred to herein as 'functional fragments' of a heavy chain variable domain.

The amino acid residues of a variable domain of a heavy chain variable domain of an antibody (including a $V_{HH}$ or a $V_H$) are numbered according to the general numbering for heavy chain variable domains given by Kabat et al. ('Sequence of proteins of immunological interest', US Public Health Services, NIH Bethesda, Md., Publication No. 91), as applied to $V_{HH}$ domains from Camelids in the article of Riechmann and Muyldermans, referred to above (see for example FIG. 2 of said reference). According to this numbering, FR1 of a heavy chain variable domain comprises the amino acid residues at positions 1-30, CDR1 of a heavy chain variable domain comprises the amino acid residues at positions 31-35, FR2 of a heavy chain variable domain comprises the amino acids at positions 36-49, CDR2 of a heavy chain variable domain comprises the amino acid residues at positions 50-65, FR3 of a heavy chain variable domain comprises the amino acid residues at positions 66-94, CDR3 of a heavy chain variable domain comprises the amino acid residues at positions 95-102, and FR4 of a heavy chain variable domain comprises the amino acid residues at positions 103-113. [In this respect, it should be noted that—as is well known in the art for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of heavy chain variable domains are the method described by Chothia et al. (*Nature* 342, 877-883 (1989)), the so-called 'AbM definition' and the so-called 'contact definition'. However, in the present description, claims and figures, the numbering according to Kabat as applied to $V_{HH}$ domains by Riechmann and Muyldermans will be followed, unless indicated otherwise.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx NV; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx NV and the further published patent applications by Ablynx NV; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol. Immunol. 1997 November-December; 34(16-17): 1121-31; Atarhouch et al., Journal of Camel Practice and Research 1997; 4: 177-182; Nguyen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 Jul. 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol. Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat. Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul. 1; 52 (1): 47-50; Loris et al., Biol. Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol. Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9): 3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21.

Generally, it should be noted that the term 'heavy chain variable domain' as used herein in its broadest sense is not limited to a specific biological source or to a specific method of preparation. For example, as will be discussed in more detail below, the heavy chain variable domains derived from heavy chain antibodies (i.e. $V_{HH}$'s) as disclosed herein can be obtained (1) by isolating the $V_{HH}$ domain of a naturally occurring heavy chain antibody; (2) by expression of a nucleotide sequence encoding a naturally occurring $V_{HH}$ domain; (3) by 'camelization' (as described below) of a naturally occurring $V_H$ domain from any animal species, in particular a species of mammal, such as from a human being, or by expression of a nucleic acid encoding such a camelized $V_H$ domain; (4) by 'camelisation' of a 'domain antibody' or 'Dab' as described by Ward et al (supra), or by expression of a nucleic acid encoding such a camelized $V_H$ domain (5) using synthetic or semi-synthetic techniques for preparing proteins, polypeptides or other amino acid sequences; (6) by preparing a nucleic acid encoding a $V_{HH}$ using techniques for nucleic acid synthesis, followed by expression of the nucleic acid thus obtained; and/or (7) by any combination of the foregoing. Suitable methods and techniques for performing the foregoing will be clear to the skilled person based on the disclosure herein and for example include the methods and techniques described in more detail hereinbelow.

In the context of the invention the term VHH or VHH domain is used interchangeably with the term Nanobody (Nb).

All terms $^{68}$Ga-HER-Nanobody, $^{68}$Ga-NOTA-anti-HER2 Nanobody and $^{68}$Ga-anti-HER2-VHH on the one hand; HER-Nanobody, anti-HER2-Nanobody, HER2-VHH and anti-HER2-VHH on the other hand, refer to the same compound (either labelled with $^{68}$Ga or unlabeled).

The term 'effective amount', as used herein, means the amount needed to achieve the desired result or results.

As used herein, the terms 'determining', 'measuring', 'assessing', 'monitoring' and 'assaying' are used interchangeably and include both quantitative and qualitative determinations.

As used herein, the term 'prevention and/or treatment' comprises preventing and/or treating a certain disease and/or disorder, preventing the onset of a certain disease and/or disorder, slowing down or reversing the progress of a certain disease and/or disorder, preventing or slowing down the onset of one or more symptoms associated with a certain disease and/or disorder, reducing and/or alleviating one or more symptoms associated with a certain disease and/or disorder, reducing the severity and/or the duration of a certain disease and/or disorder, and generally any diagnostic effect of the amino acid sequences as disclosed herein that is beneficial to the subject or patient being treated.

As used herein, the terms 'diagnosis', 'prediction' and/or 'prognosis' as used herein comprises diagnosing, predicting and/or prognosing a certain disease and/or disorder, thereby predicting the onset and/or presence of a certain disease and/or disorder, and/or predicting the progress and/or duration of a certain disease and/or disorder, and/or predicting the response of a patient suffering from of a certain disease and/or disorder to therapy.

Invention-Related Definitions

As used herein, the terms 'solid tumor-specific antigen', 'tumor-specific antigen', 'tumor antigen', 'target protein present on and/or specific for a (solid) tumor', 'tumor-specific target (protein)", "tumor-associated antigen" are used interchangeably herein and include any protein which is present only on tumor cells and not on any other cell, or any protein, which is present on some tumor cells and also on some normal, healthy cells. Non-limiting examples of tumor antigens include tissue differentiation antigens, mutant protein antigens, oncogenic viral antigens, cancer-testis antigens and vascular or stromal specific antigens.

As used herein, the term 'radiolabelled' as in 'radiolabelled' amino acid sequence, 'radiolabelled' antibody fragment or 'radiolabelled' $V_{HH}$ refers to the radioisotopic labeling of that amino acid sequence, antibody fragment or $V_{HH}$, wherein the amino acid sequence, antibody fragment or $V_{HH}$ is labelled by including, coupling, or chemically linking a radionuclide to its amino acid sequence structure.

As used herein, the terms 'radionuclide', 'radioactive nuclide', 'radioisotope' or 'radioactive isotope', are used interchangeably herein and refer to atoms with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles. These emissions constitute ionizing radiation. Radionuclides occur naturally, or can be produced artificially.

By "solid tumor(s)" or "tumor(s)" are meant primary tumors and/or metastases (wherever located) such as but not limited to gliomas, pancreatic tumors; lung cancer, e.g. small cell lung cancer, breast cancer; epidermoid carcinomas; neuroendocrine tumors; gynaecological and urological cancer, e.g. cervical, uterine, ovarian, prostate, renal-cell carcinomas, testicular germ cell tumors or cancer; pancreas cancer (pancreatic adenocarcinoma); glioblastomas; head and/or neck cancer; CNS (central nervous system) cancer; bones tumors; solid pediatric tumors; haematological malignancies; AIDS-related cancer; soft-tissue sarcomas, and skin cancer, including melanoma and Kaposi's sarcoma.

A 'lesion' as used herein can refer to any abnormal change in a body tissue or organ resulting from injury or disease. In cancer terminology, lesion typically refers to a tumor.

As used herein, the term 'HER-2 positive' as in 'HER-2 positive (cancer) lesions', 'HER-2 positive (breast) cancer', or 'HER-2 positive tumor' refers to cancerous or malignant cells or tissue characterized by HER2 gene amplification or HER2 protein overexpression and thus have abnormally high levels of the HER2 gene and/or the HER2 protein compared to normal healthy cells. HER-2 positive breast cancer is characterized by cancerous breast cells characterized by HER2 gene amplification or HER2 protein overexpression. In about 1 of every 5 breast cancers, the cancer cells make an excess of HER2, mainly caused by HER2 gene amplification due to one or more gene mutations. The elevated levels of HER2 protein that it causes can occur in many types of cancer—and are thus not limited to breast cancer.

As used herein, the term 'HER-2 negative' as in as in 'HER-2 negative (cancer) lesions', 'HER-2 negative (breast) cancer', 'HER-2 negative tumor', 'HER-2 negative cell(s)' can refer either to cancerous or malignant cells or tissue or to normal healthy cells or tissue, both of which are characterized by the absence of HER2 gene amplification or HER2 protein overexpression and thus by normal levels of the HER2 gene and/or the HER2 protein.

The term 'in situ hybridization (ISH)' as used herein refers to a type of hybridization assay that uses a labeled complementary DNA or RNA strand (i.e., probe) to localize a specific DNA or RNA sequence in a portion or section of tissue (in situ), or, if the tissue is small enough (e.g. plant seeds, Drosophila embryos), in the entire tissue (whole mount ISH), in cells and in circulating tumor cells (CTCs). In situ hybridization is a powerful technique for identifying specific mRNA species within individual cells in tissue sections, providing insights into physiological processes and disease pathogenesis. In particular, situ hybridization is used to reveal the location of specific nucleic acids sequences on chromosomes or in tissues, a crucial step for understanding the organization, regulation and function of genes. The key techniques currently in use include: in situ hybridization to mRNA with oligonucleotide and RNA probes (both radio labelled and hapten labelled); analysis with light and electron microscopes; whole mount in situ hybridization; double detection of RNAs and RNA plus protein; and fluorescent in situ hybridization to detect chromosomal sequences. DNA ISH can be used to determine the structure of chromosomes. Fluorescent DNA ISH (FISH) can, for example, be used in medical diagnostics to assess chromosomal integrity. RNA ISH (RNA in situ hybridization) is used to measure and localize RNAs (mRNAs, lncRNAs and miRNAs) within tissue sections, cells, whole mounts, and circulating tumor cells (CTCs).

The term 'fluorescence in situ hybridization (FISH)' as used herein refers to a specific type of in situ hybridization assay that is used to detect and localize the presence or absence of specific DNA sequences on chromosomes. FISH uses fluorescent probes that bind to only those parts of the chromosome with which they show a high degree of sequence complementarity. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues.

The term 'immunohistochemistry (IHC)' as used herein refers to the process of detecting antigens (e.g., proteins) in cells of a tissue section by exploiting the principle of antibodies binding specifically to antigens in sections of biological tissues. Immunohistochemical staining is widely used in the diagnosis of abnormal cells such as those found in cancerous tumors. IHC is also widely used in basic research to understand the distribution and localization of biomarkers and differentially expressed proteins in different parts of a biological tissue. 'Trastuzumab' (Trade names: Herclon®, Herceptin®) is a monoclonal antibody that interferes with the HER2/neu receptor. Its main use is to treat certain breast cancers.

The term 'primary tumor(s)' as used herein is a tumor growing at the anatomical site where tumor progression began and proceeded to yield a cancerous mass.

The term 'metastatic lesion(s)' as used herein refers to malignant, or cancerous, tumors that have spread from their original location to other parts of the body. Related medical terms that might be used interchangeably include late-stage cancer, advanced cancer, or metastatic disease. In general, metastatic lesions are considered to be incurable, although treatment is often available to control the spread of cancerous cells and potentially increase the individual's life expectancy.

Metastasis is the term for the spread of cancer beyond its originating site in the body. Thus, metastatic lesions are cancerous tumors that are found in locations apart from the original starting point of the primary tumor. Metastatic tumors occur when cells from the primary tumor break off and travel to distant parts of the body via the lymph system and blood stream. Alternately, cells from the original tumor could seed into new tumors at adjacent organs or tissues.

'Metastatic disease' as used herein refers to late-stage cancer and to the medical classification of cancer as being in stage Ill, when cancer cells are found in lymph nodes near the original tumor, or in stage IV, when cancer cells have traveled far beyond the primary tumor site to distant parts of the body. Metastatic lesions are most commonly found in the brain, lungs, liver, or bones. An individual with metastatic cancer might or might not experience any symptoms, and the symptoms could be related to the area where metastasized cells have relocated. Once metastatic lesions are present in the body, the individual's cancer will be considered incurable for most cancer types. This means it is excessively difficult to eradicate every existing cancer cell with available treatments. In this case, the goal of treatment becomes slowing the growth of tumors to maintain the highest possible quality of life and potentially extend the individual's life expectancy. In some cases, people with metastatic lesions can live for a number of years with appropriate treatment for symptom management.

The '(calculated mean) effective dose' of radiation within a subject as used herein refers to the tissue-weighted sum of the equivalent doses in all specified tissues and organs of the body and represents the stochastic health risk, which the probability of cancer induction and genetic effects of ionizing radiation delivered to those body parts. It takes into account the type of radiation and the nature of each organ or tissue being irradiated. It is the central quantity for dose limitation in radiological protection in the international system of radiological protection devised by the International Commission on Radiological Protection (ICRP). The SI unit for effective dose is the sievert (Sv) which is one joule/kilogram (J/kg). The effective dose replaced the former "effective dose equivalent" in 1991 in the ICRP system of dose quantities. For procedures using radiopharmaceuticals, the effective dose is typically expressed per unit of injected activity, i.e. expressed in mSv/MBq. The effective dose for the individual patient will then depend upon the injected activity of the radiopharmaceutical, expressed in MBq, and the calculated mean effective dose, expressed in mSv/MBq.

The effective dose for radiopharmaceuticals is calculated using OLINDA/EXM® software that was approved in 2004 by the FDA. The OLINDA/EXM® personal computer code performs dose calculations and kinetic modeling for radiopharmaceuticals (OLINDA/EXM stands for Organ Level INternal Dose Assessment/EXponential Modeling). OLINDA® calculates radiation doses to different organs of the body from systemically administered radiopharmaceuticals and performs regression analysis on user-supplied biokinetic data to support such calculations for nuclear medicine drugs. These calculations are used to perform risk/benefit evaluations of the use of such pharmaceuticals in diagnostic and therapeutic applications in nuclear medicine. The technology employs a number of standard body models for adults, children, pregnant women and others, that are widely accepted and used in the internal dose community. The calculations are useful to pharmaceutical industry developers, nuclear medicine professionals, educators, regulators, researchers and others who study the accepted radiation doses that should be delivered when radioactive drugs are given to patients or research subjects.

The calculated effective dose depends on the chosen standard body model and the chosen voiding bladder model.

The values provided herein have been calculated using the female adult model and a voiding bladder interval of 1 h.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Body of Description

The present inventors have identified tumor-binding antibody fragments, more particularly $V_{HH}$'S or functional fragments thereof, specifically interacting with an antigen that is specific for solid tumors for use in the diagnosis and/or prognosis and/or prediction of response to therapy of cancer. Additionally and more importantly, by radiolabelling the $V_{HH}$'s or functional fragments thereof as disclosed herein, an improved and effective method for the early-stage diagnosis of cancer has been developed, resulting in high tumor uptake values, low healthy tissue uptake values, and fast clearance from the blood and healthy tissues in a subject in need thereof, and in particular in human patients in need thereof.

Thus, the radio-labelled $V_{HH}$'s or functional fragments thereof as disclosed herein not only show a high sensitivity in the detection of cancerous cells but also, through their low uptake by normal healthy tissues and their fast clearance, a low toxicity effect and therefore much less side effects in patients compared to traditional or known diagnostic imaging agents for determining cancerous diseases.

Accordingly, through their high specificity and thus their high sensitivity for tumor cells, the antibody fragments as disclosed herein suggest a potential for either a lower dosage and/or a more accurate detection at the same dose, implying a reduction of unwanted side-effects and reduced toxicity, compared to known diagnostic imaging agents for determining cancer.

The present invention hereby demonstrates for the first time that radio-labelled antibody fragments, and in particular radiolabelled $V_{HH}$'s or functional fragments thereof, can be used at an extremely low dose to diagnose or make a prognosis for cancer and/or predicting the response to cancer therapy, in particular at an early stage, in an animal or human suffering from that cancer.

In particular, the present inventors have found that the radio-labelled antibody fragments, and in particular radio-labelled $V_{HH}$'s or functional fragments thereof, can be used to effectively diagnose cancer and/or make an accurate prognosis of that cancer in an animal or human suffering from that cancer, at a calculated mean effective dose as low as between 0.002 and 0.1 mSv/MBq in said animal or human subject.

In addition, because of their extremely high specificity for tumor cells, a certain class of the radiolabelled VHH's or functional fragments thereof as disclosed herein, have been found to be particularly suitable tools for detecting and diagnosing and/or make a prognosis for certain types of cancers as well as predict the therapy response for certain types of cancers, which cannot be easily and/or unambiguously detected using the currently available assays for such cancer types. More specifically, the present inventors have found that the radio-labelled antibody fragments, and in particular radiolabelled $V_{HH}$'s or functional fragments thereof as disclosed herein that are directed against the tumor-specific antigen HER2, can be used to effectively diagnose HER-2 positive cancer (lesions) and/or make an accurate prognosis of HER-2 positive cancer (lesions) in an animal or human, which was initially diagnosed to be HER-2 negative using one or more standard available assays for diagnosing HER-2 positive cancer (lesions). The importance of HER2 as a prognostic, predictive, and therapeutic marker for certain types of cancer, and in particular, for invasive breast cancer, is well recognized, and therefore, it is critical to have accurate testing tools and techniques in order to be able to make a correct assessment of the HER2 status. Unfortunately, however, there are significant contradictions and ambiguities among results coming from the different known tests that are available to date. With the radiolabeled $V_{HH}$'s or functional fragments thereof specifically directed against HER2, the present invention therefore meets the high need for reproducible, high-throughput and highly sensitive diagnostic tools and assays for the accurate and correct diagnosis and/or prognosis of HER-2 related cancers.

The radiolabelled antibody fragments or functional fragments thereof disclosed herein can be derived from a naturally occurring polypeptide, or alternatively they can be entirely artificially designed. Non-limiting examples of such naturally occurring polypeptides include heavy chain antibodies (hcAb), such as but not limited to camelid heavy chain antibodies.

In particular, the heavy chain variable domains derived from heavy chain antibodies (i.e. the $V_{HH}$'S) as disclosed herein consist of a single polypeptide chain and are not post-translationally modified. More particularly, the $V_{HH}$'s disclosed herein are derived from an innate or adaptive immune system, preferably from a protein of an innate or adaptive immune system. Still more particularly, the $V_{HH}$'s disclosed herein comprise 4 framework regions and 3 complementary determining regions, or any suitable fragment thereof (which will then usually contain at least some of the amino acid residues that form at least one of the complementary determining regions). In particular, the $V_{HH}$'s disclosed herein are easy to produce at high yield, preferably in a microbial recombinant expression system, and convenient to isolate and/or purify subsequently.

According to particular embodiments, the invention provides a number of stretches of amino acid residues (i.e. small peptides) that are particularly suited for binding to a tumor antigen, such as but not limited to HER2.

These stretches of amino acid residues may be present in, and/or may be incorporated into, the VHH's as disclosed herein, in particular in such a way that they form (part of) the antigen binding site of that $V_{HH}$. As these stretches of amino acid residues were first generated as CDR sequences of antibodies (or may be based on and/or derived from such CDR sequences, as further described herein), they will also generally be referred to herein as 'CDR sequences' (i.e. as CDR1 sequences, CDR2 sequences and CDR3 sequences, respectively). It should however be noted that the invention in its broadest sense is not limited to a specific structural role or function that these stretches of amino acid residues may have in the heavy chain variable domains as disclosed herein, as long as these stretches of amino acid residues allow the variable domains as disclosed herein to specifically bind to a tumor antigen. Thus, generally, the invention in its broadest sense relates to radiolabelled $V_{HH}$'s for use in the diagnosis and/or prognosis of cancer (by detection through imaging) as well as for predicting the cancer therapy response, which $V_{HH}$'s comprise a combination of CDR sequences as described herein and are specifically directed to a tumor-specific target protein. In specific but non-limiting embodiments hereof, the tumor-specific target protein is HER2.

Thus, in particular, but non-limiting embodiments, the $V_{HH}$'s as disclosed herein comprise at least one amino acid sequence that is chosen from the group consisting of the CDR1 sequences, CDR2 sequences and CDR3 sequences that are described herein. In particular, the $V_{HH}$'s as disclosed herein may comprise at least one antigen binding site, wherein said antigen binding site comprises at least one combination of a CDR1 sequence, a CDR2 sequence and a CDR3 sequence that are described herein.

Any $V_{HH}$ antibody fragment as disclosed herein and having one these CDR sequence combinations is preferably such that it can specifically bind (as defined herein) to a tumor-specific antigen, and more in particular such that it specifically binds to a tumor-specific antigen, in particular with dissociation constant (Kd) of $10^{-8}$ moles/liter or less, such as $10^{-9}$ moles/L or less, such as $0.5 \cdot 10^{-9}$ moles/L or less, such as $10^{-10}$ moles/L or less of said variable domain in solution.

In particular embodiments, the $V_{HH}$ antibody fragments against HER2 as disclosed herein are such that they can specifically bind to HER2 with dissociation constant (Kd) of between 1 to 5 nM.

Specific binding of a $V_{HH}$ tumor antigen can be determined in any suitable manner known per se, including, for example biopanning, Scatchard analysis and/or competitive binding assays, such as radioimmunoassays (RIA), enzyme immunoassays (EIA) and sandwich competition assays, and the different variants thereof known in the art.

In further particular embodiments, the $V_{HH}$'s as disclosed herein comprise the following combination of CDR sequences:

a CDR1 region having SEQ ID NO: 1, a CDR2 region having has SEQ ID NO: 2, and a CDR3 region having SEQ ID NO: 3.

Thus, in particular embodiments, the present invention provides heavy chain variable domains derived from heavy chain antibodies with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and are as further defined herein.

SEQ ID NO: 4 (see Table 1) gives the amino acid sequence of a heavy chain variable domain that has been raised against a tumor-specific antigen, in particular against HER2.

TABLE 1

VHH sequences

| Name | SEQ ID VHH | Amino acid sequence |
|---|---|---|
| 2Rs15d | 4 | QVQLQESGGGSVQAGGSLKLTCAASGYIFNSCGMGWYRQS PGRERELVSRISGDGDTWHKESVKGRFTISQDNVKKTLYL QMNSLKPEDTAVYFCAVCYNLETYWGQGTQVTVSS |

In particular, the invention in some specific embodiments provides radiolabelled $V_{HH}$ domains directed against a tumor-specific target antigen, which have at least 80%, preferably at least 85%, such as 90% or 95% or more sequence identity with the heavy chain variable domain of SEQ ID NO: 4 (see Table 1), and nucleic acid sequences that encode such heavy chain variable domain.

Some particularly preferred heavy chain variable domain sequences as disclosed herein are those which can bind to and/or are directed against HER2 and which have at least 90% amino acid identity with the heavy chain variable domain of SEQ ID NO: 4 (see Table 1), in which for the purposes of determining the degree of amino acid identity, the amino acid residues that form the CDR sequences are disregarded.

In these heavy chain variable domains, the CDR sequences (see Table 2) are generally as further defined herein.

TABLE 2

Specific combinations of CDR sequences (CDR sequences identified using IMGT numbering)

| Name | CDR1 sequence | SEQ ID | CDR2 sequence | SEQ ID | CDR3 sequence | SEQ ID |
|---|---|---|---|---|---|---|
| 2Rs15d | GYIFNSCG | 1 | ISGDGDT | 2 | AVCYNLETY | 3 |

It should be noted that the invention is not limited as to the origin of the $V_{HH}$ fragments disclosed herein (or of the nucleotide sequences to express these), nor as to the way that the $V_{HH}$ fragments or nucleotide sequences disclosed herein are (or have been) generated or obtained. Thus, the $V_{HH}$ fragments disclosed herein may be naturally occurring amino acid sequences (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" immunoglobulin sequences (such as partially or fully humanized mouse or rabbit immunoglobulin sequences, and in particular partially or fully humanized $V_{HH}$ sequences), "camelized" immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Also, a $V_{HH}$ sequence as disclosed herein may be suitably humanized, as further described herein, so as to provide one or more further (partially or fully) humanized amino acid sequences of the invention. Similarly, when an amino acid sequence comprises a synthetic or semi-synthetic sequence (such as a partially humanized sequence), said sequence may optionally be further suitably humanized, again as described herein, so as to provide one or more further (partially or fully) humanized amino acid sequences as disclosed herein.

In particular, humanized amino acid sequences may be amino acid sequences in which at least one amino acid residue is present (and in particular, in at least one of the framework residues) that is and/or that corresponds to a humanizing substitution. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled.

In order to be suitable for the medical purposes as disclosed herein, and in particular for the diagnostic and/or prognostic and/or predictive applications in cancer as disclosed herein, in which it is intended to specifically detect a tumor cell (preferably by imaging) that expresses the tumor-specific antigen against which the $V_{HH}$'s as disclosed herein are directed against, the $V_{HH}$'s are linked to or coupled to, such as chemically coupled to, a radionuclide.

Examples of suitable radionuclides which can be linked to a $V_{HH}$ or functional fragments thereof as disclosed herein in order to provide a compound for the diagnosis and/or prognosis of cancer and/or prediction of response to cancer therapy will be clear to the skilled person and can for example without any limitation be chosen from the group consisting of group consisting of 68Ga, 123I, 124I, 125I, 131I, 18F, 111In, 99mTc, 64Cu, 86Y, 76Br, 89Zr, 177Lu, 133Xe, 90Y, 201Tl, 82Rb, 209At, 210At, 211At, 209At, 210At and 211At. In particular embodiments, the radiolabelled $V_{HH}$'s as disclosed herein are labelled with Gallium-68.

Thus, in one aspect, the present invention provides radiolabelled $V_{HH}$ sequences or functional fragments thereof, specifically directed against a tumor antigen, which can be used to effectively diagnose cancer and/or make an accurate prognosis of that cancer in an animal or human suffering from that cancer and/or make an accurate prediction of the patient's response to a cancer therapy, at a calculated mean effective dose as low as between 0.002 and 0.1 mSv/MBq in said animal or human subject.

In particular embodiments, the present invention provides radiolabelled $V_{HH}$ sequences or functional fragments thereof, specifically directed against a tumor antigen for use in the diagnosis and/or prognosis of cancer and/or for the prediction of the patient's response to a cancer therapy at a calculated mean effective dose as low as between 0.002 and 0.1 mSv/MBq in an animal or human subject suffering from breast cancer.

In particular embodiments, the present invention provides radiolabelled $V_{HH}$ sequences specifically directed against a tumor antigen for use in the diagnosis and/or prognosis of cancer and/or for the prediction of the patient's response to a cancer therapy at a calculated mean effective dose as low as between 0.002 and 0.1 mSv/MBq in an animal or human subject suffering from that cancer, wherein the radiolabelled $V_{HH}$ sequences have an amino acid sequence, which has at least 80%, preferably at least 85%, such as 90% or 95% or more sequence identity with SEQ ID NO: 4 or functional fragments thereof.

In further particular embodiments, the present invention provides radiolabelled $V_{HH}$ sequences specifically directed against a tumor antigen for use in the diagnosis and/or prognosis of cancer and/or for the prediction of the patient's response to a cancer therapy at a calculated mean effective dose as low as between 0.002 and 0.1 mSv/MBq in an animal or human subject suffering from that cancer, wherein the radiolabelled $V_{HH}$ sequences have an amino acid sequence with SEQ ID NO: 4 or functional fragments thereof.

In further particular embodiments, the present invention provides 68Ga-labelled $V_{HH}$ sequences specifically or functional fragments thereof, directed against a tumor antigen for use in the diagnosis and/or prognosis of cancer and/or for the prediction of the patient's response to a cancer therapy at a calculated mean effective dose as low as between 0.002 and 0.1 mSv/MBq in an animal or human subject suffering from that cancer.

In particular embodiments, the 68Ga-labelled $V_{HH}$ sequence or functional fragments thereof, specifically directed against a tumor antigen are for use in the diagnosis and/or prognosis of breast cancer and/or for the prediction of the patient's response to breast cancer therapy at a calculated mean effective dose as low as between 0.002 and 0.1 mSv/MBq in an animal or human subject suffering from that cancer.

In further particular embodiments, the present invention provides 68Ga-labelled $V_{HH}$ sequences specifically directed against a tumor antigen for use in the diagnosis and/or prognosis of cancer and/or for the prediction of the patient's response to a cancer therapy at a calculated mean effective dose as low as between 0.002 and 0.1 mSv/MBq in an animal or human subject suffering from that cancer, wherein the radiolabelled $V_{HH}$ sequences have at least 80%, preferably at least 85%, such as 90% or 95% or more sequence identity with SEQ ID NO: 4, or functional fragments thereof In further particular embodiments, the present invention provides 68Ga-labelled $V_{HH}$ sequences specifically directed against a tumor antigen for use in the diagnosis and/or prognosis of cancer and/or for the prediction of the patient's response to a cancer therapy at a calculated mean effective dose as low as between 0.002 and 0.1 mSv/MBq in an animal or human subject suffering from that cancer, wherein the radiolabelled $V_{HH}$ sequences have an amino acid sequence with SEQ ID NO: 4, or functional fragments thereof.

In yet further particular embodiments, the present invention provides 68Ga-labelled $V_{HH}$ specifically directed against a tumor antigen having an amino acid sequence, which has at least 80%, preferably at least 85%, such as 90% or 95% or more sequence identity with SEQ ID NO: 4 or functional fragments thereof, for use in the diagnosis and/or prognosis of breast cancer and/or for the prediction of the patient's response to a breast cancer therapy at a calculated mean effective dose as low as between 0.002 and 0.1 mSv/MBq.

In yet further particular embodiments, the present invention provides 68Ga-labelled $V_{HH}$ sequences or functional fragments thereof, specifically directed against a tumor antigen having SEQ ID NO: 4 for use in the diagnosis and/or prognosis of breast cancer and/or for the prediction of the patient's response to a breast cancer therapy at a calculated mean effective dose as low as between 0.002 and 0.1 mSv/MBq.

In particularly preferred embodiments, the present invention provides the $V_{HH}$ domains as disclosed herein in their monomeric form as well as polypeptides and pharmaceutical compositions comprising a $V_{HH}$ domain in its monomeric form, i.e. comprising only one $V_{HH}$ domain so as to minimize the in vivo half-life of said polypeptides and pharmaceutical compositions as much as possible thereby reducing potential unwanted side effects and toxicity issues.

Variants of Heavy Chain Variable Domain Sequences

In certain aspects, the radiolabelled $V_{HH}$ domains or functional fragments thereof specifically binding to a tumor-specific antigen as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the heavy chain variable domains as disclosed herein and may or may not modify the properties of the heavy chain variable domain as disclosed herein. Such groups, residues, moieties or binding units may also for example be chemical groups which can be biologically active.

These groups, moieties or residues are, in particular embodiments, linked N- or C-terminally to the heavy chain variable domain, in particularly C-terminally linked.

In particular embodiments, the radiolabelled $V_{HH}$ domains or functional fragments thereof specifically binding to a tumor-specific antigen as disclosed herein may also have been chemically modified. For example, such a modification may involve the introduction or linkage of one or more functional groups, residues or moieties into or onto the heavy chain variable domain. These groups, residues or moieties may confer one or more desired properties or functionalities to the heavy chain variable domain. Examples of such functional groups will be clear to the skilled person.

For example, the introduction or linkage of such functional groups to a heavy chain variable domain or functional fragments thereof can result in an increase in the solubility and/or the stability of the heavy chain variable domain, in a reduction of the toxicity of the heavy chain variable domain, or in the elimination or attenuation of any undesirable side effects of the heavy chain variable domain, and/or in other advantageous properties.

In particular embodiments, the one or more groups, residues, moieties are linked to the heavy chain variable domain or functional fragments thereof via one or more suitable linkers or spacers.

While the radiolabelled $V_{HH}$ domains specifically binding to a tumor-specific antigen as disclosed herein are preferably in monomeric form (as further described herein), in particular alternative embodiments, two or more of the radiolabelled $V_{HH}$ domains specifically binding to a tumor-specific antigen as disclosed herein may be linked to each other or may be interconnected. In particular embodiments, the two or more heavy chain variable domains are linked to each other via one or more suitable linkers or spacers. Suitable spacers or linkers for use in the coupling of different heavy chain variable domains as disclosed herein will be clear to the skilled person and may generally be any linker or spacer used in the art to link peptides and/or proteins.

Some particularly suitable linkers or spacers include for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length between 1 and 50 amino acids, such as between 1 and 30, and in particular between 1 and 10 amino acid residues. It should be clear that the length, the degree of flexibility and/or other properties of the linker(s) may have some influence on the properties of the heavy chain variable domains, including but not limited to the affinity, specificity or avidity for the solid tumor target.

It should be clear that when two or more linkers are used, these linkers may be the same or different. In the context and disclosure of the present invention, the person skilled in the art will be able to determine the optimal linkers for the purpose of coupling heavy chain variable domains as disclosed herein without any undue experimental burden.

Fragments of Heavy Chain Variable Domains

The present invention also encompasses parts, fragments, analogs, mutants, variants, and/or derivatives of the radiolabelled $V_{HH}$ domains specifically binding to a tumor-specific antigen as disclosed herein and/or polypeptides comprising or essentially consisting of one or more of such parts, fragments, analogs, mutants, variants, and/or derivatives, as long as these parts, fragments, analogs, mutants, variants, and/or derivatives are suitable for the purposes envisaged herein. Such parts, fragments, analogs, mutants, variants, and/or derivatives according to the invention are still capable of specifically binding to the tumor-specific antigen and are also referred to herein as 'functional fragments' of the $V_{HH}$'s as disclosed herein.

Nucleic Acid Sequences

In a further aspect, the present invention provides nucleic acid sequences encoding the $V_{HH}$ domain amino acid sequences in the compositions as disclosed herein (or suitable fragments thereof). These nucleic acid sequences can also be in the form of a vector or a genetic construct or polynucleotide. The nucleic acid sequences as disclosed herein may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

Constructs, Vectors, Host Cells

The genetic constructs as disclosed herein may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

Accordingly, in another further aspect, the present invention also provides vectors comprising one or more nucleic acid sequences as disclosed herein.

In still a further aspect, the present invention provides hosts or host cells that express or are capable of expressing one or more amino acid sequences as disclosed herein. Suitable examples of hosts or host cells for expression of the $V_{HH}$ sequences, polypeptides of the invention will be clear to the skilled person.

Polypeptides Comprising VHH Domains

In a further aspect, the present invention provides polypeptides (also referred to herein as "polypeptides as disclosed herein") that comprise or essentially consist of at least one $V_{HH}$ sequences or functional fragments thereof of the present invention that specifically binds to a tumor-specific antigen. The polypeptides of the invention may comprise at least one $V_{HH}$ as disclosed herein and optionally one or more further groups, moieties, residues optionally linked via one or more linkers.

In particularly preferred embodiments, the present invention provides polypeptides and pharmaceutical compositions comprising a $V_{HH}$ domain in its monomeric form, i.e. comprising only one $V_{HH}$ domain so as to minimize the in vivo half-life of said polypeptides and pharmaceutical compositions as much as possible.

In alternative embodiments, however the present invention also provides polypeptides and pharmaceutical compositions comprising two or more identical or different $V_{HH}$ domains resulting in a bivalent (or multivalent) or a bispecific or (multispecific) polypeptide.

The polypeptides as disclosed herein may at least contain one or more further groups, moieties or residues for binding to other targets or target proteins of interest. It should be clear that such further groups, residues, moieties and/or binding sites may or may not provide further functionality to the amino acid sequences as disclosed herein (and/or to the polypeptide or composition in which it is present) and may or may not modify the properties of the amino acid sequence as disclosed herein. Such groups, residues, moieties or binding units may also for example be chemical groups which can be biologically and/or pharmacologically active.

These groups, moieties or residues are, in particular embodiments, linked N- or C-terminally to the amino acid sequence as disclosed herein.

Origin and Form of VHH Sequences, Polypeptides and Compositions as Disclosed Herein It should be noted that the invention is not limited as to the origin of the $V_{HH}$ sequences or functional fragments thereof, polypeptides or compositions of the invention (or of the nucleotide sequences of the invention used to express them). Furthermore, the present invention is also not limited as to the way that the $V_{HH}$ sequences or functional fragments thereof, polypeptides or nucleotide sequences as disclosed herein have been generated or obtained. Thus, the amino acid sequences as disclosed herein may be synthetic or semi-synthetic amino acid sequences, polypeptides or proteins.

The amino acid sequences, polypeptides and compositions provided by the invention can be in essentially isolated form (as defined herein), or alternatively can form part of a polypeptide or composition as disclosed herein, which may comprise or essentially consist of at least one amino acid sequence as disclosed herein and which may optionally further comprise one or more other groups, moieties or residues (all optionally linked via one or more suitable linkers).

Target Species and Cross-Reactivity

It will be appreciated based on the disclosure herein that for diagnostic and/or prognostic and/or predictive applications, the $V_{HH}$ sequences, polypeptides and compositions as disclosed herein will in principle be directed against or specifically bind to all forms of the tumor-specific antigen, and in particular but not limited to all forms of HER2. However, where the $V_{HH}$ sequences or functional fragments thereof, polypeptides and compositions as disclosed herein are intended for veterinary purposes, they will be directed against or specifically bind to all forms of the tumor-specific antigen from the species intended to be treated, or they will be at least cross-reactive with all forms of the tumor-specific antigen, and in particular but not limited to all forms of HER2, from the species to be treated. Accordingly, $V_{HH}$ sequences or functional fragments thereof, polypeptides and compositions that specifically bind to all forms of the tumor-specific antigen, and in particular but not limited to all forms of HER2, from one subject species may or may not show cross-reactivity with all forms of the tumor-specific antigen from one or more other subject species. Of course it is envisaged that, in the context of the development of amino acid sequences for use in humans or animals, $V_{HH}$ sequences or functional fragments thereof may be developed which bind to forms of the tumor-specific antigen, and in particular but not limited to all forms of HER2, from another species than that which is to be treated for use in research and laboratory testing.

It is also expected that the $V_{HH}$ sequences or functional fragments thereof and polypeptides of the invention will bind to a number of naturally occurring or synthetic analogs, variants, mutants, alleles, parts and fragments of the tumor-specific antigen, and in particular but not limited to all forms of HER2. More particularly, it is expected that the $V_{HH}$ sequences or functional fragments thereof and polypeptides of the invention will bind to at least those analogs, variants, mutants, alleles, parts and fragments of the tumor-specific antigen, and in particular but not limited to all forms of HER2, that (still) contain the binding site, part or domain of the (natural/wild-type) tumor-specific antigen to which those $V_{HH}$ sequences and polypeptides bind.

Targets

In particular embodiments, $V_{HH}$ domains or functional fragments thereof disclosed herein are obtained by affinity selection against a particular target protein present on and/or specific for a solid tumor. Obtaining suitable polypeptides by affinity selection against a particular solid tumor antigen may for example be performed by screening a set, collection or library of cells that express $V_{HH}$'s on their surface (e.g. bacteriophages) for binding against a tumor-specific antigen; all of which may be performed in a manner known per se, essentially comprising the following non-limiting steps: a) obtaining an isolated solution or suspension of a tumor-specific protein target molecule, which molecule is known to be a target for a potential cancer drug; b) bio-panning phages or other cells from a $V_{HH}$ library against said protein target molecule; c) isolating the phages or other cells binding to the tumor-specific protein target molecule; d) determining the nucleotide sequence encoding the $V_{HH}$ insert from individual binding phages or other cells; e) producing an amount of $V_{HH}$ according to this sequence using recombinant protein expression and f) determining the affinity of said $V_{HH}$ domain for said tumor-specific protein target molecule and optionally g) testing the tumor detecting activity of said $V_{HH}$ domain in a bio-assay. Various methods may be used to determine the affinity between the $V_{HH}$ domain and the tumor-specific protein target molecule, including for example, enzyme linked immunosorbent assays (ELISA) or Surface Plasmon Resonance (SPR) assays, which are common practice in the art, for example, as described in Sambrook et al. (2001), Molecular Cloning, A Laboratory Manual. Third Edition. Cold Spring Harbor Laboratory Press, Cold Spring Harbor, N.Y. The dissociation constant is commonly used to describe the affinity between a polypeptide and its target molecule. Typically, the dissociation constant of the binding between the polypeptide and its target molecule is lower than $10^{-5}$ M, more preferably, the dissociation constant is lower than $10^{-6}$ M, even more preferably, the dissociation constant is lower than $10^{-7}$ M, most preferably the dissociation constant is lower than $10^{-8}$ M, such as preferably below $10^{-9}$ M, more preferably below $0.5 \cdot 10^{-9}$ M, such as below $10^{-10}$ M.

In particular embodiments, the VHH fragments as disclosed herein specifically bind to a solid tumor antigen with a dissociation constant of between about $2 \cdot 10^{-9}$ M and about $3 \cdot 10^{-9}$ M.

Tumor-specific antigens or tumor-associated antigens are molecules occurring specifically or being expressed specifically and/or abundantly on the surface of tumor cells and preferably not or only in relatively low concentration or density on the surface of normal healthy cells. When these tumor-specific antigens or tumor-associated antigens are bound to the radiolabelled $V_{HH}$'S or functional fragments thereof as disclosed herein, the corresponding tumor cells onto which the antigens are expressed are specifically labelled and can therefore be detected with high sensitivity using a suitable assay.

Suitable tumor-specific target molecules are readily available from existing literature or patent databases for the skilled person and include, without limitation any protein produced in a tumor cell that has an abnormal structure due to mutation, including the abnormal products of ras and p53 genes, tissue differentiation antigens, mutant protein antigens, oncogenic viral antigens, cancer-testis antigens, oncofetal antigens and vascular or stromal specific antigens. Examples of specific tumor antigens include but are not limited to CTAG1B, MAGEA1, the enzyme tyrosinase, alphafetoprotein (AFP), carcinoembryonic antigen (CEA), EBV and HPV, abnormally structured cell surface glycolipids and glycoproteins and HER2, EGFR or variants thereof.

In particular embodiments, the tumor-specific antigen against which the radiolabelled $V_{HH}$ or functional fragments thereof domains as disclosed herein are specifically directed for use in the diagnosis and/or prognosis of cancer and/or for the prediction of the patient's response to a cancer therapy is HER2.

In particular embodiments, the present invention provides radiolabelled $V_{HH}$ sequences or functional fragments thereof specifically directed against HER2 for use in the diagnosis and/or prognosis of breast cancer and/or for the prediction of the patient's response to a breast cancer therapy at a calculated mean effective dose as low as between 0.002 and 0.1 mSv/MBq. In further particular embodiments, the present invention provides radiolabelled $V_{HH}$ sequences or functional fragments thereof specifically directed against HER2 for use in the diagnosis and/or prognosis of breast cancer at a calculated mean effective dose as low as between 0.002 and 0.1 mSv/MBq.

In further particular embodiments, the present invention provides radiolabelled $V_{HH}$ sequences specifically directed against HER2 having an amino acid sequence, which has at least 80%, preferably at least 85%, such as 90% or 95% or more sequence identity with SEQ ID NO: 4 or functional fragments thereof, for use in the diagnosis and/or prognosis of cancer and/or for the prediction of the patient's response to a cancer therapy at a calculated mean effective dose as low as between 0.002 and 0.1 mSv/MBq.

In further particular embodiments, the present invention provides radiolabelled $V_{HH}$ sequences specifically directed against HER2 having an amino acid sequence with SEQ ID NO: 4 or functional fragments thereof, for use in the diagnosis and/or prognosis of cancer and/or for the prediction of the patient's response to a cancer therapy at a calculated mean effective dose as low as between 0.002 and 0.1 mSv/MBq.

In further particular embodiments, the present invention provides $^{68}$Ga-labelled $V_{HH}$ sequences or functional fragments thereof, specifically directed against a tumor antigen for use in the diagnosis and/or prognosis of cancer and/or for the prediction of the patient's response to a cancer therapy at a calculated mean effective dose as low as between 0.002 and 0.1 mSv/MBq.

In particular embodiments, the present invention provides $^{68}$Ga-labelled $V_{HH}$ sequences or functional fragments thereof specifically directed against HER2 for use in the diagnosis and/or prognosis of breast cancer and/or for the prediction of the patient's response to a breast cancer therapy at a calculated mean effective dose as low as between 0.002 and 0.1 mSv/MBq.

In further particular embodiments, the present invention provides $^{68}$Ga-labelled $V_{HH}$ sequences specifically directed against HER2 having an amino acid sequence, which has at least 80%, preferably at least 85%, such as 90% or 95% or more sequence identity with SEQ ID NO: 4 or functional fragments thereof, for use in the diagnosis and/or prognosis of cancer and/or for the prediction of the patient's response to a cancer therapy at a calculated mean effective dose as low as between 0.002 and 0.1 mSv/MBq.

In further particular embodiments, the present invention provides $^{68}$Ga-labelled $V_{HH}$ sequences specifically directed against HER2 having SEQ ID NO: 4 or functional fragments thereof, for use in the diagnosis and/or prognosis of cancer and/or for the prediction of the patient's response to a cancer therapy at a calculated mean effective dose as low as between 0.002 and 0.1 mSv/M Bq.

In yet further particular embodiments, the present invention provides $^{68}$Ga-labelled $V_{HH}$ sequences specifically directed against HER2 having an amino acid sequence, which has at least 80%, preferably at least 85%, such as 90% or 95% or more sequence identity with SEQ ID NO: 4 or functional fragments thereof, for use in the diagnosis and/or prognosis of breast cancer and/or for the prediction of the patient's response to a breast cancer therapy at a calculated mean effective dose as low as between 0.002 and 0.1 mSv/MBq.

In yet further particular embodiments, the present invention provides $^{68}$Ga-labelled $V_{HH}$ sequences specifically directed against HER2 having SEQ ID NO: 4 or functional fragments thereof, for use in the diagnosis and/or prognosis of breast cancer and/or for the prediction of the patient's response to a breast cancer therapy at a calculated mean effective dose as low as between 0.002 and 0.1 mSv/MBq.

In certain non-limiting embodiments, the radio-labelled $V_{HH}$ sequences or functional fragments thereof of the present invention are specifically directed against a binding site on HER2, which is different from the Herceptin® (Trastuzumab) binding site on HER2 and/or do not compete with Herceptin® for binding to HER-2, as determined using a suitable competition assay.

In particular embodiments, the radio-labelled $V_{HH}$ sequences or functional fragments thereof of the present invention are specifically directed against a binding site on HER2, which is different from (i.e. is not) domain IV of HER2.

In yet further particular embodiments, the radio-labelled $V_{HH}$ sequences or functional fragments thereof of the present invention are specifically directed against a binding site on HER2, which is different from (i.e. is not) the C-terminus of domain IV of HER2.

Thus, in particular embodiments, the radio-labelled $V_{HH}$ sequences or functional fragments thereof of the present invention do not compete with the monoclonal antibody Herceptin® (Trastuzumab) for binding to HER2, as determined using a suitable competition assay. Specific competition binding of a $V_{HH}$ can be determined in any suitable competitive binding assay known per se, such as radioimmunoassays (RIA), enzyme immunoassays (EIA) and sandwich competition assays, and the different variants thereof known in the art.

In addition, because of their extremely high specificity for tumor cells, a certain class of the radiolabelled VHH's or functional fragments thereof as disclosed herein, have been found to be particularly suitable tools for detecting and diagnosing certain types of cancers, which cannot be easily and/or unambiguously detected using the currently available diagnostic assays for such cancer types. More specifically, the present inventors have found that the radio-labelled antibody fragments, and in particular radiolabelled $V_{HH}$'s or functional fragments thereof as disclosed herein that are directed against the tumor-specific antigen HER2, can be used to effectively diagnose HER-2 positive cancer (lesions) and/or make an accurate prognosis of HER-2 positive cancer (lesions) in an animal or human, which was initially diagnosed to be HER-2 negative using one or more standard available assays for diagnosing HER-2 positive cancer (lesions).

The importance of HER2 as a prognostic, predictive, and therapeutic marker for certain types of cancer, and in particular, for invasive breast cancer, is well recognized, and therefore, it is critical to validate and standardize testing techniques in order to make an accurate assessment of the HER2 status. There are however significant contradictions among the outcomes of known available tests.

Therefore, with the radiolabeled $V_{HH}$'s or functional fragments thereof specifically directed against HER2, the present invention meets the high need for a reproducible, high-throughput and highly sensitive diagnostic tools and assays for diagnosis and prognosis of HER-2 related cancers.

Techniques which are known to assess HER2 protein overexpression are immunohistochemistry, ELISA analysis of tumor cytosols or serum, and Western blot, and methods used to evaluate HER2 gene amplification include Southern blot, slot blot, CISH, FISH, and PCR.

Use of solid matrix blotting techniques like Southern blot, slot blot, and especially Western blot are significantly limited due to the dilutional artifacts in the tumor sample. In breast cancer specimens, these artifacts may be composed of benign breast ductal cells, acini, stromal cells, inflammatory cells, and vascular structures resulting in false negative cases. In addition, these techniques need a large amount of tissues which would not be available in biopsy specimens. PCR is a sensitive technique; however, it is also affected by dilutional artifacts, and the analysis is time consuming and labor intensive. The absence of simultaneous morphological assessment in the above studies is also a significant disadvantage.

Contrary to the above, analysis by IHC and FISH can be automated and allow the simultaneous assessment of tumor morphology while eliminating difficulties with dilution artifacts.

IHC analysis of HER2 is a simple-to-perform, widely available and inexpensive test. It is nevertheless affected by several variables including tissue-fixation methods, reagents, assay protocols, antibody sensitivities and specificities, and scoring systems. Moreover, it is an invasive detection technique.

Also, while in general, testing of freshly frozen tissues is more reliable than paraffin-embedded tissues as formaldehyde causes cross linking of proteins hindering the access of antibody to the epitope, practically, it is not possible to have fresh tissues available in all cases especially when testing at reference laboratories and analyzing archival tissues.

FISH is a relatively reliable, reproducible, sensitive, and accurate procedure which is less affected by tissue fixation and analytical variables compared to IHC. It also offers the benefit of simultaneous evaluation of morphology and gene amplification. Relative to solid matrix blotting procedures, analysis of HER2 gene amplification by FISH showed a sensitivity of 98% and specificity of 100%. The technique, however, is more complex and labor intensive than IHC.

While there is a relatively good concordance between tumors scored as 3+ by IHC and clearly positive, i.e. a value>2, by FISH (clear-cut HER-2 positive cancer cases), cases scoring 2+ by IHC generally showed the most discrepancy with the results of parallel FISH tests. Indeed, several studies showed an absence of HER2 gene amplification using FISH in subsets of cases which were scored 2+ by IHC. These inconsistencies may be due to several causes including discrepancies between protein expression and gene amplification, variability in tissue fixation and processing, intratumoral heterogeneity, and polysomy of chromosome 17.

Hence, up to date there are no tools or assays available, which allow an accurate diagnosis for those cases where a combined approach with IHC and FISH analysis did not reveal an unambiguous result or in those cases with a HER2-positive outcome using IHC and a HER-2 negative outcome using FISH.

Accurate assessment of HER2 status is critical in the management of patients with invasive breast cancer. In an attempt to standardize HER2 testing and to improve the accuracy and reproducibility of the test results, the American Society of Clinical Oncology/College of American Pathologists (ASCO/CAP) panel has made recommendations for HER2 interpretation and testing. The panel recommended determination of HER2 status in all cases of invasive breast carcinoma. Algorithms for interpreting HER2 gene amplification by FISH and protein expression by IHC are provided. The guidelines by ASCO/CAP define an HER2 IHC staining of 3+ as uniform intense membrane staining in >30% of invasive tumor cells as compared to previously defined >10% strong staining. Cases with weak to moderate complete membrane staining in at least 10% of cells are considered equivocal (2+), and in these cases, HER2 gene amplification with fluorescent in situ hybridization (FISH) should be tested. For FISH, the tumor is negative for HER2 gene amplification (and defined or referred to herein as HER-2 negative) if the ratio of HER2 gene signals to chromosome17 signals is <1.8 (or < about 2.0) or HER2 gene copy number is <4.0, equivocal when the ratio is 1.8-2.2 or HER2 gene copy number is 4.0-6.0 and positive for HER2 gene amplification (and defined or referred to herein as HER-2 positive) if the ratio is >2.2 (or > about 2.0) or HER2 gene copy number is >6.0. Guidelines for tissue processing include keeping the time from tissue acquisition to fixation as short as possible and fixation in 10% neutral buffered formalin for 6-48 hours. Additional guidelines for optimal test validation, internal quality assurance procedures, external proficiency assessment, and laboratory accreditation are also provided.

Thus, in a further aspect, the present invention provides radio-labelled $V_{HH}$ sequences or functional fragments thereof specifically directed against HER2, which can be used to identify HER-2 positive cancer lesions in human subjects initially diagnosed to be HER-2 negative in at least one standard assay for identifying HER-2 positive cancer lesions. In particular embodiments, the present invention provides radio-labelled $V_{HH}$ sequences or functional fragments thereof specifically directed against HER2, which can be used to identify HER-2 positive cancer lesions in human subjects initially diagnosed to be HER-2 negative in a FISH assay for Her2 gene amplification, in particular through yielding of a score less than about 2.0.

It has been found that the radio-labelled $V_{HH}$ sequences specifically directed against HER2, which can be used to identify HER-2 positive cancer lesions in human subjects, while being effective to detect primary HER-2 positive tumors are also particularly suitable to detect HER-2 positive metastatic lesions, which are typically less easy to detect.

In further particular embodiments, the present invention provides radiolabelled $V_{HH}$ sequences or functional fragments thereof specifically directed against HER2, which can be used to identify HER-2 positive breast cancer lesions in human subjects initially diagnosed to be HER-2 negative in at least one standard assay for identifying HER-2 positive breast cancer lesions.

In still further particular embodiments, the present invention provides radiolabelled $V_{HH}$ sequences or functional fragments thereof specifically directed against HER2, which can be used to identify HER-2 positive cancer lesions in human subjects initially diagnosed to be HER-2 negative in at least one standard assay for identifying HER-2 positive cancer lesions and wherein the radiolabelled $V_{HH}$ sequences have an amino acid sequence, which has at least 80%, preferably at least 85%, such as 90% or 95% or more sequence identity with SEQ ID NO: 4 or functional fragments thereof.

In further particular embodiments, the present invention provides radiolabelled $V_{HH}$ sequence or functional fragments thereof specifically directed against HER2, which can be used to identify HER-2 positive cancer lesions in human subjects initially diagnosed to be HER-2 negative in at least one standard assay for identifying HER-2 positive cancer lesions, wherein the radiolabelled $V_{HH}$ sequences have an amino acid sequence with SEQ ID NO: 4 or functional fragments thereof.

In further particular embodiments, the present invention provides $^{68}$Ga-labelled $V_{HH}$ sequences or functional fragments thereof specifically directed against HER2, which can be used to identify HER-2 positive cancer lesions in human subjects initially diagnosed to be HER-2 negative in at least one standard assay for identifying HER-2 positive cancer lesions. In yet further particular embodiments, the type of cancer is breast cancer.

In further particular embodiments, the present invention provides $^{68}$Ga-labelled $V_{HH}$ sequences or functional fragments thereof specifically directed against HER2, which can be used to identify HER-2 positive cancer lesions in human subjects initially diagnosed to be HER-2 negative in at least one standard assay for identifying HER-2 positive cancer lesions, wherein the radiolabelled $V_{HH}$ sequences have at least 80%, preferably at least 85%, such as 90% or 95% or more sequence identity with SEQ ID NO:4 or functional fragments thereof. In still further particular embodiments, these $^{68}$Ga-labelled $V_{HH}$ sequences or functional fragments thereof specifically directed against HER2 that can be used to identify HER-2 positive cancer lesions in human subjects initially diagnosed to be HER-2 negative in at least one standard assay for identifying HER-2 positive cancer lesions, have an amino acid sequence with SEQ ID NO: 4 or functional fragments thereof. In yet further particular embodiments, the type of cancer is breast cancer.

In particularly preferred embodiments, the present invention provides the $^{68}$Ga-labelled $V_{HH}$ domains as disclosed herein in their monomeric form as well as polypeptides and pharmaceutical compositions comprising a $V_{HH}$ domain in its monomeric form, i.e. comprising only one $V_{HH}$ domain so as to minimize the in vivo half-life of said polypeptides and pharmaceutical compositions as much as possible thereby reducing potential unwanted side effects and toxicity issues.

Through the improved diagnostic VHH's of the present invention, both primary and metastatic lesions can be detected with high accuracy. Since a IHC 3+ or positive FISH test result is sometimes required to be able to benefit from social security reimbursement of HER-2 targeted therapies, the tumors determined to be positive with the HER-2 specific $V_{HH}$'s as disclosed herein, can afterwards be re-tested in a FISH assay at the specific site where the lesions were detected using the VHH's as disclosed herein, in order to obtain a correct FISH positive result.

Forms of Target Antigen

It will be appreciated based on the disclosure herein that for medical applications, i.e. applications for diagnostis and/or prognosis and/or prediction of response to cancer therapy, the heavy chain variable domains as disclosed herein will in principle be directed against or specifically bind to several different forms of the tumor-specific antigen. It is also expected that VHH's or functional fragments thereof as disclosed herein will bind to a number of naturally occurring or synthetic analogs, variants, mutants, alleles, parts and fragments of their tumor antigen. More particularly, it is expected that the heavy chain variable domains or functional fragments thereof as disclosed herein will bind to at least to those analogs, variants, mutants, alleles, parts and fragments of the tumor antigen that (still) contain the binding site, part or domain of the natural tumor antigen to which those $V_{HH}$'s bind.

In particular embodiments, where the invention provides $V_{HH}$'s that are specifically directed against HER2, it is within the scope of the invention that the VHH's as disclosed herein can only bind to HER2 in monomeric form, or can only bind to HER2 in multimeric form, or can bind to both the monomeric and the multimeric form of HER2. Again, in such a case, the $V_{HH}$'s as disclosed herein may bind to the monomeric form of HER2 with an affinity and/or specificity that are the same as, or that are different from (i.e. higher than or lower than), the affinity and specificity with which the $V_{HH}$'s as disclosed herein bind to the multimeric form.

Also, when HER2 can associate with other proteins or polypeptides (e.g. with other ERBB receptors, also referred to as heterodimerization) to form protein complexes (e.g. with multiple subunits), it is within the scope of the invention that the $V_{HH}$'s as disclosed herein can bind to HER2 in its non-associated state, or can bind HER2 in its associated state, or can bind to both. Generally, $V_{HH}$ sequences as disclosed herein will at least bind to those forms of HER2 (including monomeric, multimeric and associated forms)

Methods of Production and Manufacturing of Vhh Sequences as Disclosed Herein The invention further provides methods for preparing or generating the $V_{HH}$ domain sequences or functional fragments thereof, as well as methods for producing nucleic acids encoding these and host cells, products and compositions comprising these heavy chain variable domain sequences. Some preferred but non-limiting examples of such methods will become clear from the further description herein.

As will be clear to the skilled person, one particularly useful method for preparing heavy chain variable domain sequences as disclosed herein generally comprises the steps of:

(a) expressing a nucleotide sequence encoding a heavy chain variable domain sequence as disclosed herein or a vector or genetic construct a nucleotide sequence encoding that heavy chain variable domain sequence and (b) optionally isolating and/or purifying the heavy chain variable domain sequence.

In particular embodiments envisaged herein, the tumor-specific heavy chain variable domain sequences can be obtained by methods which involve generating a random library of $V_{HH}$ sequences and screening this library for an $V_{HH}$ sequence capable of specifically binding to a tumor-specific target protein.

Accordingly, in particular embodiments, methods for preparing a heavy chain variable domain sequence as disclosed herein comprise the steps of a) providing a set, collection or library of amino acid sequences of $V_{HH}$ domains; and b) screening said set, collection or library of amino acid sequences for amino acid sequences that can bind to and/or have affinity for the tumor-specific target.

and c) isolating the amino acid sequence(s) that can bind to and/or have affinity for the tumor-specific target.

In such a method, the set, collection or library of $V_{HH}$ sequences may be any suitable set, collection or library of amino acid sequences. For example, the set, collection or library of amino acid sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of $V_{HH}$ sequences may be an immune set, collection or library of immunoglobulin fragment sequences, for example derived from a mammal that has been suitably immunized with a tumor-specific target or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of $V_{HH}$ sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In other embodiments, the methods for generating the heavy chain variable domain sequences as disclosed herein comprise at least the steps of:

a) providing a collection or sample of cells expressing $V_{HH}$ domain amino acid sequences;

b) screening said collection or sample of cells for cells that express an amino acid sequence that can bind to and/or have affinity for a tumor-specific target;

and c) either (i) isolating said amino acid sequence; or (ii) isolating from said cell a nucleic acid sequence that encodes said amino acid sequence, followed by expressing said amino acid sequence.

The collection or sample of cells may for example be a collection or sample of B-cells. Also, in this method, the sample of cells may be derived from a mammal that has been suitably immunized with a tumor-specific target or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a heavy chain variable domain sequence directed against a tumor-specific target may comprise at least the steps of:

a) providing a set, collection or library of nucleic acid sequences encoding a $V_{HH}$ domain amino acid sequence;

b) screening said set, collection or library of nucleic acid sequences for nucleic acid sequences that encode an amino acid sequence that can bind to and/or has affinity for the tumor-specific target;

and c) isolating said nucleic acid sequence, followed by expressing said amino acid sequence.

In the above methods, the set, collection or library of nucleic acid sequences encoding amino acid sequences may for example be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In particular, in such a method, the set, collection or library of nucleic acid sequences encodes a set, collection or library of $V_{HH}$ domains directed against a tumor-specific antigen (as defined herein).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to $V_{HH}$ sequences that are obtainable or obtained by the above methods, or alternatively by a method that comprises one of the above methods and in addition at least the steps of determining the nucleotide sequence or amino acid sequence of said $V_{HH}$ sequence; and of expressing or synthesizing said $V_{HH}$ sequence in a manner known per se, such as by expression in a suitable host cell or host organism or by chemical synthesis.

Isolation of VHH Domains as Disclosed Herein

In some cases, the methods for producing the amino acid sequences binding specifically to a tumor-specific target as envisaged herein may further comprise the step of isolating from the amino acid sequence library at least one $V_{HH}$ domain having detectable binding affinity for, or detectable in vitro effect on a tumor-specific target.

These methods may further comprise the step of amplifying a sequence encoding at least one $V_{HH}$ domain having detectable binding affinity for, or detectable in vitro effect on the activity of a tumor-specific target. For example, a phage clone displaying a particular amino acid sequence, obtained from a selection step of a method described herein, may be amplified by reinfection of a host bacteria and incubation in a growth medium.

In particular embodiments, these methods may encompass determining the sequence of the one or more amino acid sequences capable of binding to a tumor-specific target.

Where a heavy chain variable domain sequence, comprised in a set, collection or library of amino acid sequences, is displayed on a suitable cell or phage or particle, it is possible to isolate from said cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a $V_{HH}$ domain as envisaged herein comprise the step of expressing said nucleotide sequence(s) in a host organism under suitable conditions, so as to obtain the actual desired amino acid sequence. This step can be performed by methods known to the person skilled in the art.

In addition, the obtained $V_{HH}$ domain sequences or functional fragments thereof having detectable binding affinity for, or detectable in vitro effect on the activity of a tumor-specific target, may be synthesized as soluble protein construct, optionally after their sequence has been identified.

For instance, the $V_{HH}$ domain sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the $V_{HH}$ sequences obtained, obtainable or selected by the above methods may comprise transforming or infecting a host cell with a nucleic acid or a vector encoding an amino acid sequence having detectable binding affinity for, or detectable in vitro effect on the activity of a tumor-specific target. Accordingly, the $V_{HH}$ sequences having detectable binding affinity for, or detectable in vitro effect on the activity of a tumor-specific target can be made by recombinant DNA methods. DNA encoding the amino acid sequences can be readily synthesized using conventional procedures. Once prepared, the DNA can be introduced into expression vectors, which can then be transformed or transfected into host cells such as E. coli or any suitable expression system, in order to obtain the expression of amino acid sequences in the recombinant host cells and/or in the medium in which these recombinant host cells reside.

It should be understood, as known by someone skilled in the art of protein expression and purification, that the $V_{HH}$ domain produced from an expression vector using a suitable expression system may be tagged (typically at the N-terminal or C-terminal end of the amino acid sequence) with e.g. a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired heavy chain variable domain sequences may be any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic plant.

Thus, the application also provides methods for the production of $V_{HH}$ domain sequences having detectable binding affinity for, or detectable in vitro effect on the activity of a tumor antigen comprising transforming, transfecting or infecting a host cell with nucleic acid sequences or vectors encoding such $V_{HH}$ sequences and expressing their amino acid sequences under suitable conditions.

In yet another embodiment, the invention further provides methods for the manufacture ('or the production of' which is equivalent wording) a pharmaceutical composition as disclosed herein.

In particular embodiments, the invention provides methods for producing a pharmaceutical composition as disclosed herein, at least comprising the steps of:
  obtaining at least one $V_{HH}$ or a functional fragment thereof, which specifically binds to a tumor antigen, and
  formulating said $V_{HH}$ or functional fragment thereof in a pharmaceutical composition.

In particular embodiments of these methods, the step of obtaining at least one heavy chain variable domain or functional fragment thereof, which specifically binds to a tumor-specific antigen comprises:
  (a) expressing a nucleotide sequence encoding a $V_{HH}$ or functional fragment thereof, which specifically binds to a tumor-specific antigen, and optionally
  (b) isolating and/or purifying the $V_{HH}$ or functional fragment thereof.

In other particular embodiments of these methods, the step of obtaining at least one $V_{HH}$ or functional fragment thereof, which specifically binds to a tumor-specific protein target comprises:
  a) providing a set, collection or library of $V_{HH}$ domain sequences or functional fragments of $V_{HH}$ sequences;
  b) screening said set, collection or library of $V_{HH}$ domain sequences or sequences of functional fragments thereof for sequences that specifically bind to and/or have affinity for a tumor antigen, and optionally
  c) isolating the $V_{HH}$ sequences or sequences of functional fragments thereof that specifically bind to and/or have affinity for a tumor-specific antigen.

Radiolabelling of Vhh Domains as Disclosed Herein

In order to be suitable for the diagnostic and/or prognostic and/or predictive purposes, especially for the diagnosis and/or prognosis and/or prediction of the patient's response to therapy of cancer-related diseases and disorders, where it is intended to specifically detect a tumor cell that expresses a tumor-specific antigen against which the $V_{HH}$'s or functional fragments thereof as disclosed herein are directed against, the $V_{HH}$'s as disclosed herein are linked to or coupled to, such as chemically coupled to, a radionuclide.

Examples of suitable radionuclides which can be linked to a $V_{HH}$ or functional fragments thereof as disclosed herein in order to provide a compound for the diagnosis and/or prognosis and/or for the prediction of the patient's response to a cancer therapy of cancer will be clear to the skilled person and can for example without any limitation be chosen from the group consisting of α-emitting radioisotopes and β-emitting radioisotopes, including but not limited to a radioisotope chosen from the group consisting of group consisting of 68Ga, 123I, 124I, 125I, 131I, 18F, 111In, 99mTc, 64Cu, 86Y, 76Br, 89Zr, 177Lu, 133Xe, 90Y, 201Tl, 82Rb, 209At, 210At, 211At, 209At, 210At and 211At. In still further particular embodiments, the radiolabelled $V_{HH}$'s or functional fragments thereof as disclosed herein are labelled with Gallium-68.

There are various radiolabeling strategies available to incorporate a radionuclide into a protein. The choice of technique for a radiochemist depends primarily on the radionuclide used. The radioactive isotopes of iodine possess the ability to be directly integrated into a molecule by electrophilic substitution or indirectly via conjugation. Radioactive metals on the other hand are labeled via complexation with a chelating agent. Many metallic radionuclides possess the ability to form stable complexes with chelating agents, thus allowing for conjugation with a protein.

Current interest in the coordination chemistry of gallium stems, at least in large part, from potential applications of $^{68}$Ga-labeled biomolecules as PET imaging agents. Gallium is a IIIB metal. The most prevalent oxidation state of gallium in aqueous solution is +3. Due to its high charge density, Ga(III) prefers hard donors, such as amine-N and carboxylate-O atoms. Because of the small size, Ga(III) is often six-coordinated. Ga(III) is similar to Fe(III) with respect to its coordination chemistry and biological properties. Since it is a highly charged cation, hydrolysis of Ga(III) at pH>4 remains a significant challenge during radiolabeling. Another challenge is the ligand exchange with transferrin after $^{68}$Ga radiopharmaceuticals are injected into biological system. Macrocyclic and acyclic BFCs, NODASA (1,4,7-triazacyclononane-N-succinic acid-N',N''-diacetic acid) and NODAGA (1,4,7-triazacyclononane-N-glutamic acid-N', N''-diacetic acid) are particularly useful for chelation of $^{68}$Ga due to the perfect fit between the size of Ga(III) and coordination cavity formed by the $N_3O_3$ donor atoms. Also DOTA (1,4,7,10-tetraazacyclododecane-1,4,7,10-tetraacetic acid) and NOTA (1,4,7-triazacyclononane-1,4,7-triacetic acid) are useful chelators for Ga-labelling.

DTPA, DOTA and NOTA derivatives are often used for the $^{68}$Ga labeling of small biomolecules. Among different BFCs, NODASA and NODAGA are particularly useful for $^{68}$Ga-labeling due to the high hydrophilicity and stability of their $^{68}$Ga chelates, and their higher $^{68}$Ga-labeling efficiency than that of the corresponding DOTA analogs. The fast and efficient radiolabeling is especially critical for the $^{68}$Ga-labeled small biomolecules due to its short half-life ($t_{1/2}$=68 min).

Detailed protocols for radiotherapy are readily available to the expert (Cancer Radiotherapy: Methods and Protocols (Methods in Molecular Medicine), Huddart R A Ed., Human Press 2002). The skilled person knows how to determine an appropriate dosing and application schedule, depending on the nature of the disease and the constitution of the patient. In particular, the skilled person knows how to assess dose-limiting toxicity (DLT) and how to determine the maximum tolerated dose (MTD) accordingly.

Preferably, the radiolabelled $V_{HH}$'s as disclosed herein may be administered via an intravenous, intraperitoneal or other route. Depending on the desired duration and effectiveness of the treatment, the radionuclide-$V_{HH}$ conjugates as disclosed herein may be administered once or several times, in combination with other therapeutic drugs or radiosensitizing agents. The amount of the radioimmunoconjugate applied depends on the precise nature of the carcinoma. The dose of radioactivity per administration must be high enough to be effective, but must be below the dose limiting toxicity (DLT).

VHH Sequences, Polypeptides and Compositions for Diagnostic and/or Prognostic and/or Predictive Purposes In yet a further aspect, compositions are provided comprising one or more $V_{HH}$ sequences or functional fragments thereof disclosed herein and/or nucleic acid sequences as envisaged herein and optionally at least one acceptable carrier (also referred to herein as compositions as envisaged herein).

The compositions as envisaged herein can be used in the diagnosis and/or prognosis and/or for the prediction of the patient's response to therapy of diseases and disorders associated with tumor-specific target molecules of interest. In particular, the application provides compositions comprising one or more $V_{HH}$ sequences or functional fragments thereof as envisaged herein that are suitable for diagnostic use in a warm-blooded animal, and in particular in a mammal, and more in particular in a human being.

Also provided are compositions comprising and one or more $V_{HH}$ sequences or functional fragments thereof as envisaged herein that can be used for veterinary purposes in the diagnosis and/or prognosis and/or for the prediction of the patient's response to therapy of one or more cancer-related diseases, disorders or conditions.

In further aspects, the present invention provides methods for in vitro prognosis or diagnosis of cancer, from a biological sample taken from an individual, at least comprising the steps of:

(a) providing a radiolabelled $V_{HH}$ or functional fragments thereof, polypeptide or pharmaceutical composition as disclosed herein, (b) contacting the biological sample with the radiolabelled $V_{HH}$, polypeptide or pharmaceutical composition and (c) detecting whether the amino acid sequence, polypeptide or pharmaceutical composition binds material in the sample to determine whether the tumor-specific antigen is present in the sample.

In still further aspects, the present invention provides methods for in vivo prognosis and/or diagnosis and/or for the prediction of the response to therapy of cancer in a patient suffering from that cancer, at least comprising the steps of:

(a) providing a radiolabelled $V_{HH}$ or functional fragments thereof, polypeptide or pharmaceutical composition as disclosed herein, (b) administering the radiolabelled $V_{HH}$ or functional fragments thereof, polypeptide or pharmaceutical composition to the patient suffering from the cancer, and (c) detecting whether the radiolabelled $V_{HH}$ or functional fragments thereof, polypeptide or pharmaceutical composition binds to the tumor specific antigen on cells in the patient.

In yet further aspects, the present invention provides methods for the detection of HER2 in a biological sample taken from an individual, at least comprising the steps of:

(a) providing a radiolabelled $V_{HH}$ or functional fragments thereof, polypeptide or pharmaceutical composition as disclosed herein, (b) contacting the biological sample comprising HER2 with the radiolabelled $V_{HH}$ or functional fragments thereof, polypeptide or pharmaceutical composition and (c) detecting whether the radiolabelled $V_{HH}$ or functional fragments thereof, polypeptide or pharmaceutical composition binds HER2 in the sample.

In yet further aspects, the present invention provides methods for in vitro imaging of HER-2 and/or HER-2-presenting cells from a biological sample taken from an individual, comprising the steps of:

(a) producing an immunoimaging composition comprising covalently binding an imaging moiety to a radiolabelled $V_{HH}$, polypeptide or pharmaceutical composition as disclosed herein;

(b) contacting the biological sample with the imaging composition; and (c) detecting a signal produced by the imaging moiety.

In certain other aspects, the present invention provides methods for in vivo imaging of HER-2 and/or HER-2-presenting cells, comprising the steps of:

(a) producing an immunoimaging composition comprising covalently binding an imaging moiety to a radiolabelled $V_{HH}$ or functional fragments thereof, polypeptide or pharmaceutical composition as disclosed herein;

(b) administering said imaging composition to a patient; and (c) detecting a signal produced by the imaging moiety.

In certain further aspects, the present invention provides kits for diagnosis or prognosis and/or for the prediction of a patient's response to therapy in the case of cancer comprising a radiolabelled $V_{HH}$, polypeptide or pharmaceutical composition or derivative thereof as disclosed herein.

Dose and route of administration will in general depend on the nature of the disease (type, grade, and stage of the tumor etc.) and the patient (constitution, age, gender etc.), and will be determined by the skilled medical expert responsible for the treatment. With respect to the possible doses for the compounds which are described above, it is clear that the medical expert responsible for the treatment will carefully monitor whether any dose-limiting toxicity or other severe side effects occur and undertake the necessary steps to manage those.

Generally, for diagnostic, prognostic and predictive use, the $V_{HH}$ sequences or functional fragments thereof as envisaged herein may be formulated as a preparation or compositions comprising at least one $V_{HH}$ sequence or polypeptide as envisaged herein and at least one acceptable carrier, diluent or excipient and/or adjuvant, and optionally one or more further polypeptides and/or compounds. Such a formulation may be suitable for intraperitoneal, intravenous or other administration. Thus, the $V_{HH}$ sequences, or polypeptides as envisaged herein and/or the compositions comprising the same can for example be administered systemically, locally or topically to the tissue or organ of interest, depending on the location, type and origin of the tumor, and preferably intraperitoneally or intravenously, depending on the specific pharmaceutical formulation or composition to be used.

The dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

The amount of the $V_{HH}$ sequences or functional fragments thereof and polypeptides as envisaged herein required for use in diagnosis and/or prognosis and/or for the prediction of the patient's response to a therapy may vary not only with the particular $V_{HH}$ sequence or functional fragments thereof or polypeptide selected but also with the route of administration and will be ultimately at the discretion of the attendant physician or clinician. Also the dosage of the $V_{HH}$ sequences or functional fragments thereof and polypeptides envisaged herein may vary depending on the target cell, tumor, tissue, graft, or organ.

In particular, the $V_{HH}$ sequences or functional fragments thereof and polypeptides as envisaged herein will be administered in an amount which will be determined by the medical practitioner. Typically, for each disease indication an optimal dosage will be determined specifying the amount to be administered per kg body weight, per m² body surface area or for defined patient categories. The clinician will generally be able to determine a suitable dose, depending on the factors mentioned herein. It will also be clear that in specific cases, the clinician may choose to deviate from these amounts, for example on the basis of the factors cited above and his expert judgment.

Useful dosages of the $V_{HH}$'s or functional fragments thereof and polypeptides comprising the VHH's as envisaged herein can be determined by determining their in vitro activity, and/or in vivo activity in animal models.

In certain embodiments, the present invention provides a radiolabelled $V_{HH}$ or functional fragments thereof as disclosed herein for use in the diagnosis and/or prognosis and/or for the prediction of the patient's response to cancer therapy by administering to a subject in need thereof the radiolabelled $V_{HH}$ or functional fragments thereof at a dose of between 10 μg and 1000 μg of $V_{HH}$ or functional fragments thereof. In further particular embodiments, the present invention provides a radiolabelled $V_{HH}$ or functional fragments thereof as disclosed herein for use in the diagnosis and/or prognosis of cancer by administering to a subject in need thereof the radiolabelled $V_{HH}$ or functional fragments thereof at a dose of between 10 μg and 500 μg of radiolabelled $V_{HH}$ or functional fragments thereof, such as in particular between 10 and 100 μg of radiolabelled $V_{HH}$ or functional fragments thereof, preferably between 20 and 70 μg of radiolabelled $V_{HH}$ or functional fragments thereof, such as between 40 and 60 μg of radiolabelled $V_{HH}$ or functional fragments thereof, more preferably but not limited to about 50 μg of radiolabelled $V_{HH}$ or functional fragments thereof. In certain embodiments, the present invention provides a radiolabelled $V_{HH}$ or functional fragments thereof as disclosed herein for use in the diagnosis and/or prognosis and/or for the prediction of the patient's response to cancer therapy by administering to a subject in need thereof the radiolabelled $V_{HH}$ or functional fragments thereof at a dose of between 100 μg and 200 μg of $V_{HH}$ or functional fragments thereof, preferably but not limited to about 100 μg of radiolabelled $V_{HH}$ or functional fragments thereof.

In further particular embodiments, the radiolabelled $V_{HH}$'s or functional fragments thereof as disclosed herein have a specific activity of from about 1 to about 1000 mCi/mg, or from about 5 to about 250 mCi/mg, preferably about 20 to about 50 mCi/mg, preferably about 15 to about 45 mCi/mg, preferably about 25 to about 35 mCi/mg, and most preferably 30 mCi/mg.

Methods for the calculation of (mean) effective dose to be expected in humans, based on probe biodistribution data in humans are known to the skilled person and may include software programs, such as for example but not limited to OLINDA 1.0 software. Assuming identical biodistribution of the same compound, labeled with different isotopes, a (mean) effective dose can be calculated for multiple radio-isotopes.

In particular the present inventors have found that the radio-labelled antibody fragments, and in particular radio-labelled $V_{HH}$'s or functional fragments thereof, can be used to effectively diagnose cancer and/or make an accurate prognosis and prediction of therapy response of that cancer in an animal or human suffering from that cancer, at a calculated mean effective dose of between 0.002 and 0.1 mSv/MBq in said animal or human subject.

Estimated mean effective dose calculations based on the biodistribution data of the $^{68}$Ga-labeled anti-Her2 VHH 2RS15D obtained from the first-in-human phase I trial, when using different radio-isotopes as parameter for the OLINDA calculations yield the following for different radio-isotopes: For 68-Ga: between 0.03 and 0.05 mSv/MBq, and more particularly 0.0427 mSv/MBq.

For 124-I: between 0.02 and 0.04 mSv/MBq, and more particularly 0.0304 mSv/MBq.

For 131-I: between 0.001 and 0.02 mSv/MBq, and more particularly 0.0188 mSv/MBq.

In certain embodiments, diagnosis of cancer is achieved by administering a radiolabelled $V_{HH}$ as disclosed herein to a subject in need thereof, characterized in that the $V_{HH}$ or functional fragments thereof has a calculated mean effective dose of between 0.001 and 0.05 mSv/MBq in a subject, such as but not limited to a calculated mean effective dose of between 0.02 and 0.05 mSv/MBq, more preferably between 0.02 and 0.04 mSv/MBq, most preferably between 0.03 and 0.05 mSv/MBq.

The subject or patient to which the polypeptides described herein may be administered can be any warm-blooded animal, but is in particular a mammal, and more in particular a human suffering from, or at risk of, a cancer-related disease and/or disorder.

The detection efficiency and specificity of the $V_{HH}$ sequences or functional fragments thereof and polypeptides described herein, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person.

Depending on the tumor-specific target involved, the skilled person will generally be able to select a suitable in vitro assay, cellular assay or animal model to test the $V_{HH}$ sequences or functional fragments thereof and polypeptides described herein for binding to the tumor-specific molecule; as well as for their diagnostic efficiency in respect of one or more cancer-related diseases and disorders.

In particular embodiments, the $V_{HH}$ sequences or functional fragments thereof and polypeptides envisaged herein are used for the diagnosis and/or prognosis of cancers and neoplastic conditions. Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

The $V_{HH}$ sequences and polypeptides as envisaged herein can also be used for the diagnosis and/or prognosis of a variety of proliferative disorders. Examples of proliferative disorders include hematopoietic neoplastic disorders and cellular proliferative and/or differentiative disorders, such as but not limited to, epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, miscellaneous malignant neoplasms, gynecomastia carcinoma, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma), malignant mesothelioma, non-neoplastic polyps, adenomas, familial syndromes, colorectal carcinogenesis, colorectal carcinoma, carcinoid tumors, nodular hyperplasias, adenomas, and malignant tumors, including primary carcinoma of the liver and metastatic tumors, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The above disclosure will now be further described by means of the following non-limiting Examples and Figures, in which the figures show:

BRIEF DESCRIPTION OF THE DRAWINGS

FIGS. 1A-1C: $^{68}$Ga-HER2 V$_{HH}$ PET/CT

Images were acquired 60 min after tracer injection. FIG. 1A shows the normal distribution, with the highest uptake in liver and kidneys. FIGS. 1B-1C show images of a lesion with heterogeneous tracer uptake. A heterogeneous HER2 expression was confirmed by immunohistochemistry on the surgery specimen.

FIG. 2A. Patient 4, injected with 0.01 mg $^{68}$Ga-HER2-Nanobody; FIG. 2B. Patient 12, injected with 0.1 mg $^{68}$Ga-HER2-Nanobody; FIG. 2C. Patient 17, injected with 1.0 mg $^{68}$Ga-HER2-Nanobody.

FIG. 5A. Patient 14 showed the highest tracer uptake (SUV$_{mean}$ 11.8). FIG. 5B. Patient 15 showed moderate tracer uptake, which is easily discernable from background (SUV$_{mean}$ 4.9). FIG. 5C. Patient 6 showed no uptake in the primary lesion (SUV$_{mean}$ 0.9); CT shows a marker clip at the tumor region.

FIGS. 6A-6B: Uptake of $^{68}$Ga-HER2-Nanobody in metastatic lesions on PET/CT fusion images (above) and PET images (below). FIG. 6A. Patient 18 with invaded lymph nodes in the mediastinum and left hilar region. FIG. 6B. Patient 20 with bone metastasis in the pelvis.

FIGS. 7A-7C: Heterogeneous uptake pattern in patient 8, classified as HER2 IHC 2+ but FISH-based on a core needle biopsy. FDG PET images were obtained 6 days prior to $^{68}$Ga-HER2-Nanobody PET. FIG. 7A. Heterogeneous uptake of $^{68}$Ga-HER2-Nanobody in the primary tumor, with a pattern that does not match FDG distribution: area with intense $^{68}$Ga-HER2-Nanobody but weak FDG uptake (arrow); area with faint $^{68}$Ga-HER2-Nanobody but intense FDG uptake (arrowhead). FIG. 7B. Intense $^{68}$Ga-HER2-Nanobody uptake in a bone metastasis located in the coccyx (arrow); absence of uptake in bone metastasis in right iliac bone (arrowhead). FIG. 7C. Low $^{68}$Ga-HER2-Nanobody uptake in muscle (arrow) and lymph node (arrowhead) metastasis.

Figure 2A:
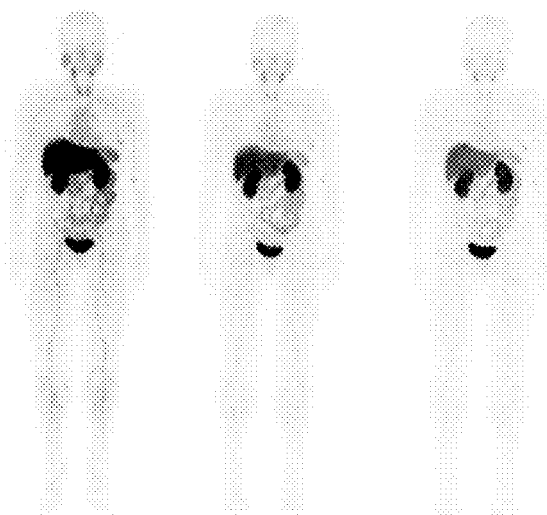
FIGS. 2A-2C: Representative maximum intensity projection (MIP) images at 10, 60 and 90 min p.i. of $^{68}$Ga-HER2-Nanobody for the different mass subgroups.

The following non-limiting Examples describe methods and means according to the invention. Unless stated otherwise in the Examples, all techniques are carried out according to protocols standard in the art. The following examples are included to illustrate embodiments of the invention. Those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Thus, the Figures, Sequence Listing and the Experimental Part/Examples are only given to further illustrate the invention and should not be interpreted or construed as limiting the scope of the invention and/or of the appended claims in any way, unless explicitly indicated otherwise herein.

EXAMPLES

Example 1: Preliminary Analysis of Phase I Study of $^{68}$Ga-HER2-Nanobody ($^{68}$Ga-Anti-HER2 V$_{HH}$) for PET/CT Assessment of HER2-Expression in Breast Cancer The primary objective of this study was the assessment of safety, human biodistribution and dosimetry as well as the evaluation of tumor uptake in HER2-expressing lesions in breast carcinoma patients.

Methods

The anti-HER2 V$_{HH}$ (SEQ ID NO:4) was labeled with $^{68}$Ga via a NOTA derivative (pSCNBnNOTA) with >97% radiolabeling yield after 5 min at RT. In total, 15 female patients with breast carcinoma lesions showing intermediate or high HER2 expression on immunohistochemistry were studied (9/15 showed amplification on FISH analysis).

In one patient, the entire tumor lesion had been removed at the primary biopsy. Among the FISH negative patients, 4/5 still showed V$_{HH}$ uptake. Thus, V$_{HH}$ imaging can identify patients that may benefit from Her2-targeted diagnosis despite an initial FISH negative score (i.e. to "fish" for false FISH negative patients). In patients in which a Her2 signal can be detected using V$_{HH}$ imaging, a repeat biopsy could be performed to perform a second FISH analysis.

Three different study groups (n=5 for each) were included in a dose-escalating step-by-step approach, receiving respectively 0.01, 0.1 and 1.0 mg of anti-HER2 VHH. Radioactive dose was kept constant over the groups and was on average 105±39 MBq. PET/CT scans were performed at 10, 60 and 90 min. Blood and urine samples were analyzed for radioactive content and metabolites. Blood analysis (hematology and clinical chemistry) was performed before and 120 min after tracer injection. Patients were asked for changes in physical and emotional state. Physical examination was performed before and at multiple time points after injection. Biodistribution was analyzed by time activity curves of 10 organs using MIM contouring software in patients with normal liver and kidney function (n=11). Dosimetry was assessed using OLIN DA/EXM.

Results

Radiochemical purity of 68GaHER2 was >98% after purification. No related adverse events were observed during the 24 h follow-up period. Blood analysis showed a fast blood clearance, with on average 10.1±2.2% of injected activity remaining in the total blood volume at 60 min post injection. The compound was stable in vivo (plasma, urine). Tracer uptake at 60 min was highest in liver (10.7±3.6% IA) and kidneys (7.6±0.9% IA) (FIG. 1A), and there was a non-significant trend towards lower liver uptake with higher injected mass (13.0±3.8, 12.5±2.9 and 8.2±2.5% IA for increasing mass). The calculated effective dose was 0.043 mSv/MBq, with the highest doses delivered to the urinary bladder wall and the large intestine wall. SUVmax (maximal standard uptake value) in lesions varied between 0.8 (background) and 7.3. Interestingly, two large lesions (>4 cm) showed a heterogeneous tracer uptake. The heterogeneous pattern was not matched to FDG distribution in one lesion, suggesting it was not due to necrotic areas. For the second lesion, heterogeneous expression of HER2 was confirmed on immunohistochemistry (FIGS. 1B-1C).

The $V_{HH}$ imaging reveals whole-body expression of Her2 in primary tumors and metastases. The Her2 signal that is detected in metastases is hereby often higher than in primary tumor, thus offering the possibility to guide the selection of which (metastatic) lesions are most appropriate for a repeat biopsy ("image-guided biopsy"). In a number of large lesions (>4 cm) a heterogeneous tracer uptake was detected. Hereby, the pattern of heterogeneity in HER2 expression as detected via the Her2 $V_{HH}$'s did not always match the heterogeneity in metabolic activity as detected via FDG distribution, suggesting superiority in identifying optimal areas for a repeat biopsy, thus further fine-tuning the potential for image-guided biopsy.

Remarkably, in one patient, a focal Her2 signal spot was also detected in the brain, showing the possibility to detect Her2 positive brain lesions.

Conclusion

68GaHER2 PET/CT is a safe procedure with a radiation dose comparable to other PET/CT imaging procedures. The wide range in uptake intensity of lesions and the heterogeneous distribution in large lesions show potential for the in vivo assessment of HER2 expression levels.

The results more importantly showed that $V_{HH}$ imaging can accurately identify cancer lesions through specifically binding to a tumor-specific antigen.

In addition, the HER-2 binding VHH's as disclosed herein are able to identify patients that may benefit from Her2-targeted diagnosis despite an initial FISH negative score.

Example 2: Detailed Analysis of Phase I Study of $^{68}$Ga-HER2-Nanobody ($^{68}$Ga-Anti-HER2 $V_{HH}$) for PET/CT Assessment of HER2-Expression in Breast Cancer In the remaining examples sections the term VHH or VHH domain is used interchangeably with the term Nanobody (Nb).

All terms $^{68}$Ga-HER-Nanobody, $^{68}$Ga-NOTA-anti-HER2 Nanobody and $^{68}$Ga-anti-HER2-VHH on the one hand; HER-Nanobody, anti-HER2-Nanobody, HER2-VHH and anti-HER2-VHH on the other hand, refer to the same compound (either labelled with $^{68}$Ga or unlabeled).

Methods

In total, 20 female patients with primary or metastatic breast carcinoma (HER2 IHC 2+ or 3+) were included. Anti-HER2-Nanobody is labeled with $^{68}$Ga via a NOTA derivative. Administered activities were 53-174 MBq (average 107 MBq). PET/CT scans (for dosimetry assessment) were obtained at 10, 60 and 90 min post administration. Physical evaluation and blood analysis were performed for safety evaluation. Biodistribution was analyzed for 11 organs using MIM software; dosimetry was assessed using OLINDA/EXM. Tumor targeting potential was assessed in primary and metastatic lesions.

Results

No adverse reactions occurred. A fast blood clearance was observed, with only 10% of injected activity remaining in the blood at 1 h post injection. Uptake was mainly seen in kidneys, liver, and intestines. The effective dose was 0.043 mSv/MBq, resulting in an average of 4.6 mSv per patient. The critical organ was the urinary bladder wall with a dose of 0.406 mGy/MBq. In patients with metastatic disease, tracer accumulation well above background was demonstrated in the majority of identified sites of disease. Primary lesions were more variable in tracer accumulation.

Conclusion $^{68}$Ga-HER2-Nanobody PET/CT is a safe procedure with a radiation dose comparable to other routinely used PET tracers. Its biodistribution is favorable, with the highest uptake in kidneys, liver and intestines, but very low background levels in all other organs that typically house primary breast carcinoma or tumor metastasis. Tracer accumulation in HER2-positive metastases is high, compared to normal surrounding tissues, and warrants further assessment in a phase II trial.

Materials and Methods

Study Design

This was an open-label phase I study in HER2-expressing breast carcinoma patients (n=20). The supplemental data as represented in Example 3 provide details on patient selection and approvals. Three subgroups, receiving respectively 0.01 mg (group 1: pt 1-7), 0.1 mg (group 2: pt 8-15) and 1.0 mg (group 3: pt 16-20) NOTA-Anti-HER2-Nanobody were evaluated. The activity administered was similar for the different patient groups and ranged between 53 and 174 MBq.

Imaging Methods and Safety Assessment

Details on radioligand synthesis, safety assessment and PET/CT protocol are described in the supplemental data represented in Example 3.

A p-SCN-Bn-NOTA chelator was conjugated to the Nanobody. $^{68}$Ga (250-400 MBq) was incubated with the NOTA-Anti-HER2-Nanobody in acid conditions for 5-7 min at room temperature. $^{68}$Ga-HER2-Nanobody was purified and filtered prior to injection. Quality controls included analysis of appearance, presence of $^{68}$Ge, pH, radiochemical purity and radiochemical identity, filter integrity (bubble point test). For the different patient groups the necessary amount of cold NOTA-anti-HER2-Nanobody was added prior to final filtration.

$^{68}$Ga-HER2-Nanobody was injected as an intravenous bolus. For safety evaluation, vital sign were recorded and clinical laboratory testing was performed before and 2 h after injection. Subjective adverse experiences were assessed using open questions up to 24 h post injection (p.i.). Whole body PET/CT imaging (low-dose CT) was performed with a Philips Gemini TF at 10, 60 and 90 minutes p.i.

Summary Blood, Urine and Image Analysis

Details on image processing and analysis as well as blood and urine analysis are described in the supplemental data, (see Example 3).

Blood samples were obtained at different time points p.i., assessed for radioactive content and expressed as a percentage of the injected activity (% IA) in total blood volume using Nadler's formula. Urine samples were collected at about 45 min and 2 h p.i. Blood and urine were assessed for metabolites.

Uptake in 11 organs (liver, kidneys, intestines, thyroid, whole body, bladder and urinary activity in ureters, spleen, heart muscle, lungs, hematopoietic bone marrow and breast tissue) was measured on each PET/CT using MIM contouring software (MIM-software Inc.) and expressed as % IA. Dosimetric calculations for the adult female were made using the OLINDA/EXM software 1.0 (16).

Uptake in tumor lesions was measured using the mean Standard Uptake Value ($SUV_{mean}$) in a 10 mm spheroid Region of interest (ROI) positioned over the area with the highest uptake. If available, the uptake in the primary lesion and in the metastasis showing the highest $SUV_{mean}$ is reported.

Results

Patient Characteristics

Between April 2012 and July 2014, 20 patients completed the study protocol. The patients received on average 107±37 MBq (range 53-174 MBq)$^{68}$Ga-HER2-Nanobody. Patient and study drug characteristics are summarized in table 3.

TABLE 3

Patient characteristics

| | Patient no. | Age | Injected activity (MBq) | Tumor type | ER/PR | HER2 IHC | HER2 FISH (ratio; copies/cell) | Primary tumor | (Range of) SUV$_{mean}$ of lesion(s) Local ADP | Distant M+ (type) |
|---|---|---|---|---|---|---|---|---|---|---|
| 0.01 mg | 1 | 43 | 77 | IDC | +/+ | 2+ | + (2.2; 6.2) | ISR* | A | A |
| | 2 | 60 | 66 | IDC | +/+ | 3+ | + (>2; macroclusters) | CR | A | 3.1 (bone) |
| | 3 | 68 | 53 | IDC | +/+ | 3+ | + (12.2; 20.0) | 3.2 | A | A |
| | 4 | 53 | 76 | IDC | +/+ | 2+ | − (1.3; 3.7) | 2.2 | A | A |
| | 5 | 74 | 84 | IDC | +/+ | 2+ | − (1.3; 3.8) | 2.3 | A | A |
| | 6 | 34 | 83 | IMeC | +/− | 3+ | + (2.8; 8.0) | 0.9 | A | A |
| | 7 | 34 | 80 | IDC | +/+ | 2+ | − (1.0; 1.4) | 2.0 | A | A |
| 0.1 mg | 8 | 67 | 92 | IDC | +/+ | 2+ | − (1.4; 3.4) | 5.0 | 3.2-4.3 | 1.0-5.6 (bone) |
| | 9 | 57 | 111 | IDC | +/+ | 3+ | + (1.3; 6.1) | 2.3 | A | A |
| | 10 | 61 | 100 | IDC | +/− | 3+ | + (9.4; 15.0) | SR | SR | 4.1-5.7 (bone) |
| | 11 | 65 | 90 | IDC | +/+ | 3+ | + (2.3; 5.1) | 2.9 | 6.3 | A |
| | 12 | 46 | 82 | IDC | +/+ | 3+ | + (8.1; 15.6) | 1.4 | A | A |
| | 13 | 32 | 153 | IDC | −/− | 2+ | + (9.4; 17.4) | 3.2 | 1.7 | A |
| | 14 | 53 | 103 | IDC | −/− | 3+ | + (4.7; 9.2) | 11.8 | 13.0 | A |
| | 15 | 78 | 148 | IDC | +/+ | 2+ | − (1.0; 2.1) | 4.9 | A | A |
| 1.0 mg | 16 | 76 | 96 | ILC | +/+ | 2+ | − (1.0; 1.7) | SR | SR | 2.2-3.9 (bone) |
| | 17 | 74 | 138 | IDC | −/− | 2+ | − (1.2; 4.3) | 1.8 | A | A |
| | 18 | 62 | 167 | IDC | +/− | 2+ | + (2.6; 4.5) | SR | SR | 3.5-6.0 (ADP mediastinum) |
| | 19 | 62 | 174 | IMiC | +/+ | 2+ | + (2.8; 8.0) | 4.4 | 5.1-5.9 | 3.6-3.9 (bone) |
| | 20 | 48 | 170 | IDC | +/+ | 3+ | + (7.8; 15.6) | 0.7† | A | 4.7-5.4 (bone)† |

IDC = invasive ductal carcinoma;
ILC = Invasive lobular carcinoma;
ER = estrogen receptor;
PR = progesterone receptor;
IMeC = Invasive medullary carcinoma;
IMiC = Invasive Mixed carcinoma;
ADP = adenopathy;
ISR = incomplete surgical removement;
SR = surgically removed; A = Absent;
*= patient was scanned after incomplete surgical removement but additional surgical resection could not demonstrate remaining tumor cells;
†= after 4 cycles of epirubicine-cyclophosphamide;

Safety Assessment

After the administration of $^{68}$Ga-HER2-Nanobody, no symptoms or signs were reported. Clinical laboratory testing of blood, taken before and 120 min after injection, showed no significant changes that could be related to the study drug.

Pharmacokinetics and Biodistribution

Figure 2B:
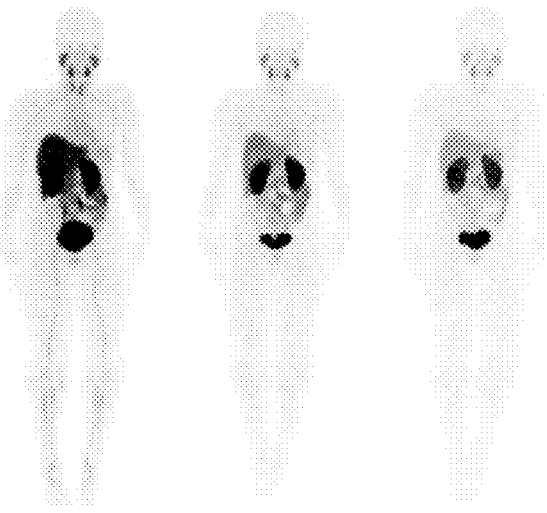
Figure 2C:
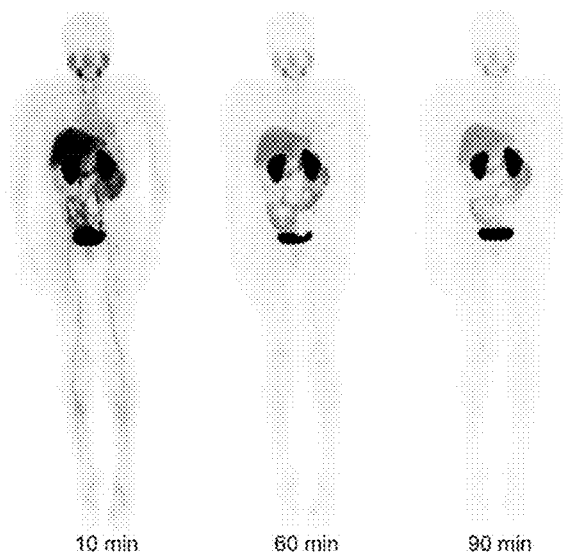

FIGS. 2A-2C show images of representative patients for each subgroup. No obvious differences in biodistribution were noted between different subgroups by visual comparison. Blood pool activity is only visible at 10 min after injection, with weak delineation of the heart and large blood vessels. Uptake is mainly seen in kidneys, liver and intestines. This uptake pattern is already present at the 10 min images and decreases over time. Weak uptake is seen in glandular tissues, such as thyroid, pituitary, salivary, lacrimal and sweat glands.

Figure 3:
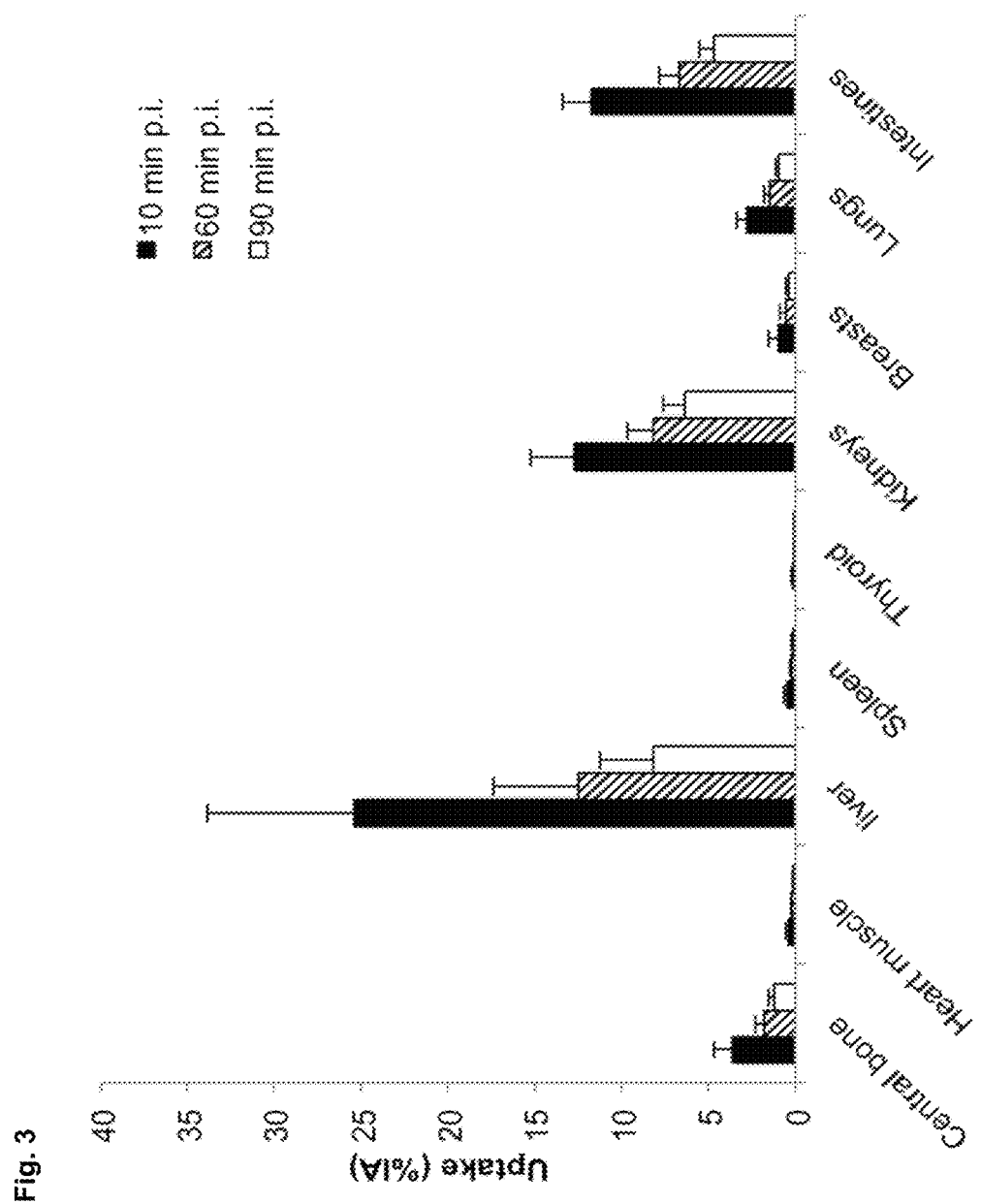
FIG. 3: Uptake, expressed in % of injected activity (% IA) in the indicated organs at 10, 60 and 90 min p.i. (n=18).
Figure 4:
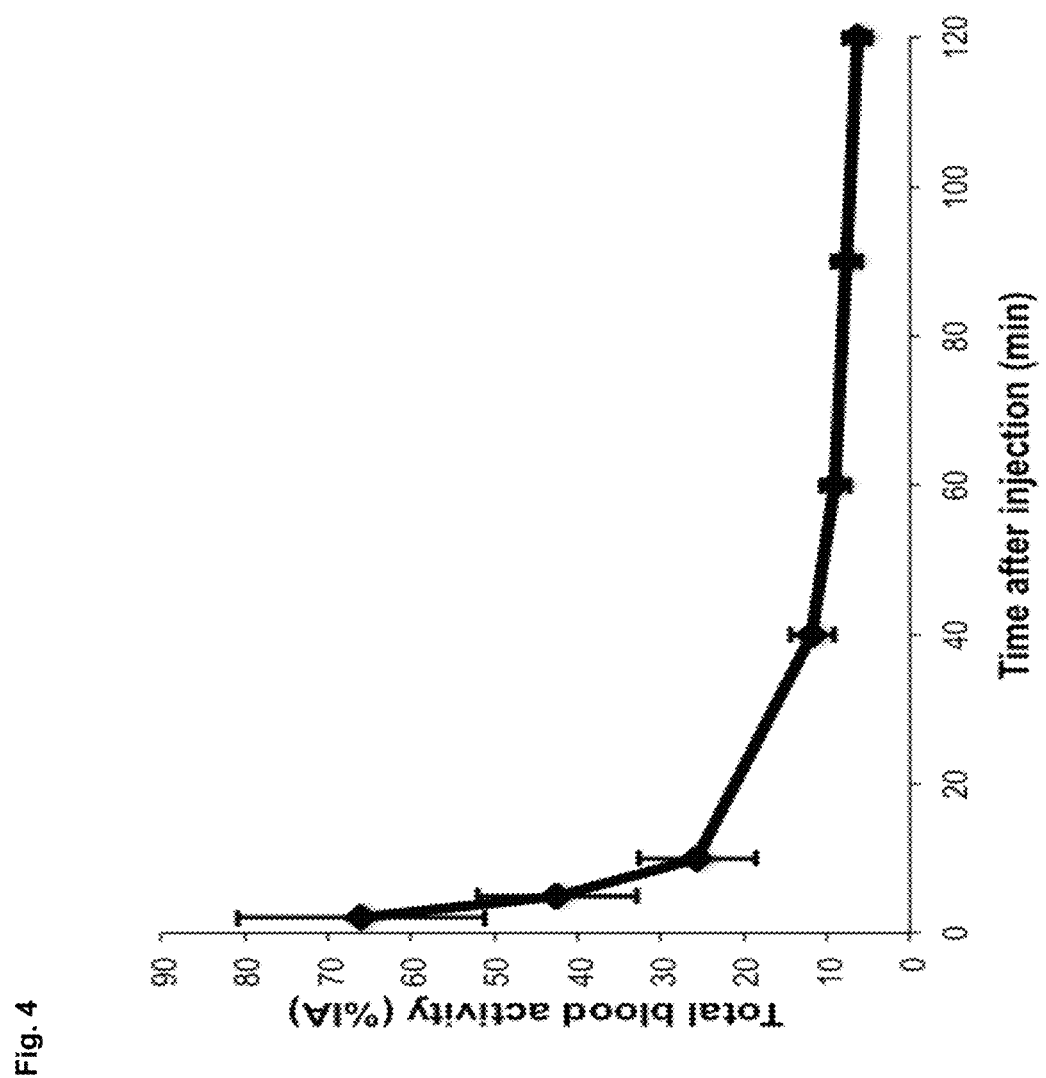
FIG. 4: Time-activity curve of total blood activity, expressed in % of injected activity (% IA). Mean and standard deviation of 12 patients are represented.

The uptake of $^{68}$Ga-HER2-Nanobody in individual organs is presented in FIG. 3 and Table 4. Blood pool activity is presented in FIG. 4. A fast blood clearance is seen, with only 10% of injected activity remaining in the blood at 1 h p.i. Blood half-lives were calculated at 2.9 min (early phase) and 25.5 min (late phase). Plasma curves were identical to blood curves, indicating that the tracer was not associated to blood cells (data not shown). No metabolites were detected in blood up to 10 min or urine up to 2 h p.i.

TABLE 4

Uptake of $^{68}$Ga-HER2-Nanobody in single organs.

| | Uptake (% IA) | | |
|---|---|---|---|
| Organ | 10 min | 60 min | 90 min |
| Liver | 25.41 ± 8.39 | 12.47 ± 4.88 | 8.18 ± 3.07 |
| Kidneys | 12.74 ± 2.5000 | 8.14 ± 1.55 | 6.36 ± 1.23 |
| Intestines | 11.76 ± 1.62 | 6.72 ± 1.11 | 4.72 ± 0.80 |
| Central bone | 3.65 ± 1.02 | 1.80 ± 0.53 | 1.20 ± 0.37 |
| Lungs | 2.83 ± 0.56 | 1.48 ± 0.33 | 0.98 ± 0.18 |
| Breasts | 1.00 ± 0.54 | 0.58 ± 0.31 | 0.39 ± 0.19 |
| Spleen | 0.48 ± 0.16 | 0.22 ± 0.09 | 0.15 ± 0.07 |
| Heart muscle | 0.40 ± 0.12 | 0.19 ± 0.06 | 0.12 ± 0.04 |
| Thyroid | 0.12 ± 0.08 | 0.05 ± 0.03 | 0.03 ± 0.02 |

Figure 8:
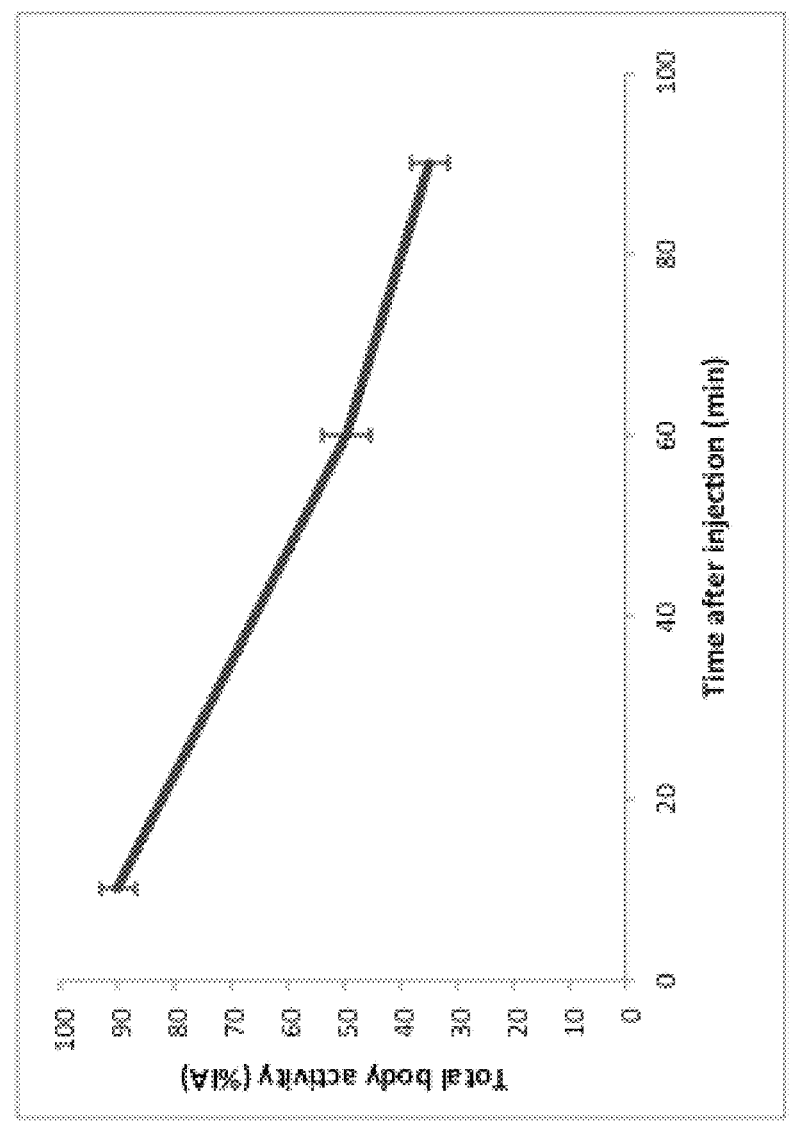
FIG. 8: Total body activity over time, represented as the average and standard deviation of 18 patients with normal renal and hepatic function. At 1 h after injection, 50% of the tracer had been eliminated from the body.

All images showed uptake in kidneys and excretion of the tracer into the urine. Although liver and intestinal uptake was visible, there were no signs of hepatobiliary excretion, such as accumulation in the gall bladder or duodenum. At 1 h p.i., 50% of the tracer had been eliminated from the body, resulting in an estimated biological half-life of 1 h (FIG. 8).

Effect of Injected Mass on Liver Uptake

Based on preclinical results, an effect of the injected mass of the compound on the non-specific binding was expected. Therefore, liver uptake was assessed in the three patient subgroups receiving different amounts of Nanobody mass. Overall, liver uptake was quite variable between patients. There is a trend towards lower liver uptake at 90 min p.i. or the 1.0 mg mass group, with an average uptake of 5.5% IA compared to 9.0 and 9.5% IA for 0.1 and 0.01 mg respectively, but with overlapping 95% confidence intervals (3.3-7.6; 5.7-12.3 and 7.4-11.5 respectively). A one-way ANOVA indicates no significant difference, $F(2,15)=3.60$, $p=0.053$.

The findings that the background liver uptake is inherently quite variable between patients and that there is a lack of significant correlation of liver uptake with the amount of injected Nanobody mass indicate that imaging in human patients can be performed using low amounts of injected mass and that, despite the expectations based on preclinical data, there is no benefit or need to increase the injected mass.

Dosimetry

Table 5 summarizes the individual organ doses and individual effective dose (ED) results for all subjects with normal liver and renal function. The urinary bladder wall shows the highest organ dose of 0.406 mGy/MBq, followed by the kidneys (0.216 mGy/MBq), liver (0.0778 mGy/MBq), lower large intestine wall (0.0759 mGy/MBq) and upper large intestine wall (0.0619 mGy/MBq).

uptake pattern, indicating it was not caused by necrotic tumor areas. The patient presented with diffuse metastases, of which some but not all lesions showed uptake above background ($SUV_{mean}$ range 1.0-5.6; FIGS. 7B-7C).

Conclusion $^{68}$Ga-HER2-Nanobody PET/CT is a safe procedure with a radiation dose comparable to other routinely used PET tracers. Its biodistribution is favorable, with the highest uptake in kidneys, liver and intestines, but very low background levels in all other organs that typically house primary breast carcinoma or tumor metastasis. Tracer accumulation in metastases of HER2 overexpressing patients is high, compared to normal surrounding tissues, and warrants further assessment in a phase II trial.

TABLE 5

Organ doses and effective doses.

| Patient no. | Urinary Bladder Wall | Kidneys | Liver | LLI Wall | ULI Wall | Thyroid | Effective dose (mSv/MBq) |
|---|---|---|---|---|---|---|---|
| 1 | 0.406 | 0.191 | 0.0515 | 0.0843 | 0.0606 | 0.0233 | 0.0425 |
| 3 | 0.406 | 0.161 | 0.114 | 0.0757 | 0.0679 | 0.0326 | 0.0458 |
| 4 | 0.405 | 0.219 | 0.0788 | 0.0295 | 0.0787 | 0.0257 | 0.0371 |
| 5 | 0.407 | 0.181 | 0.116 | 0.0962 | 0.0566 | 0.0093 | 0.0472 |
| 6 | 0.406 | 0.297 | 0.0957 | 0.0798 | 0.0535 | 0.0282 | 0.0453 |
| 7 | 0.405 | 0.259 | 0.0788 | 0.0423 | 0.0840 | 0.0020 | 0.0371 |
| 8 | 0.405 | 0.141 | 0.114 | 0.0788 | 0.0715 | 0.0137 | 0.0433 |
| 9 | 0.406 | 0.273 | 0.0740 | 0.0686 | 0.0675 | 0.0200 | 0.0421 |
| 10 | 0.406 | 0.229 | 0.0922 | 0.0626 | 0.0991 | 0.0035 | 0.0425 |
| 12 | 0.407 | 0.220 | 0.0594 | 0.0816 | 0.0772 | 0.0327 | 0.0435 |
| 13 | 0.406 | 0.225 | 0.113 | 0.0632 | 0.0812 | 0.0496 | 0.0442 |
| 14 | 0.407 | 0.222 | 0.0849 | 0.0719 | 0.113 | 0.0513 | 0.0448 |
| 15 | 0.406 | 0.278 | 0.0719 | 0.0086 | 0.0071 | 0.0035 | 0.0335 |
| 16 | 0.407 | 0.192 | 0.0473 | 0.140 | 0.0356 | 0.0124 | 0.0485 |
| 17 | 0.407 | 0.216 | 0.0610 | 0.141 | 0.0518 | 0.0132 | 0.0504 |
| 18 | 0.406 | 0.193 | 0.0583 | 0.118 | 0.0554 | 0.0110 | 0.0469 |
| 19 | 0.406 | 0.181 | 0.0422 | 0.0087 | 0.0067 | 0.0220 | 0.0317 |
| 20 | 0.406 | 0.211 | 0.0469 | 0.116 | 0.0464 | 0.0177 | 0.0447 |
| Mean ± SD | 0.406 ± 0.001 | 0.216 ± 0.041 | 0.0778 ± 0.0252 | 0.0759 ± 0.0384 | 0.0619 ± 0.0274 | 0.0207 ± 0.0143 | 0.0428 ± 0.0050 |

Patient no. 2 and 11 were not taken into account because of altered liver and/or kidney function.
LLI = Lower large intestines; ULI = Upper large intestines.
Organ dose (mGy/MBq)

Uptake in Tumor Lesions

Uptake in tumor lesions could be evaluated in 19 patients, 9 of which only had a primary lesion, six both a primary lesion and local or distant metastases, and 4 only local or distant metastases (Table 5).

Uptake in Primary Lesions

Figures 5A, 5B, 5C:
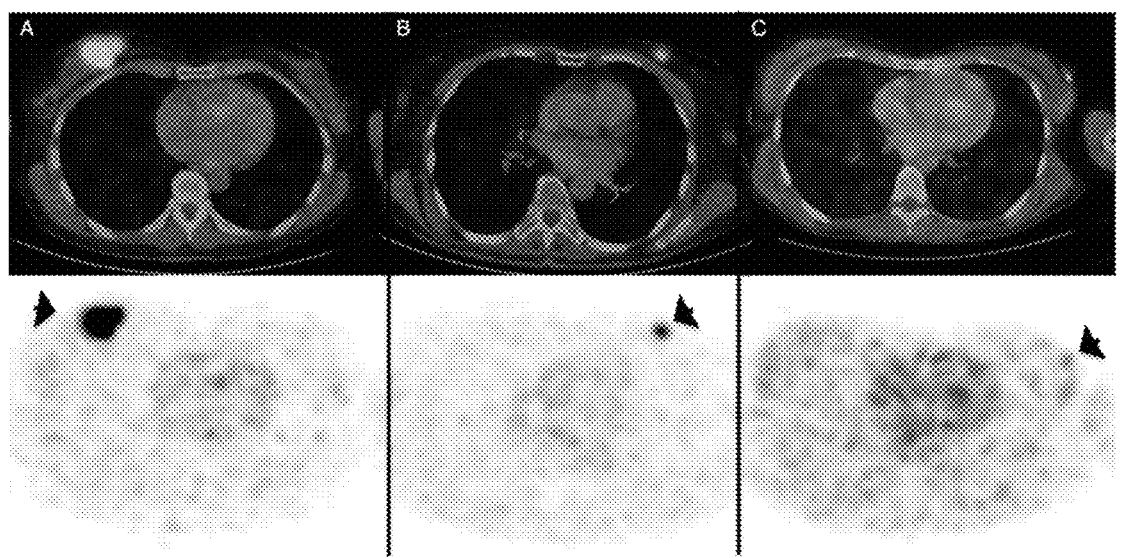
FIGS. 5A-5C: Uptake of $^{68}$Ga-HER2-Nanobody in primary breast carcinoma lesions. Tracer uptake in primary lesions is shown on fusion images (top row) and PET images (bottom row) with the lesion indicated by black arrows.

Tracer uptake was visible above background in the majority of primary tumors, with $SUV_{mean}$ values ranging between 0.7 and 11.8. Uptake was absent in the primary tumor of two patients (no. 6 and 20). Representative images showing $^{68}$Ga-HER2-Nanobody uptake in primary lesions are presented in FIGS. 5A-5C.

Uptake in Local and Distant Metastases

All patients with metastatic lesions showed clear tracer accumulation in at least one lesion, with $SUV_{mean}$ ranging from 3.1 to 6.0. FIGS. 6A-6B show images of patients 18 and 20 with metastases in thoracic lymph nodes and the pelvis respectively.

Heterogeneous Uptake Pattern

In patient 8, a heterogeneous uptake pattern was observed in the primary tumor (FIGS. 7A-7C). The uptake pattern did not match the [$^{18}$F]Fluoro-2-deoxy-2-D-glucose (FDG)

Example 3: Supplemental Data for the Phase I Study of $^{68}$Ga-HER2-Nanobody ($^{68}$Ga-Anti-HER2 $V_{HH}$) for PET/CT Assessment of HER2-Expression in Breast Carcinoma Supplemental methods in addition to the details set out in Example are set out hereunder.

Approvals

The Belgian federal agency for medicines and health products, the regional ethics committee of UZ Brussel and the radiation protection agency of Belgium approved this study. The study was conducted in accordance with the Declaration of Helsinki and the International Conference on Harmonization Guidelines for Good Clinical Practice. Written informed consent was obtained from all participants. The study was registered as a clinical trial with the identifier EudraCT 012-001135-31.

Patient Characterization and Study Subgroups

Twenty adult female breast carcinoma patients with local, locally advanced or metastatic breast carcinoma that showed a moderate or high expression of HER2 on immunohistochemistry (2+ or 3+) were included in the study. Patients were allowed to enter the study at first diagnosis, at relapse or under treatment (with the exclusion of any HER2-targeted treatment) if there was at least one documented breast carcinoma lesion. No additional work-up for the detection of potential additional metastasis was required for this study, since tumor targeting potential was not the primary aim. Exclusion criteria were male gender, pregnancy, breast feeding, HER2-targeted therapy in the last 30 days before administration, known abnormal liver or kidney function, serious active infection, recent gastro-intestinal disorder with diarrhea, other life-threatening illness, unability to communicate reliably or give informed consent, patients unlikely to cooperate with the requirements of the study or patients who already participated in the study.

Three subgroups of patients, receiving respectively 0.01 mg (group 1: pt 1-7), 0.1 mg (group 2: pt 8-15) and 1.0 mg (group 3: pt 16-20) $^{68}$Ga-HER2-Nanobody were evaluated for a potential difference in normal biodistribution, to investigate a potential decrease in non-specific binding in non-target organs with increasing mass of tracer.

The activity administered was similar for the different patient groups and ranged between 66 and 174 MBq (the allowed range was 37-185 MBq).

Patients 2 and 11 were withdrawn from the biodistribution and dosimetry study because of decreased renal function and altered liver enzymes, >1.5× normal values at time of imaging. Their images are however evaluated for tumor targeting potential.

Safety Assessment

For safety evaluation, all patients underwent vital signs measurement (blood pressure, heart rate and temperature), clinical laboratory testing (standard hematologic and comprehensive metabolic panels that included hemoglobin, white blood cells, neutrophils, lymphocytes, platelets, creatinine, blood urea nitrogen, calcium, sodium, potassium, carbon dioxide, lactate dehydrogenase, alanine transaminase, aspartate aminotransferase, alkaline phosphatase, total bilirubin, and albumin), before administration, as well as 2 h after injection of the compound. Subjective adverse experiences were assessed using open questions before injection, throughout the 2 h that patients were present in the nuclear medicine department and using telephone follow-up at 24 h post-injection Conjugation of p-SCN-Bn-NOTA to Anti-HER2 Nanobody The anti-HER2 Nanobody was produced according to GMP standards. In order to allow complexation of the $^{68}$Ga radiometal, a p-SCN-Bn-NOTA chelator was conjugated to the Nanobody as described earlier in Xavier C, Vaneycken I, D'Huyvetter M, et al. Synthesis, preclinical validation, dosimetry, and toxicity of $^{68}$Ga-NOTA-anti-HER2 Nanobodies for iPET imaging of HER2 receptor expression in cancer. J Nuci Med. 2013; 54:776-784. Briefly, Nanobody in 0.05 M sodium carbonate buffer pH 8.7 was added to p-SCN-Bn-NOTA (10-fold molar excess) and incubated for 2 h at room temperature. The coupling reaction was quenched by adjusting the pH to 7-7.4 using HCl 1 N. The conjugate was then purified by size-exclusion chromatography (SEC) on a Superdex 75 10/300 GL (GE Healthcare) using ammonium acetate 0.1 M pH 7 as eluent or 0.01 M PBS.

Synthesis of $^{68}$Ga-HER2-Nanobody $^{68}$Ga was obtained from a $^{68}$Ge/$^{68}$Ga generator (Eckert and Ziegler), eluted with 0.1N HCl (Merck). The 1.5 ml peak fraction (250-400 MBq) was added to 1 M sodium acetate buffer pH5 (1 ml) containing NOTA-Anti-HER2 Nanobody (1.1-3.8 nmol), the final pH was 4-4.5. The reaction mixture was incubated for 5-7 min at room temperature. Next, the product was purified by gel filtration on a disposable PD10 column (GE Healthcare), equilibrated with 0.01 M PBS pH 7.4. The compound was finally filtered through a 0.22 μm membrane filter (13 mm, Millipore, Brussels, Belgium).

The final solution was analyzed by instant thin layer chromatography (iTLC-SG) performed on silica gel (SG) (Agilent) using 0.1 M sodium citrate pH 5.0 as eluent to evaluate radiochemical purity. ITLC-SG: $^{68}$Ga-HER2-Nanobody $R_f$=0, unbound $^{68}$Ga $R_f$=1. The final product was also analyzed by reverse phase high performance liquid chromatography (RP-HPLC) using a polystyrene divinylbenzene copolymer column (PLRP-S 300 Å) to evaluate radiochemical purity and radiochemical identity. RP-HPLC: $t_R$=12.8 min.

In addition, quality control of $^{68}$Ga-HER2-Nanobody involved analysis of appearance of the solution, radionuclide identity (gamma spectrum), presence of $^{68}$Ge, pH, filter integrity (bubble point test), endotoxin (LAL test) and sterility (microbiology).

For the different patient groups different masses of $^{68}$Ga-HER2-Nanobody were injected (0.01 mg/0.1 mg/1 mg). For the higher masses, the necessary amount of cold NOTA-anti-HER2 Nanobody (in 0.01M PBS pH7.4) was added to the $^{68}$Ga-HER2-Nanobody prior to final filtration.

$^{68}$Ga-HER2-Nanobody PET/CT Imaging

Images were acquired using a Philips Gemini TF PET/CT (LySO-based PET scanner with Time-of-flight with 18 cm axial and 70 cm transaxial field-of-view (FOV), 64-slice CT). The scanner is accredited by the EANM via the EARL program.

Whole-body images were acquired 10, 60 and 90 minutes after administration of $^{68}$Ga-HER2-Nanobody. The time per bed position was 1 min (for a total scan time of about 25 min).

Low-dose CT was performed for attenuation correction and localization of hotspots on PET, consisting of slices of 512 by 512 pixels (FOV: 600 mm) at 5 mm slice thickness, acquired at 120 kV and 50 mAs, resulting in a radiation dose (CTDI) of 2.9 mGy/scan.

PET images were reconstructed to 144×144 matrix with 4 mm slice thickness (4 mm isotropic pixels) using the vendor's standard BLOB-OS-TOF reconstruction with 3 iterations and 33 subsets (at a kernel width of 14.1 cm) with attenuation, scatter and randoms correction.

Blood and Urine Samples

Blood samples were taken from a peripheral vein at 2, 5, 10 and 40 min, and at 1 and 2 h post injection (p.i.) of the compound. Urine sample were collected at about 45 min and 2 h p.i.

Whole blood and plasma samples were counted against appropriate standards of known dilution in an automatic gamma well counter and, after correction for decay and background activity, expressed as a percentage of the injected activity (% IA). The blood volume of each volunteer was estimated according to body weight and height, using Nadler's formula and the patient's hematocrit. Blood activity results of 8 patients were not further used in the analysis because of altered liver or kidney tests (no. 2, 11), because of injection of the tracer and blood sampling on the same arm (no. 10, 16, 18, 19, 20), or because of possible interference with $^{99m}$Tc blood activity due to a cardiac blood pool scan two days prior to this study (no. 14). Blood half-lives were calculated with a two-phase exponential decay model using GraphPad Prism software (GraphPad Software, La Jolla, Calif., USA). Plasma and urine aliquots were analyzed by SEC or RP-HPLC to identify possible metabolites.

Volume-of-Interest Definition

The $^{68}$Ga-HER2-Nanobody uptake in different organs was determined using Region of Interests (ROIs), drawn using MIM contouring software (MIM software Inc., 2014). For biodistribution and dosimetry purposes, organs with tracer uptake were delineated in a semi-automatic (region grow) fashion and manually corrected to assure that the activity on the PET images that was contributing to the organ was included in the ROI (kidneys, intestines, thyroid, whole body, bladder and urinary activity in urethra). For 5 organs not showing substantial tracer uptake, organ delineation was based on CT data (spleen, heart muscle, lungs, central bone (covering bone from top of the skull until proximal femora and representing hematopoietic bone marrow) and unaffected breast). Care was taken that activity originating from kidneys, liver, intestines, bladder and urine was not included into the CT-based ROI's. To reflect normal biodistribution in breast tissue, the activity in the unaffected breast was multiplied by two. For assessment of liver activity, the liver volume was determined using CT-based delineation and multiplied by the average activity in liver parenchyma, as determined by a spheroid ROI of 40 mm diameter, positioned in the right liver lobe. This approach was chosen to overcome the influence of potential motion artifacts in the liver due to breathing or inhomogeneity in liver activity due to underlying liver metastasis.

Dosimetry

For dosimetric calculations, the OLINDA/EXM software 1.0 (Organ Level Internal Dose Assessment/EXponential Modeling, Vanderbilt University) was used (Stabin M G, Sparks R B, Crowe E. OLINDA/EXM: the second-generation personal computer software for internal dose assessment in nuclear medicine. *J Nucl Med.* 2005; 46:1023-1027.). OLINDA/EXM software entails the EXM code that performs kinetic analysis of biokinetic data for input into the dose calculations algorithms. The organ uptake values per patient were put into the EXM analysis software and a bi-exponential fit was performed per organ for each individual patient. OLINDA subsequently calculates the disintegrations per source organ as well as the radiation dose for all target organs from these data. Other input variables were the excretion parameters, put at 100% renal excretion with a biological half-life of 60 min and a voiding bladder interval of 60 min.

Uptake in Tumor Lesions

A sphere-shaped ROI with a diameter of 10 mm was placed within each discernable tumor lesion that measured at least 10 mm on the low dose CT, obtained for study purposes, or on other available imaging data, using MIM contouring software. For large lesions, the ROI was positioned over the area with the highest uptake. The mean Standard Uptake Value ($SUV_{mean}$), corrected for the body weight, within this ROI is reported as the uptake value for a lesion. If available, the uptake in the primary lesion and in the metastasis showing the highest $SUV_{mean}$ is reported. Osirix software (Pixmeo) was used for image processing.

Statistical Analysis

Values are reported as mean±standard deviation (SD). A one-way ANOVA was conducted to compare the effect of injected Nanobody mass (3 patient subgroups) on the tracer uptake in liver.

The invention claimed is:

1. A method for identifying a HER-2 positive metastatic brain lesion in a human subject, comprising
   (a) selecting a human subject previously identified as having cancer,
   (b) administering to the subject of step (a) a radiolabelled heavy chain antibody ($V_{HH}$) or a functional fragment thereof, which specifically binds to HER2, wherein the amino acid sequence of said $V_{HH}$ or functional fragment thereof comprises the combination of a CDR1 region having SEQ ID NO: 1, a CDR2 region having SEQ ID NO: 2, and a CDR3 region having SEQ ID NO: 3, and
   (c) measuring using PET/CT imaging the ability of said $V_{HH}$ or functional fragment thereof to bind HER2 in the brain of the subject,
   wherein the $V_{HH}$ or a functional fragment thereof is labelled with a radioisotope selected from the group consisting of 68Ga, 18F, 64Cu, 86Y, 76Br, 82Rb, 209At, and 210At,
   wherein the subject is identified as having a HER-2 positive metastatic brain lesion when the $V_{HH}$ or functional fragment thereof binds to HER2 in the brain of the subject.

2. The method of claim 1, wherein said $V_{HH}$ or functional fragment thereof is labelled with a radioisotope selected from the group consisting of 68Ga, and 64Cu.

3. The method of claim 1, wherein said $V_{HH}$ or functional fragment thereof has at least 80% amino acid identity with the amino acid sequence of SEQ ID NO: 4, or a functional fragment thereof.

4. The method of claim 1, wherein said subject of step (a) was previously identified as having breast cancer.

5. The method of claim 1, wherein said $V_{HH}$ or functional fragment thereof is administered intravenously or intraperitoneally.

6. The method of claim 1, wherein said $V_{HH}$ or functional fragment thereof is in a monovalent format.

7. The method of claim 1, wherein said $V_{HH}$ has an amino acid sequence set forth as SEQ ID NO: 4, or a functional fragment thereof.

8. The method of claim 1, wherein said $V_{HH}$ or functional fragment thereof is labelled with 68Ga.

9. The method of claim 1, wherein said $V_{HH}$ or functional fragment thereof is formulated to provide a calculated mean effective dose of between 0.002 and 0.1 mSv/MBq in said human subject.

10. The method of claim 1, wherein the radioisotope has a physical half-life of less than two hours.

11. The method of claim 1, wherein the $V_{HH}$ or a functional fragment thereof further comprises a chelating agent.

12. The method of claim 11, wherein the chelating agent is selected from the group consisting of 1,4,7-triazacyclononane-N-succinic acid-N',N''-diacetic acid (NODASA), 1,4,7-triazacyclononane-N-glutamic acid-N',N''-diacetic acid (NODAGA), 1,4,7,10-tetraazacyclododecane-1,4,7,10-tetraacetic acid (DOTA), 1,4,7-triazacyclononane-1,4,7-triacetic acid (NOTA), and derivatives thereof.

13. A method for identifying a HER-2 positive cancer lesion in a human subject, comprising
   (a) selecting a human subject initially identified as HER-2 negative in a standard in vitro assay for identifying a HER-2 positive cancer lesion,
   (b) administering to the subject of step (a) a radiolabelled heavy chain antibody ($V_{HH}$) or a functional fragment thereof, which specifically binds to HER2, wherein the amino acid sequence of said $V_{HH}$ or functional fragment thereof comprises the combination of a CDR1 region having SEQ ID NO: 1, a CDR2 region having SEQ ID NO: 2, and a CDR3 region having SEQ ID NO: 3, and
   (c) measuring using PET/CT imaging the ability of said $V_{HH}$ or functional fragment thereof to bind HER2 in the subject, wherein the $V_{HH}$ or a functional fragment thereof is labelled with a radioisotope selected from the group consisting of 68Ga, 18F, 64Cu, 86Y, 76Br, 82Rb, 209At, and 210At, wherein the subject is identified as having a HER-2 positive cancer lesion when the $V_{HH}$ or functional fragment thereof binds to HER2 in the subject.

14. The method of claim 13, wherein the standard in vitro assay is a FISH assay for Her2 gene amplification.

15. The method of claim 14, wherein the subject of step (a) was initially diagnosed to be HER-2 negative in the FISH assay by yielding a score of less than about 2.0.

16. The method of claim 13, wherein said $V_{HH}$ or functional fragment thereof is labelled with a radioisotope selected from the group consisting of 68Ga, 18F, and 64Cu.

17. The method of claim 13, wherein said $V_{HH}$ or functional fragment thereof has at least 80% amino acid identity with the amino acid sequence of SEQ ID NO: 4, or a functional fragment thereof.

18. The method of claim 13, wherein said cancer lesion is a breast cancer lesion.

19. The method of claim 13, wherein said $V_{HH}$ or functional fragment thereof is administered intravenously or intraperitoneally.

20. The method of claim 13, wherein said $V_{HH}$ or functional fragment thereof is in a monovalent format.

21. The method of claim 13, wherein said $V_{HH}$ has an amino acid sequence set forth as SEQ ID NO: 4, or a functional fragment thereof.

22. The method of claim 13, wherein said $V_{HH}$ or functional fragment thereof is labelled with 68Ga.

23. The method of claim 13, wherein said $V_{HH}$ or functional fragment thereof is formulated to provide a calculated mean effective dose of between 0.002 and 0.1 mSv/MBq in said human subject.

24. The method of claim 13, wherein the radioisotope has a physical half-life of less than two hours.

25. The method of claim 13, wherein the $V_{HH}$ or a functional fragment thereof further comprises a chelating agent.

26. The method of claim 25, wherein the chelating agent is selected from the group consisting of 1,4,7-triazacyclononane-N-succinic acid-N',N''-diacetic acid (NODASA), 1,4,7-triazacyclononane-N-glutamic acid-N',N''-diacetic acid (NODAGA), 1,4,7,10-tetraazacyclododecane-1,4,7,10-tetraacetic acid (DOTA), 1,4,7-triazacyclononane-1,4,7-triacetic acid (NOTA), and derivatives thereof.

27. A method for a performing positron emission tomography (PET) imaging study in a human subject, comprising
(a) administering to the subject a radiolabelled heavy chain antibody ($V_{HH}$) or a functional fragment thereof, which specifically binds to HER2, wherein the amino acid sequence of said $V_{HH}$ or functional fragment thereof comprises the combination of a CDR1 region having SEQ ID NO: 1, a CDR2 region having SEQ ID NO: 2, and a CDR3 region having SEQ ID NO: 3, wherein the $V_{HH}$ or a functional fragment thereof is labelled with a radioisotope selected from the group consisting of 68Ga, 18F, or 64Cu; and
(b) measuring the ability of said VHH or functional fragment thereof to bind HER-2 positive cancer lesion in the subject.

28. The method of claim 27, wherein the radioisotope has a physical half-life of less than two hours.

29. The method of claim 27, wherein the $V_{HH}$ or a functional fragment thereof further comprises a chelating agent.

30. The method of claim 29, wherein the chelating agent is selected from the group consisting of 1,4,7-triazacyclononane-N-succinic acid-N',N''-diacetic acid (NODASA), 1,4,7-triazacyclononane-N-glutamic acid-N',N''-diacetic acid (NODAGA), 1,4,7,10-tetraazacyclododecane-1,4,7,10-tetraacetic acid (DOTA), 1,4,7-triazacyclononane-1,4,7-triacetic acid (NOTA), and derivatives thereof.

* * * * *